(12) United States Patent
Pulé et al.

(10) Patent No.: US 10,704,032 B2
(45) Date of Patent: Jul. 7, 2020

(54) RETROVIRUS PACKAGING CELL

(71) Applicant: UCL Business LTD, London (GB)

(72) Inventors: Martin Pulé, London (GB); Leila Mekkaoui, London (GB); Gordon Weng-Kit Cheung, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 16/079,940

(22) PCT Filed: Feb. 24, 2017

(86) PCT No.: PCT/GB2017/050482
§ 371 (c)(1),
(2) Date: Aug. 24, 2018

(87) PCT Pub. No.: WO2017/144893
PCT Pub. Date: Aug. 31, 2017

(65) Prior Publication Data
US 2019/0055526 A1    Feb. 21, 2019

(30) Foreign Application Priority Data

Feb. 26, 2016   (GB) .................................. 1603374.8

(51) Int. Cl.
| | |
|---|---|
| *C07H 21/04* | (2006.01) |
| *A61K 38/00* | (2006.01) |
| *A61K 48/00* | (2006.01) |
| *C12N 15/113* | (2010.01) |
| *A61K 39/12* | (2006.01) |
| *C12N 9/12* | (2006.01) |
| *C07K 14/005* | (2006.01) |

(52) U.S. Cl.
CPC ............ *C12N 9/127* (2013.01); *C07K 14/005* (2013.01); *C12N 2770/36122* (2013.01); *C12N 2770/36151* (2013.01); *C12N 2770/36152* (2013.01)

(58) Field of Classification Search
CPC .. C12N 15/113; C12N 2310/14; C12N 15/86; C12Q 1/703; A61K 38/00
See application file for complete search history.

(56) References Cited

U.S. PATENT DOCUMENTS

| 6,008,035 A | 12/1999 | Johnston et al. |
|---|---|---|
| 2005/0032043 A1 | 2/2005 | Palese et al. |

FOREIGN PATENT DOCUMENTS

| EP | 1642982 A1 | 4/2006 |
|---|---|---|
| WO | WO-94/29438 A1 | 12/1994 |
| WO | WO-97/27310 A1 | 7/1997 |
| WO | WO-99/50432 A1 | 10/1999 |
| WO | WO-01/39797 A2 | 6/2001 |
| WO | WO-02/077221 A1 | 10/2002 |
| WO | WO-02/097080 A2 | 12/2002 |
| WO | WO-2012/170431 A2 | 12/2012 |
| WO | WO2012170431 | * 12/2012 |

OTHER PUBLICATIONS

Altschul et al., Basic local alignment search tool, J. Mol. Biol., 215(3):403-10 (1990).
Ausubel et al., Short Protocols in Molecular Biology, 4th edition, Chapter 18 (1999).
Ausubel et al., Short Protocols in Molecular Biology, pp. 7-58 to 7-60 (1999).
Boorsma et al., A temperature-regulated replicon-based DNA expression system, Nat. Biotechnol., 18(4):429-32 (Apr. 2000).
Burge et al., Temperature-sensitive mutants of Sindbis virus: biochemical correlates of complementation, J. Virol., 1(5):956-62 (Oct. 1967).
Coffin et al., Retorviruses, Cold Spring Harbour Laboratory Press, pp. 758-763 (1997).
Devereux et al., A comprehensive set of sequence analysis programms for the VAX. *Nucl. Acids Res.*12: 387-95 (1984).
Dryga et al., Identification of mutations in a Sindbis virus variant able to establish persistent infection in BHK cells: the importance of a mutation in the nsP2 gene, Virology, 228(1):74-83 (Feb. 1997).
Hahn et al., Mapping of RNA—temperature-sensitive mutants of Sindbis virus: complementation group F mutants have lesions in nsP4, J. Virol., 63(3):1194-202 (Mar. 1989).
International Application No. PCT/GB2017/050482, International Preliminary Report on Patentability, dated Aug. 28, 2018.
International Application No. PCT/GB2017/050482, International Search Report and Written Opinion, dated Jun. 19, 2017.
Kwissa et al., Polyvalent DNA vaccines with bidirectional promoters, J. Mol. Med. (Berl)., 78(9):495-506 (2000).
Miyazaki et al., Expression vector system based on the chicken beta-actin promoter directs efficient production of interleukin-5, Gene, 79(2):269-77 (Jul. 1989).
Sheridan et al., Generation of retroviral packaging and producer cell lines for large-scale vector production and clinical application: improved safety and high titer, Mol. Ther., 293):262-75 (Sep. 2000).
Thal et al., Template requirements for recognition and copying by Sindbis virus RNA-dependent RNA polymerase, Virology, 358(1):221-32 (Feb. 2007).
Verma et al., Gene therapy—promises, problems and prospects, Nature, 389(6648):239-42 (Sep. 1997).
NCBI Genbank Database Genome Accession No. AF033819, Human immunodeficiency virus 1.
NCBI Genbank database Genome Accession No. AF033820, Equine infectious anemia virus complete genome (Dec. 3, 1998).

(Continued)

*Primary Examiner* — Barry A Chestnut

(74) *Attorney, Agent, or Firm* — Marshall, Gerstein & Borun LLP

(57) ABSTRACT

The present invention relates to a retrovirus packaging cell which expresses a temperature sensitive RNA-dependent-RNA polymerase (RdRp).

19 Claims, 22 Drawing Sheets

Specification includes a Sequence Listing.

(56) References Cited

OTHER PUBLICATIONS

NCBI Reference Sequence NC_001547.1, Sindbis virus, complete genome (Aug. 13, 2018).
NCBI Reference Sequence NC_001786.1, Barmah Forest virus, complete genome (Aug. 13, 2018).
NCBI Reference Sequence NC_003215.1, Semliki forest virus, complete genome (Aug. 13, 2018).
NCBI Reference Sequence NC_003899.1, eastern equine encephalitis virus, complete genome (Aug. 13, 2018).
NCBI Reference Sequence NC_003900.1, Aura virus, complete genome (Aug. 13, 2018).
Qiang et al., The Initial Establishment of a New Poxviral/Lentivral Hybrid System for Efficient Lentiviral Vector Production, Progress in Biochemistry and Biophysics, 34(8):836-43 (2007).
Yusa et al., A hyperactive piggyBac transposase for mammalian applications, Proc. Natl. Acad. Sci. USA, 108(4):1531-6 (Jan. 2011).

* cited by examiner (a)

(b)

SEQ ID NO: 1 - Shows Sindbis plasmid (987SinRep) base pair sequence annotated with GOI instead of structural genes:

5'.genome-sequence-RSV-LTR.Sindbis(NSP1-*NSP2*-NSP3-*NSP2.protease.cleavage.site*-NSP4).Subgenomic.promoter(Psg)- X (any nucleotide sequence of interest)-3'.genome-sequence CTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGG
CACCTCGACCCCAAAAAACTTGATTAGGGTGATGGTTCACGTAGTGGGCCATCGCCCTGATAGACGGTTTTTCGCCCTTTGACGTTGGAGTCCACGT
TCTTTAATAGTGGACTCTTGTTCCAAACTGGAACAACACTCAACCCTATCTCGGTCTATTCTTTTGATTTATAAGGGATTTTGCCGATTTCGGCCTA
TTGGTTAAAAAATGAGCTGATTTAACAAAAATTTAACGCGAATTTTAACAAAATATTAACGCTTACAATTTCCATTCGCCATTCAGGCTGCGCAACT
GTTGGGAAGGGCGATCGGTGCGGGCCTCTTCGCTATTACGCCAGCTGGCGAAAGGGGGATGTGCTGCAAGGCGATTAAGTTGGGTAACGCCAGGGTT
TTCCCAGTCACGACGTTGTAAAACGACGGCCAGTGAATTGTAATACGACTCACTATAGGGCGAATTGGATCCGACCGCGAAGGTCAATGCCCCGTAC
ATTCGCATTCGAGCACAGCAACTCTCCAAGAGTCGACAGTACATGTCCTGGAGAAAGGAGCGGTGACAGTACACTTTAGCACCGCGAGTCCACAGGC
GAACTTTATCGTATCGCTGTGTGGGCTAGTGGATCCGG*AGTCTTATGCAATACTCTTGTAGTCTTGCAACATGGTAACGATGAGTTAGCAACATGCC*
*TTACAAGGAGAGAAAAAGCACCGTGCATGCCGATTGGTGGAAGTAAGGTGGTACGATCGTGCCTTATTAGGAAGGCAACAGACGGGTCTGACATGGA*
*TTGGACGAACCACTGAATTCCGCATTGCAGAGATATT*GTATTTAAGTGCCTAGCTCGATACCGTCGAGATTGACGGCGTAGTACACACTATTGAATC
AAACAGCCGACCAATTGCACTACCATCACAATGGAGAAGCCAGTAGTAAACGTAGACGTAGACCCCCAGAGTCCGTTTGTCGTGCAACTGCAAAAAA

FIG. 8

```
GCTTCCCGGCAATTTGAGGTAGTAGCACAGCAGGTCACTCCAAATGACCATGCTAATGCCAGAGCATTTTCGCATTCGGCCAGTAAACTAATCGAGCT
GGAGGTTCCTACCACAGACCCGGACCGACGATCTTGGACATAGGCAGCGCACCGGCTCGTAGAATGTTTTCCGAGCACCAGTATCATTGTGTCTGCCCATGCGT
AGTCCAGAAGACCCGGACCGCGCATGATGAAATATGCCAGTGAAACAAGCGTGCAAGATTACAAACAAGAACTTGCATGAGAAGATTAAGG
ATCTCCGGACCGTACTTGATACGCCGATGCTGAAACACCATCGCTCTGCTTTCACAACGATGTTACCTGCAACATGCCTGCCGAATATTCCGTCAT
GCAGGAGCGTGTATATCAAGCGCTCCCGGAACTATCTATCATCAGGCTATGAAAGGCGTGCGGACCCTGTACTGGATTGGCTTGACACCACCAGTTC
ATGTTCTCGGCTATGGCCAGGTTCGACAGGAGACAAGAATTGTCAGAACTGGGCCGACGAGAAGTCCTTGAAGCGCTAACATCGGACTTTGCAGCACAA
AGCTGAGTGAGTTAGGACACAGGAAGAAGGAGTTGAAGCCCGGGTCGCGGGTTTATTTCTCGTAGGATCGATCACTTTA
TCCAGAACACAGACCAGCTTGCAGAGCTGGCATCTTCCATCGGTGTTCCACTTGAATGGAAAGCAGTCGTACACTTGCCGCTGTGATACAGTGGTG
AGTTGCGAAGGCTACGTAGTGAAGAAAATCACCATCAGTCCCGGATCACGGGAGAAAACCGTGGATACGCGTTACACACAATAGCGAGGCTTCT
TGCTATGCAAAGTTACTGACAGTATATCACCTGACGATGACACTAAAGGAGAACGGTATCGTTCCCTGTGCACGGGTTCAGCAAATGGGCTAAGAGCGCAAGATCTTCATTAACGCGTAAGGACTAACAGGAACACCAAC
AATGGCCACGGATATATTACCTTCTGCCGATCATAGCACTTACGTATGCTGCTTGTGGCGTTTCCCATGTCGTCTGGAGGCAAGAAAGTACATTCGTTTTATCGCCCACCTGGAACGCAGACCTGCTAA
ACCATGCAAAATTACCTTCTGCCGATCATAGCACCTGACGATGACACATAGAAAGTACATTCGTTTTATCGCCCACTGGAACGCAGACCTGCTGAA
CTAGAGAACGCAAGCTTACGTATGCTCTTGTGGCGTTTCCATGTCGTCTGCCAAGTGCTTTTGAGGATGCTCAGGAGGCAAGAAATTGAAACTGGCATTGCAACCA
AGTCCCAGCCTCTTTTAGCGCTTTTCCCAGTCTCGCAGGTCGTCCAGGTATGATGATCATGAGGCAGCCGCAGAAGTGCTGAAGATCTCAGGAGGAAGCCAGAGCGGAGAAGC
AAGAAGGAGAAGCACTTCCACCATTAGTGCCAGACAAAGGCATGGAGGCATCGAGGGCTCCAGGCGACATCGGAGC
TCCGAGAAGCACTTCCACCATTAGTGCCAGACAAAGGCATCGAGGGCTCCAGGCGACATCGGAGC
AGCATTAGTTGAAACCCGGCGGGTCACGTAAGGATAATACCTCAAGCAATGACCGTATGATCGACAGTATATCGTTGCTCGCCAAACTCTGTG
CTGAAGAATGCCAAATCGCACGTAGCTAAGGATAATACCTCAGTCAGTTAAGATCAGTTAAGATCATAACACTCGGAGATCAGGAAGTACGCGGTGAACCAT
ACGAGCTAAGTACTGATGCCAAGCAGGAGTGCCAGCAGGAGGTCCAGAATTCCTAGCACTGAGTGAGAGCGCCACGTTAGTGTACAACGAAAGAGA
GTTTGTGAACCGCAAACTATACCATTGCCAATGCCCATGCATGGCCCCAAGAATACAGAAGAGAGCAGTACAAGGTTACAAGGCAGAGCTTGCAGAA
ACAGAGTACGTGTTGACGTGACAAGAAGCGTTGCGTTAAGAAGGAAGCCTCCAGGTCCTCTCGGGAGAACGTCTCAGGTCCTCTCGGGAGAACCTGACCAACCCTCCCTATC
ATGAGCTAGCTCGGAGGGACTCGAAGACCCGGAGGTCGAAACAATAGGAGTGATAGGCACACCGGGTCGGCAAGTCAGC
```

```
GCTGCGGGCGAGCGGGTATCAGCTCACTCAAAGGCGGTAATACGGTTATCCACAGAATCAGGGGATAACGCAGGAAAGAACATGTGAGCAAAAGGCCAG
CAAAAGGCCAGGAACCGTAAAAAGGCCGCGTTGCTGGCGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAATTAAAAATGAAGTTTAATCAATCTAAAGTAT
ATATGAGTAAACTTGGTCTGACAGTTACCAATGCTTAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTACAGGCATCGTGGTGTCACGCTCGTCGTTTGGTATGGCTTCATTCAGC
TCCGGTTCCCAACGATCAAGGCGAGTTACATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAAGATGCTTTTCTGTGACTGGTGAGTACTC
AACCAAGTCATTCTGAGAATAGTGTATGCGGCGACCGAGTTGCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTGTTGAGATCCAGTTCGATGTAACCCACTCGTGCACCCAACT
GATCTTCAGCATCTTTTACTTTCACCAGCGTTTCTGGGTGAGCAAAAACAGGAAGGCAAAATGCCGCAAAAAAGGGAATAAGGGCGACACGGAAATG
TTGAATACTCATACTCTTCCTTTTTCAATATTATTGAAGCATTTATCAGGGTTATTGTCTCATGAGCGGATACATATTTGAATGTATTTAGAAAAAT
AAACAAATAGGGGTTCCGCGCACATTTCCCCGAAAAGTGCCAC
```

X = any nucleotide sequence of interest

FIG. 8 (continued)

SEQ ID NO: 2

Shows 987.SinRep amino acid sequence with P726S (non-cytotoxic) and G153E (RdRp-temprature-regulated) mutations, 987*SinRep:

NSP1.NSP2(P726→S).NSP3.protease-cleavage-site.NSP4(G153→E)

MEKPVVNVDVDPQSPFVVQLQKSFPQFEVVAQQVTPNDHANARAFSHLASKLIELEVPTTATILDIGSAPARRMFSEHQYHCVCPM
RSPEDPDRMMKYASKLAEKACKITNKNLHEKIKDLRTVLDTPDAETPSLCFHNDVTCNMRAEYSVMQDVYINAPGTIYHQAMKGVR
TLYWIGFDTTQFMFSAMAGSYPAYNTNWADEKVLEARNIGLCSTKLSEGRTGKLSIMRKKELKPGSRVYFSVGSTLYPEHRASLQS
WHLPSVFHLNGKQSYTCRCDTVVSCEGYVVKKITISPGITGETVGYAVTHNSEGFLLCKVTDTVKGERVSFPVCTYIPATICDQMT
GIMATDISPDDAQKLLVGLNQRIVINGRTNRNTNTMQNYLLPIIAQGFSKWAKERKDDLDNEKMLGTRERKLTYGCLWAFRTKKVH
SFYRPPGTQTCVKVPASFSAFPMSSVWTTSLPMSLRQKLKLALQPKKEEKLLQVSEELVMEAKAAFEDAQEEARAEKLREALPPLV
ADKGIEAAAEVVCEVEGLQADIGAALVETPRGHVRIIPQANDRMIGQYIVVSPNSVLKNAKLAPAHPLADQVKIITHSGRSGRYAV
EPYDAKVLMPAGGAVPWPEFLALSESATLVYNEREFVNRKLYHIAMHGPAKNTEEEQYKVTKAELAETEYVFDVDKKRCVKKEEAS
GLVLSGELTNPPYHELALEGLKTRPAVPYKVETIGVIGTPGSGKSAIIKSTVTARDLVTSGKKENCREIEADVLRLRGMQITSKTV
DSVMLNGCHKAVEVLYVDEAFACHAGALLALIAIVRPRKKVVLCGDPMQCGFFNMMQLKVHFNHPEKDICTKTFYKYISRRCTQPV
TAIVSTLHYDGKMKTTNPCKKNIEIDITGATKPKPGDIILTCFRGWVKQLQIDYPGHEVMTAAASQGLTRKGVYAVRQKVNENPLY
AITSEHVNVLLTRTEDRLVWKTLQGDPWIKQLTNIPKGNFQATIEDWEAEHKGIIAAINSPTPRANPFSCKTNVCWAKALEPILAT

FIG. 8 (continued)

AGIVLTGCQWSELFPQFADDKPHSAIYALDVICIKFFGMDLTSGLFSKQSIPLTYHPADSARPVAHWDNSPGTRKYGYDHAIAAEL
SRRFPVFQLAGKGTQLDLQTGRTRVISAQHNLVPVNRNLPHALVPEYKEKQPGPVEKFLNQFKHHSVLVVSEEKIEAPRKRIEWIA
PIGIAGADKNYNLAFGFPPQARYDLVFINIGTKYRNHHFQQCEDHAATLKTLSRSALNCLN (P→S) GGTLVVKSYGY SEQ ID NO: 3 - eGFP - amino acid sequence:

MVSKGEELFTGVVPILVELDGDVNGHKFSVSGEGEGDATYGKLTLKFICTTGKLPVPWPTLVTLTYGVQCFSRYPDHM
KQHDFFKSAMPEGYVQERTIFFKDDGNYKTRAEVKFEGDTLVNRIELKGIDFKEDGNILGHKLEYNYNSHNVYIMADKQ
KNGIKVNFKIRHNIEDGSVQLADHYQQNTPIGDGPVLLPDNHYLSTQSALSKDPNEKRDHMVLLEFVTAAGITLGMDE
LYK*

SEQ ID NO: 4 - VSVG - amino acid sequence

MKCLLYLAFLFIGVNCKFTIVFPHNQKGNWKNVPSNYHYCPSSSDLNWHNDLIGTALQVKMPKSHKAIQADGWMCH
ASKWVTTCDFRWYGPKYITHSIRSFTPSVEQCKESIEQTKQGTWLNPGFPPQSCGYATVTDAEAVIVQVTPHHVLVDEY
TGEWVDSQFINGKCSNYICPTVHNSTTWHSDYKVKGLCDSNLISMDITFFSEDGELSSLGKEGTGFRSNYFAYETGGKA
CKMQYCKHWGVRLPSGVWFEMADKDLFAAARFPECPEGSSISAPSQTSVDVSLIQDVERILDYSLCQETWSKIRAGLPI
SPVDLSYLAPKNPGTGPAFTIINGTLKYFETRYIRVDIAAPILSRMVGMISGTTTERELWDDWAPYEDVEIGPNGVLRTSS
GYKFPLYMIGHGMLDSDLHLSSKAQVFEHPHIQDAASQLPDDESLFFGDTGLSKNPIELVEGWFSSWKSSIASFFFIIGLII
GLFLVLRVGIHLCIKLKHTKKRQIYTDIEMNRLGK*

SEQ ID NO: 5 - Gag: Pol – DNA sequence

ATGGGAGCACGGCTAGTGTCTTTTCTGGAGGTGAGCTTGACAGGTGAGCTTGACACCCCGGCGGCCCCGGCGGCCAAAAAGAAGTACAAGCTGAAGC
ACATCGTGTGGGCCCTCTCGCGAATTGAGAGAGGTTTGCCGTCGAATTGAGAGAGGTTTGCCGTCGAACCCCGAGCTCCTGGAGACAGATCAGACTTGGAGACAAGCCAGGGTTGCCGGAGATCCTCGGCCAATTGCA
GCCCAGTTGCAAACCGGACCAGCGGAGGAGTTGCCGGAGCCTGTACAACCGTGTACAACCGTGGCCACACCGTGGCCACAGCGATCTGCTCCACCAGCCATCGAAATCAAGGATACA
AAAGAGGCCCTGATAAAATCGAAGAGGAACAGAATAAGAGCAAAAAGAGCAAAAAGAAGCCCAACAAGCCCGCCGCTGATACCGCCATTCTAACCAAGTGTCTC

RETROVIRUS PACKAGING CELL

CROSS-REFERENCE TO RELATED APPLICATIONS

This application is a National Stage Application of International Patent Application No. PCT/GB2017/050482, filed Feb. 24, 2017, which claims the priority benefit from Great Britain Patent Application No. 1603374.8, filed Feb. 26, 2016.

FIELD OF THE INVENTION

The present invention relates to the field of retroviral vectors. In particular, the invention relates to methods for producing retroviral vectors and to packaging cells and producer cells for use in such methods.

BACKGROUND TO THE INVENTION

Retroviral vectors are relevant for a range of applications, including gene therapy. However, progress in lentiviral gene therapy, for example, has been hampered by the requirement for production of purified lentiviral vectors with high titre.

A major limitation in the production of lentiviral vectors is the lack of appropriate stable producer cells and the low viral titre produced by most packaging cell lines. Currently, all large scale lentiviral production is generated by transient transfection methods. Until the problem of stable packaging cell lines is solved, lentiviral production cannot be fully industrialized.

The main challenges with making stable producer cell lines include the fact that high numbers of transfer vector transgenes are needed to generate appropriate viral titres. Transfer vector transgenes comprise the gene of interest which is to be delivered by the viral vector and the elements required for integration of the gene of interest into the host genome. The number of RNA transgenes which can be accumulated in the cytoplasm of producer cells is limited because the long transcripts of the transgenes are poorly transcribed and poorly exported from the nucleus.

In addition, high levels of lentiviral proteins such as gagpol and envelope proteins are needed to produce required lentiviral titres. This is difficult to achieve because gagpol is unstable and difficult to express and fold correctly. Another problem is the basal toxicity associated with the protease activity of gagpol. Further, a number of preferred envelopes for lentiviral pseudotyping—such as VSV-G—cause syncytial formation and are also basally toxic.

Accordingly, there is a need for alternative producer cells and methods for producing retroviral vectors.

SUMMARY OF ASPECTS OF THE INVENTION

The present inventors have determined that levels of retroviral transfer vector transgenes may be amplified during retroviral vector production by using an RNA-dependent RNA polymerase (RdRp) to amplify the transgenes in the cytoplasm of a producer cell. Such cytoplasmic amplification means that nuclear export of long, complex transfer vector transgenes is no longer a limiting factor on the lentiviral titre. In particular, the inclusion of a subgenomic RdRp promoter within the transgene transcripts allows them to be exponentially amplified in the cytoplasm by the RdRp (see FIG. 2).

The present inventors have also determined that the use of packaging cells or producer cells which (i) comprise nucleic acid sequences that are transcribed into mRNA which encodes toxic retroviral proteins, such as gagpol and env proteins, under the control of a RdRp subgenomic promoter and (ii) expressing a temperature sensitive RdRp; enables the expression of the toxic retroviral proteins to be induced in a controllable manner. Translation of toxic proteins can therefore be prevented, for example, until producer cell cultures are confluent. At this point the temperature of the culture can be altered, which causes the production of large amounts of mRNA. This is still ultimately toxic to the producer cell—but at this stage large amounts of producer cells are present and large amount of virus are produced and the cultures are terminated (see FIG. 3).

In a first aspect the present invention provides a retrovirus packaging cell which expresses a temperature sensitive RNA-dependent-RNA polymerase (RdRp). For example, the temperature sensitive RdRp may comprise the sequence shown as SEQ ID NO: 2 or a variant thereof.

In another aspect the present invention provides a retrovirus packaging cell which expresses a RNA-dependent-RNA polymerase (RdRp).

The RdRp may be encoded by a nucleic acid sequence which is stably integrated into the genome of the packaging cell.

The RdRp may be an alphavirus RdRp, for example a Sindbis virus RdRp.

The RdRp may be encoded by a nucleotide sequence which comprises a sequence shown as SEQ ID NO: 6 or a variant thereof.

In a further aspect the present invention provides a retrovirus producer cell which is a packaging cell according to the first aspect of the invention, further comprising a retroviral nucleic acid transfer vector which comprises at least one RdRp promoter element which enables the retroviral nucleic acid transfer vector to be replicated by the RdRp. In other words the RdRp promoter element is operably linked to the retroviral nucleic acid transfer vector to be replicated by the RdRp.

The retroviral nucleic acid transfer vector may comprise the following structure:

5'P1-rPSG-⁵dLTR-P2-NOI-³dLTR-PSG3' in which

P1 is a eukaryotic promoter which drives transcription rPSG is a sequence which acts as a negative sense sub-genomic promoter for the RdRp when at the 3' end of the negative sense strand;

⁵dLTR is a truncated 5' retrovirus long terminal repeat where the U3 region is non-functioning (e.g. has been deleted, truncated, mutated or substituted)

P2 is a eukaryotic promoter which drives expression of the NOI;

NOI is a nucleotide sequence of interest;

³dLTR is a self-inactivating 3' retrovirus long terminal repeat with a non-functioning (e.g. has been deleted, truncated, mutated or substituted) U3;

PSG is a sequence which acts as a sub-genomic promoter for RdRp as a positive sense.

Suitably, the ⁵dLTR is a truncated 5' retrovirus long terminal repeat where the U3 region is deleted and the ³dLTR is a self-inactivating 3' retrovirus long terminal repeat with a truncated U3.

A nucleic acid sequence encoding the retroviral nucleic acid transfer vector may be stably integrated into the packaging cell genome.

The retrovirus packaging cell or a producer cell of the present invention may comprise at least one retroviral helper element nucleotide sequence comprising at least one RdRp promoter element which enables a nucleic acid sequence which encodes a retroviral protein to be replicated by the RdRp. In other words, the RdRp promoter element is operably linked to the nucleic acid sequence which encodes a retroviral protein. The retrovirus packaging cell or a producer cell of the present invention may comprise at least one retroviral helper element nucleotide sequence comprising the following structure:

5'-rPSG-RetroP-PSG3' in which
P is a eukaryotic promoter;
rPSG is a sequence which acts as a negative sense sub-genomic promoter for the RdRp when at the 3' end of the negative sense strand;
RetroP is nucleic acid sequence which encodes a retrovirus protein; and
PSG is a sequence which acts as a sub-genomic promoter for RdRp as positive sense.

The retrovirus packaging cell or a producer cell of the present invention may comprise at least one retroviral helper element nucleotide sequence comprising the following structure:

5'-rPSG-rRetroP-PSG3' in which
P is a eukaryotic promoter;
rPSG is a sequence which acts as a negative sense sub-genomic promoter for the RdRp when at the 3' end of the negative sense strand
rRetroP is nucleic acid sequence which encodes a retrovirus protein in reverse orientation
PSG is a sequence which acts as a sub-genomic promoter for RdRp as a positive sense.

The retrovirus packaging cell or a producer cell of the present invention may comprise at least one retroviral helper element nucleotide sequence comprising the following structure:

5'P-MG-STOP-iPSG-RetroP-PSG3' in which
P is a eukaryotic promoter;
MG is an open reading frame of a non-toxic marker gene;
STOP is a stop signal;
iPSG is a reverse-orientation RdPg sub-genomic promoter which works internally; RetroP is nucleic acid sequence which encodes a retrovirus protein; and
PSG is a sequence which acts as a sub-genomic promoter for RdRp as a positive sense.

The retrovirus packaging cell or a producer cell of the present invention may comprise at least one retroviral helper element nucleotide sequence comprising the following structure:

5'P-rPSG-MG-STOP-iPSG-RetroP-PSG3' in which
P is a eukaryotic promoter;
rPSG is a sequence which acts as a negative sense sub-genomic promoter for the RdRp when at the 3' end of the negative sense strand
MG is an open reading frame of a non-toxic marker gene
STOP is a stop signal or a series of stop signals
iPSG is a reverse-orientation RdPg sub-genomic promoter which works internally RetroP is nucleic acid sequence which encodes a retrovirus protein; and PSG is a sequence which acts as a sub-genomic promoter for RdRp as a positive sense.

The retrovirus protein may selected from gag-pol, env or rev. The retrovirus protein may be gag-pol or env.

The retrovirus packaging cell or a producer cell of the present invention may comprise a plurality of retroviral helper element nucleotide sequences according to the present invention, wherein the retroviral helper element nucleotide sequences each encode a different retrovirus protein.

The retrovirus packaging cell or a producer cell of the present invention may be a lentiviral packaging cell or a producer cell.

The retrovirus packaging cell or a producer cell of the present invention may be a HEK293, HEK293-T, TE671, HT1080, 3T3, or K562 cell.

In another aspect the present invention provides a retroviral nucleic acid transfer vector which comprises at least one RdRp promoter element which enables the retroviral nucleic acid transfer vector to be replicated by the RdRp. In other words the RdRp promoter element is operably linked to the retroviral nucleic acid transfer vector to be replicated by the RdRp.

The retroviral nucleic acid transfer vector may comprise the following structure:

5P1-rPSG-5dLTR-P2-NOI-3dLTR-PSG3' in which
P1 is a eukaryotic promoter which drives transcription;
rPSG is a sequence which acts as a sub-genomic promoter for the RdRp as negative sense;
5dLTR is a truncated 5' retrovirus long terminal repeat where the U3 region is non-functioning (e.g. has been deleted, truncated, mutated or substituted);
P2 is a eukaryotic promoter which drives expression of the NOI;
NOI is a nucleotide sequence of interest;
3dLTR is a non-functioning (e.g. has been deleted, truncated, mutated or substituted) 3' retrovirus long terminal repeat; and
PSG is a sequence which acts as a sub-genomic promoter for RdRp as a positive sense.

Suitably, the 5dLTR is a truncated 5' retrovirus long terminal repeat where the U3 region is deleted and the 3dLTR is a self-inactivating 3' retrovirus long terminal repeat with a truncated U3.

In another aspect the present invention provides a retroviral helper element nucleotide sequence comprising at least one RdRp promoter element which enables a nucleic acid sequence which encodes a retroviral protein to be replicated by the RdRp.

The retroviral helper element nucleotide sequence may be any retroviral helper element nucleotide sequence according to the present invention.

In another aspect the present invention provides a plasmid comprising a retroviral nucleic acid transfer vector or a retroviral helper element nucleotide sequence of the invention.

In a further aspect the present invention relates to a method for making a packaging cell which comprises the step of introducing a nucleic acid sequence encoding a RdRp as defined herein into a cell, such that the cell expresses the RdRp.

The method may further comprise the step of introducing a retroviral helper element nucleotide sequence of the invention into the cell.

In a further aspect the present invention provides a method for making a producer cell which comprises the step of introducing a retroviral helper element nucleotide sequence of the invention into the cell, and further comprises the step of introducing a retroviral nucleic acid transfer vector of the invention into the cell.

In one aspect the present invention provides a method for making a producer cell which comprises introducing a retroviral helper element nucleotide sequence of the invention into the cell and separately introducing a retroviral nucleic acid transfer vector of the invention into the cell.

In one aspect the present invention provides a method for making a producer cell which comprises introducing a retroviral helper element nucleotide sequence of the invention into the cell and simultaneously introducing a retroviral nucleic acid transfer vector of the invention into the cell.

In one aspect the retroviral nucleic acid transfer vector of the invention may additionally comprise a retroviral helper element nucleotide sequence of the invention.

In another aspect the present invention provides method for making a producer cell which comprises the step of introducing a retroviral nucleic acid transfer vector of the invention into a retrovirus packaging cell of the invention.

In a further aspect the present invention relates to a method for making a retrovirus vector which comprises the step of culturing a producer cell according to the present invention and isolating the retrovirus vector.

The retrovirus vector may be a lentivirus vector.

In one aspect the present invention provides a method for making a retrovirus vector wherein the producer cell expresses a temperature sensitive RdRp as described herein and the method comprises culturing the producer cell at a relatively low temperature and isolating the retrovirus vector.

In a further aspect the present invention provides a method for expanding a population of packaging cells or producer cells according to the present invention by culturing the cells at a relatively high temperature.

In another aspect the present invention provides a method for increasing the production of retroviral proteins in a packaging cell or producer cell expressing a temperature sensitive RdRp as described herein by decreasing the temperature of the culture medium In one aspect the present invention provides a method for making a retrovirus vector wherein the producer cell expresses a temperature sensitive RdRp as described herein and the method comprises expanding a population of packaging cells or producer cells by culturing the cells at a relatively high temperature and subsequently culturing the producer cell at a relatively low temperature and isolating the retrovirus vector.

The relatively low temperature may be less than about 35° C. The relatively low temperature may be about 25° C. to about 29° C. The relatively low temperature may about 25, 26, 27, 28 or about 29° C.

The relatively high temperature may be about 35° C. to about 38° C. The relatively high temperature may be about 35, 36, 37 or about 38° C.

In another aspect the present invention provides a kit for making a packaging cell or a producer cell according to the present invention, which comprises:

i) at least two retroviral helper element nucleotide sequences according to the present invention; or ii) a retroviral nucleic acid transfer vector and a retroviral helper element nucleotide sequence according to the present invention.

DESCRIPTION OF THE FIGURES

FIG. 8—Sequences

DETAILED DESCRIPTION OF THE INVENTION

Packaging Cell and Producer Cell

Figure 1:
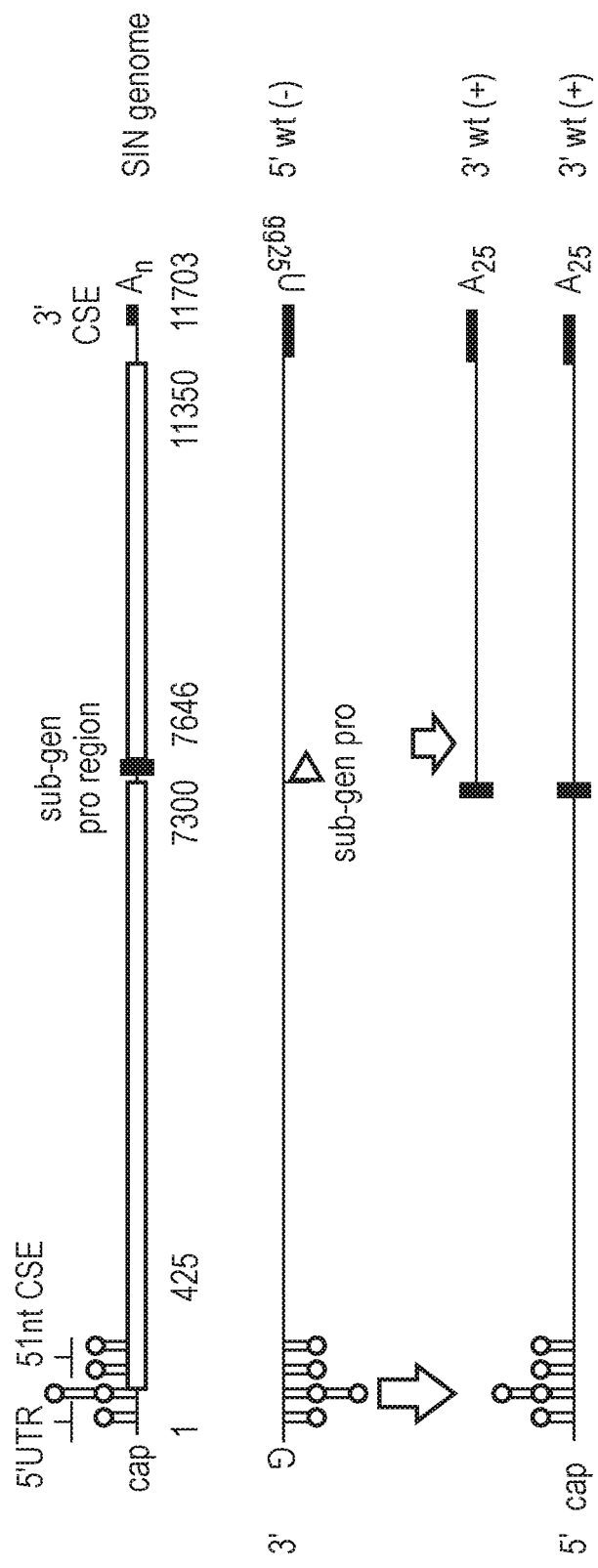
FIG. 1—Genome life-cycle of Sindbis virus. The genome starts as positive strand RNA. The 3' end of this is recognized by the RdRp and is copied into a negative strand. In turn, the 3' end of this (the 5' end of the original genome) is copied back into a positive strand. In addition, an internal sub-genomic promoter is recognized by RdRp on the negative strand and a shorter transcript is amplified. The portions of the genome needed for recognition have been determined experimentally and are detailed. UTR=untranslated region; CSE=conserved sequence element; An=polyadenylation signal; cap=5' cap structure.
Figure 2:
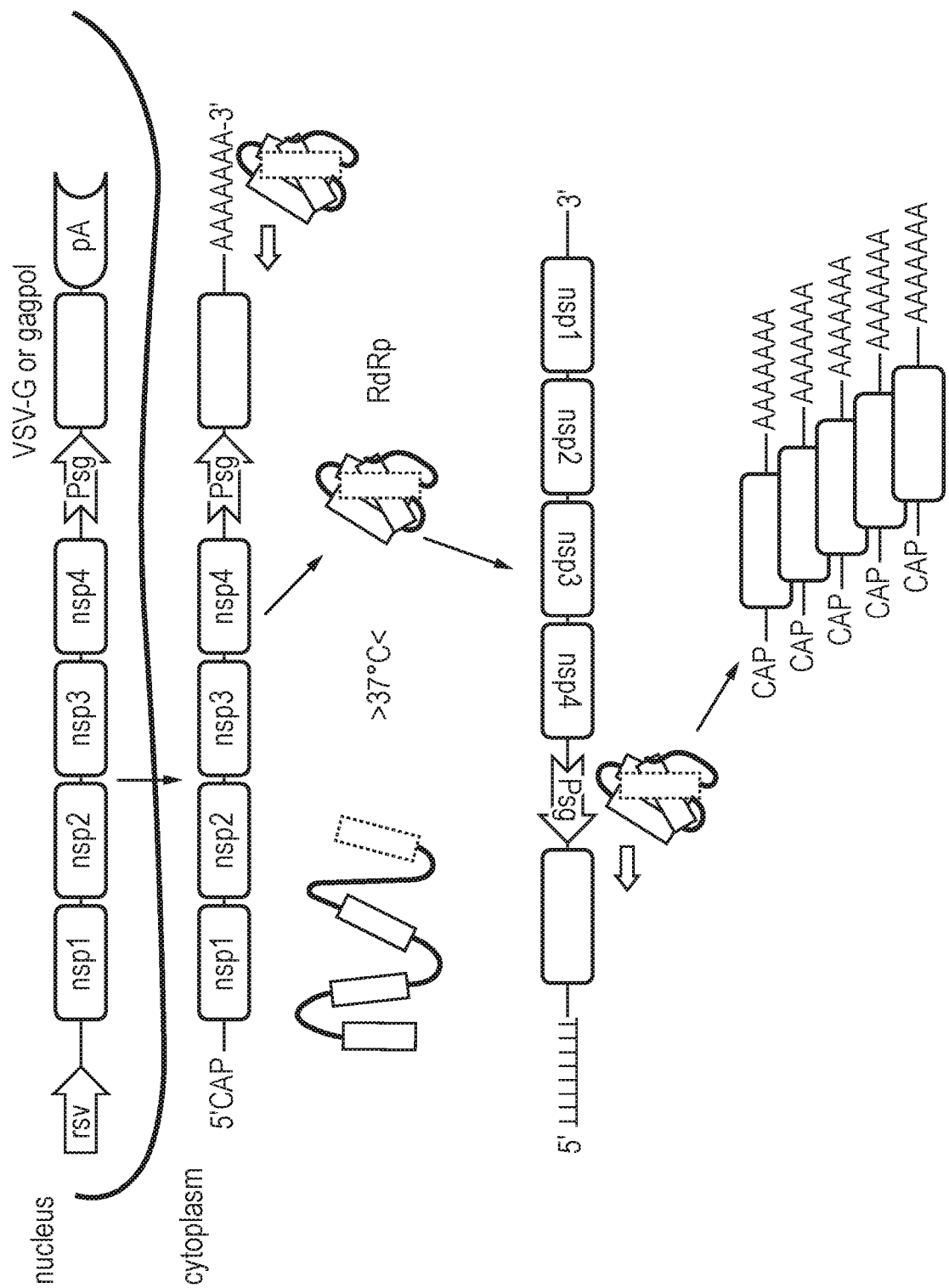
FIG. 2—Schematic diagram of a means of amplifying a retroviral nucleic acid transfer vector The RdRp (illustrated as Sindbis nsp1-4) is provided in trans (in a separate expression plasmid driven by an efficient eukaryotic promoter 'p') to a retroviral nucleic acid transfer vector. The retroviral transgene is stably integrated and is driven from a eukaryotic promoter. The subgenomic promoter is placed 5' to the R region of the 5'LTR. Elements from the sinbnis genome required for priming the 3' end are inserted into the U5 region of the 3'LTR. The genome is transcribed normally in the nucleus, exported to the cytoplasm where it is amplified by the sinbnis non-structural proteins.

As used herein, the term "packaging cell" refers to a cell which contains those elements necessary for production of infectious recombinant virus which are lacking in the RNA genome provided by a retrovirus nucleic acid transgene construct. Such packaging cells are capable of expressing viral structural proteins (such as gag-pol and env, which may be codon optimised) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

As used herein, the term "producer cell" refers to a cell which contains all the elements necessary for production of retroviral vector particles.

The producer cells/packaging cells of the present invention may be any suitable cell type. Producer cells are generally mammalian cells but can be, for example, insect cells.

By using producer/packaging cell lines of the present invention, it is possible to propagate and isolate quantities of retroviral vector particles (e.g. to prepare suitable titres of the retroviral vector particles) for subsequent transduction of a site of interest.

The packaging cell lines are useful for providing the gene products necessary to encapsidate and provide a membrane protein for a high titre vector particle production. The packaging cell may be a cell cultured in vitro such as a tissue culture cell line.

The packaging cell or producer cell of the present invention may be, but is not limited to, a mammalian cell such as a murine fibroblast derived cell or a human cell line. The packaging cell or producer cell of the present invention may be a human cell line, such as for example: HEK293, 293-T, TE671, HT1080, 3T3, or K562.

There are two common procedures for generating producer cells. In one, the sequences encoding retroviral Gag, Pol and Env proteins are introduced into the cell and stably integrated into the cell genome; a stable cell line is produced which is referred to as the packaging cell line. As used herein, the term "stably integrated" means that the foreign genes become integrated into the cell's genome. The packaging cell line produces the proteins required for packaging retroviral RNA but it cannot bring about encapsidation due to the lack of a psi region.

However, when a retrovirus nucleic acid transgene construct (having a psi region) is introduced into the packaging cell line, the helper proteins can package the psi-positive retrovirus nucleic acid transgene construct to produce the recombinant virus stock. This can be used to transduce recipient cells. The recombinant virus whose genome lacks all genes required to make viral proteins can infect only once and cannot propagate. Hence, a nucleic acid transgene construct can be introduced into a host cell genome without the generation of potentially harmful retrovirus.

The second approach is to introduce the three or more different DNA sequences that are required to produce a retroviral vector particle (i.e. the env coding sequences, the gag-pol coding sequence and the defective retroviral genome containing a transgene of interest (i.e. the retrovirus nucleic acid transgene construct) into the cell at the same time by transient transfection and the procedure is referred to as transient triple transfection. WO 94/29438 describes the production of producer cells in vitro using this multiple DNA transient transfection method. WO 97/27310 describes a set of DNA sequences for creating retroviral producer cells either in vivo or in vitro for re-implantation.

The components of the viral system which are required to complement the vector genome may be present on one or more "producer plasmids" for transfecting into cells.

The present invention provides a retroviral packaging cell which expresses a RNA-dependent-RNA polymerase (RdRp).

Accordingly, when a retroviral nucleic acid transfer vector as defined herein is introduced into the cell, the RNA-dependent RNA polymerase (RdRp) amplifies the transfer vector in the cytoplasm of the cell. Such cytoplasmic amplification means that nuclear export of long, complex transfer vector transgenes is no longer a limiting factor on the lentiviral titre. In one embodiment, the inclusion of a subgenomic promoter within the transgene transcripts allows them to be exponentially amplified in the cytoplasm by the RdRp.

RNA-Dependent RNA Polymerase (Rdrp) RNA-dependent RNA polymerase (RdRp), (RDR), or RNA replicase, is an enzyme that catalyzes the replication of RNA from an RNA template. This is in contrast to a typical DNA-dependent RNA polymerase, which catalyzes the transcription of RNA from a DNA template.

RdRp is an essential protein encoded in the genomes of all RNA-containing viruses with no DNA stage in their replication cycle. RdRp catalyses synthesis of the RNA strand which is complementary to a given RNA template. The RNA replication process is a two-step mechanism. First, the initiation step of RNA synthesis begins at or near the 3' end of the RNA template by means of a primer-independent (de novo), or a primer-dependent mechanism that utilizes a viral protein genome-linked (VPg) primer. The de novo initiation involves the addition of a nucleoside triphosphate (NTP) to the 3'-OH of the first initiating NTP. During the following so-called elongation phase, this nucleotidyl transfer reaction is repeated with subsequent NTPs to generate the complementary RNA product.

RNA-dependent RNA replication may be catalysed by a complex of proteins which provide, for example, a variety of related enzymatic activities. By way of example, productive RNA-dependent RNA replication may be achieved by the co-ordinated actions of a number of viral non-structural proteins (nsps). In one embodiment, the term RdRp as used herein encompasses a plurality of viral nsps which are required for productive RNA-dependent RNA replication. The plurality of viral nsps may be provided as a polyprotein (i.e. an amino acid sequence derived from a mRNA which is read as a single open-reading frame, from which at least two mature polypeptides are produced).

Superfamilies of viruses that cover RNA-containing viruses with no DNA stage include:
  Viruses containing positive-strand RNA or double-strand RNA—except retroviruses (e.g. Togaviridae, Cystoviridae, Reoviridae, Hypoviridae, Partitiviridae, Totiviridae, and Birnaviridae families);
  Mononegavirales (negative-strand RNA viruses with non-segmented genomes);
  Negative-strand RNA viruses with segmented genomes, (e.g. Orthomyxoviruses, Arenaviruses, Bunyaviruses, Hantaviruses, Nairoviruses, Phleboviruses, Tenuiviruses and Tospoviruses).

The RdRp used in the present invention may be a RdRp from any of the virus families mentioned above.

In a preferred embodiment the RdRp is from a virus of the togaviridae family. The Togaviridae family belong to group IV of the Baltimore classification of viruses. The Togaviridae genome is linear, single-stranded, positive sense RNA that is 10,000-12,000 nucleotides long. The 5'-terminus carries a methylated nucleotide cap and the 3'-terminus has a polyadenylated tail, therefore resembling cellular mRNA. The virus is enveloped and forms spherical particles (65-70 nm diameter), the capsid within is icosahedral, constructed of 240 monomers, having a triangulation number of 4. Entry into the host cell is achieved by attachment of the viral E glycoprotein to host receptors, which mediates clathrin-mediated endocytosis. The receptors for binding are unknown, however the tropism is varied and it is known that the glycoprotein petal-like spikes act as attachment proteins. After virus attachment and entry into the cell, gene expression and replication takes place within the cytoplasm.

Togaviridae replication follows the positive stranded RNA virus replication model described above. Positive-stranded RNA-virus-transcription is the method of transcription and translation takes place by viral initiation, and suppression of termination.

Examples of viruses from the togaviridae are the alphavirus and rubivirus generas.

In one embodiment, the RdRp is from an alphavirus. The alphavirus genera of viruses are small, icosahedral-shaped enveloped viruses approximately 70 nm in diameter. Their genome is a single-stranded positive-sense RNA genome of approximately 12 kbps in length. The non-structural polyprotein is responsible for copying the RNA genome and is read as a single frame but is processed to generate nsp1, nsp2, nsp3 and nsp4. Nsp1 is required for capping and methylating the newly synthesised genomic and subgenomic RNAs as it contains both guanine-7-methylatransferase and guanylyl transferase activities. It is also thought to anchor the replication machinery to the intracellular part of the plasma membrane during RNA replication. Nsp2 has been shown to exhibit both helicase and nucleoside triphosphatase activities within its amino-terminus, while its carboxyl-terminus seems to encode the viral cysteine protease that is required for processing of the non-structural polyproteins. Moreover, nsp3 has been suggested to play a role in RNA binding activity as well as encode an ADP-ribose 1-phosphate phosphatase. Finally, the nsp4 provides the RNA dependent RNA polymerase (RdRp) activity with the catalytic GDD motif in its carboxyl terminus while suggested to act as a scaffold for the interaction nsp1 to 3 by its amino-terminus.

Early in infection, the alphavirus genome is translated in the cytoplasm to generate both the nonstructural and structural polyproteins. Nsps are then cleaved between nsp3 and nsp4 to generate nsp123 and nsp4. Cleavage of nsp123 into nsp1 and nsp23 takes place when a sufficiently high concentration of the polyprotein has been transcribed. At this stage, the proteins nsp1, nsp23 and nsp4 form an unstable replication complex in order to synthesise negative-strand RNA for full-length genomic RNA synthesis but not subgenomic RNA synthesis. Once all four nsps proteins are cleaved into nsp1, nsp2, nsp3 and nsp4, they form a stable replication complex that switches from negative strand synthesis to positive strand genomic and subgenomic synthesis. During the transcription of the nsps polyproteins, the presence of leaky termination codon after nsp3, leads to an excess of nsp123 polyprotein compared to nsp1234, as read-through is suggested to be 10-20% efficient. In addition, another factor leading to the relatively decreased amount of RdRp compared to nsp123 is the presence of a destabilising tyrosine residue at the amino-terminus which has been shown to lead to rapid degradation of RdRp by the N-end rule pathway which only occurs when nsp4 is in excess. Removal of this destabilising tyrosine residue has been shown to affect the activity of RdRp and thus leads to a decreased RNA replication.

Examples of suitable alphaviruses include Aura virus; Barmah Forest virus; Bebaru virus; Cabassou virus; Chikungunya virus; Eastern equine encephalitis virus; Eilat virus; Fort Morgan virus; Getah virus; Highlands J virus; Madariaga virus; Mayaro virus; Middelburg virus; Mucambo virus; Ndumu virus; O'nyong-nyong virus; Pixuna virus; Rio Negro virus; Ross River virus; Salmon pancreas disease virus; Semliki Forest virus; Sindbis virus; Southern elephant seal virus; Trocara virus; Una virus; Venezuelan equine encephalitis virus; Western equine encephalitis virus and Whataroa virus. Sequences of RNAdRNAp can be identified from available complete genome sequences publically available such as Aura virus, complete genome: NC_003900.1; Barmah Forest virus: NC_001786.1; Eastern equine encephalitis virus, NC_003899.1; Semliki forest virus, complete genome: NC_003215.1 etc.

In one embodiment the RdRp is from a Sindbis virus. The Sindbis virus may be any strain of Sindbis virus. RNA-dependent RNA replication requires the function of each of nsp1, nsp2, nsp3 and nsp4 of the Sindbis virus. Accordingly, in one embodiment the nucleic acid sequence which encodes the RdRp encodes a Sindbis nsp1234 polyprotein which provides a RdRp activity.

Suitably nsp1, nsp2, nsp3 and nsp4 may be provided in trans i.e. they are provided by separate vectors e.g. nsp1 may be provided by a separate vector to nsp2 and/or nsp3 and/or nsp4.

In a preferred embodiment one, two, three or all four nsps are operably linked to the same promoter. The nucleotide sequences encoding the nsps may be contiguous or may be separated for example by self-cleaving sites e.g. 2A polypeptide sites.

In a particular preferred embodiment, nsps may be expressed as a single polypeptide that undergoes self-cleaving or, a polyprotein comprising individual nsp/self-cleaving 2A peptide fusion polypeptides.

In one embodiment a promoter is operably linked to nucleic acid sequence which encodes an nsp1,2,3,4 polyprotein—for example as described herein.

A nucleic acid sequence which encodes a RdRp as described herein may be provided as part a retrovirus nucleic acid transfer vector of the present invention or a retroviral helper element nucleotide sequence of the present invention.

The nucleic acid sequence may be any nucleic acid sequence which encodes a RdRp as described herein.

The nucleic acid sequence which encodes nsp1234 of a Sindbis virus may comprise the sequence shown as SEQ ID NO: 6.

```
                                          SEQ ID NO: 6
CTGACGCGCCCTGTAGCGGCGCATTAAGCGCGGCGGGTG

TGGTGGTTACGCGCAGCGTGACCGCTACACTTGCCAGC

GCCCTAGCGCCCGCTCCTTTCGCTTTCTTCCCTTCCTTT

CTCGCCACGTTCGCCGGCTTTCCCCGTCAAGCTCTAAA

TCGGGGGCTCCCTTTAGGGTTCCGATTTAGTGCTTTACG

GCACCTCGACCCCAAAAAACTTGATTAGGGTGATGGTT

CACGTAGTGGGCCATCGCCCTGATAGACGGTTTTTCGCC
```
-continued
```
CTTTGACGTTGGAGTCCACGTTCTTTAATAGTGGACTC

TTGTTCCAAACTGGAACAACACTCAACCCTATCTCGGTC

TATTCTTTTGATTTATAAGGGATTTTGCCGATTTCGGC

CTATTGGTTAAAAAATGAGCTGATTTAACAAAAATTTAA

CGCGAATTTTAACAAAATATTAACGCTTACAATTTCCA

TTCGCCATTCAGGCTGCGCAACTGTTGGGAAGGGCGATC

GGTGCGGGCCTCTTCGCTATTACGCCAGCTGGCGAAAG

GGGGATGTGCTGCAAGGCGATTAAGTTGGGTAACGCCAG

GGTTTTCCCAGTCACGACGTTGTAAAACGACGGCCAGT

GAATTGTAATACGACTCACTATAGGGCGAATTGGATCCG

ACCGCGAAGGTCAATGCCCCGTACATTCGCATTCGAGC

ACAGCAACTCTCCAAGAGTCGACAGTACATGTCCTGGAG

AAAGGAGCGGTGACAGTACACTTTAGCACCGCGAGTCC

ACAGGCGAACTTTATCGTATCGCTGTGTGGGCTAGTGGA

TCCGGAGTCTTATGCAATACTCTTGTAGTCTTGCAACA

TGGTAACGATGAGTTAGCAACATGCCTTACAAGGAGAGA

AAAAGCACCGTGCATGCCGATTGGTGGAAGTAAGGTGG

TACGATCGTGCCTTATTAGGAAGGCAACAGACGGGTCTG

ACATGGATTGGACGAACCACTGAATTCCGCATTGCAGA

GATATTGTATTTAAGTGCCTAGCTCGATACCGTCGAGAT

TGACGGCGTAGTACACACTATTGAATCAAACAGCCGAC

CAATTGCACTACCATCACAATGGAGAAGCCAGTAGTAAA

CGTAGACGTAGACCCCCAGAGTCCGTTTGTCGTGCAAC

TGCAAAAAAGCTTCCCGCAATTTGAGGTAGTAGCACAGC

AGGTCACTCCAAATGACCATGCTAATGCCAGAGCATTT

TCGCATCTGGCCAGTAAACTAATCGAGCTGGAGGTTCCT

ACCACAGCGACGATCTTGGACATAGGCAGCGCACCGGC

TCGTAGAATGTTTTCCGAGCACCAGTATCATTGTGTCTG

CCCCATGCGTAGTCCAGAAGACCCGGACCGCATGATGA

AATATGCCAGTAAACTGGCGGAAAAAGCGTGCAAGATTA

CAAACAAGAACTTGCATGAGAAGATTAAGGATCTCCGG

ACCGTACTTGATACGCCGGATGCTGAAACACCATCGCTC

TGCTTTCACAACGATGTTACCTGCAACATGCGTGCCGA

ATATTCCGTCATGCAGGACGTGTATATCAACGCTCCCGG

AACTATCTATCATCAGGCTATGAAAGGCGTGCGGACCC

TGTACTGGATTGGCTTCGACACCACCCAGTTCATGTTCT

CGGCTATGGCAGGTTCGTACCCTGCGTACAACACCAAC

TGGGCCGACGAGAAAGTCCTTGAAGCGCGTAACATCGGA

CTTTGCAGCACAAAGCTGAGTGAAGGTAGGACAGGAAA

ATTGTCGATAATGAGGAAGAAGGAGTTGAAGCCCGGGTC

GCGGGTTTATTTCTCCGTAGGATCGACACTTTATCCAG
```

-continued

AACACAGAGCCAGCTTGCAGAGCTGGCATCTTCCATCGG

TGTTCCACTTGAATGGAAAGCAGTCGTACACTTGCCGC

TGTGATACAGTGGTGAGTTGCGAAGGCTACGTAGTGAAG

AAAATCACCATCAGTCCCGGGATCACGGGAGAAACCGT

GGGATACGCGGTTACACACAATAGCGAGGGCTTCTTGCT

ATGCAAAGTTACTGACACAGTAAAAGGAGAACGGGTAT

CGTTCCCTGTGTGCACGTACATCCCGGCCACCATATGCG

ATCAGATGACTGGTATAATGGCCACGGATATATCACCT

GACGATGCACAAAAACTTCTGGTTGGGCTCAACCAGCGA

ATTGTCATTAACGGTAGGACTAACAGGAACACCAACAC

CATGCAAAATTACCTTCTGCCGATCATAGCACAAGGGTT

CAGCAAATGGGCTAAGGAGCGCAAGGATGATCTTGATA

ACGAGAAAATGCTGGGTACTAGAGAACGCAAGCTTACGT

ATGGCTGCTTGTGGGCGTTTCGCACTAAGAAAGTACAT

TCGTTTTATCGCCCACCTGGAACGCAGACCTGCGTAAAA

GTCCCAGCCTCTTTTAGCGCTTTTCCCATGTCGTCCGT

ATGGACGACCTCTTTGCCCATGTCGCTGAGGCAGAAATT

GAAACTGGCATTGCAACCAAAGAAGGAGGAAAAACTGC

TGCAGGTCTCGGAGGAATTAGTCATGGAGGCCAAGGCTG

CTTTTGAGGATGCTCAGGAGGAAGCCAGAGCGGAGAAG

CTCCGAGAAGCACTTCCACCATTAGTGGCAGACAAAGGC

ATCGAGGCAGCCGCAGAAGTTGTCTGCGAAGTGGAGGG

GCTCCAGGCGGACATCGGAGCAGCATTAGTTGAAACCCC

GCGCGGTCACGTAAGGATAATACCTCAAGCAAATGACC

GTATGATCGGACAGTATATCGTTGTCTCGCCAAACTCTG

TGCTGAAGAATGCCAAACTCGCACCAGCGCACCCGCTA

GCAGATCAGGTTAAGATCATAACACACTCCGGAAGATCA

GGAAGGTACGCGGTCGAACCATACGACGCTAAAGTACT

GATGCCAGCAGGAGGTGCCGTACCATGGCCAGAATTCCT

AGCACTGAGTGAGAGCGCCACGTTAGTGTACAACGAAA

GAGAGTTTGTGAACCGCAAACTATACCACATTGCCATGC

ATGGCCCCGCCAAGAATACAGAAGAGGAGCAGTACAAG

GTTACAAAGGCAGAGCTTGCAGAAACAGAGTACGTGTTT

GACGTGGACAAGAAGCGTTGCGTTAAGAAGGAAGAAGC

CTCAGGTCTGGTCCTCTCGGGAGAACTGACCAACCCTCC

CTATCATGAGCTAGCTCTGGAGGGACTGAAGACCCGAC

CTGCGGTCCCGTACAAGGTCGAAACAATAGGAGTGATAG

GCACACCGGGGTCGGGCAAGTCAGCTATTATCAAGTCA

ACTGTCACGGCACGAGATCTTGTTACCAGCGGAAAGAA

GAAAATTGTCGCGAAATTGAGGCCGACGTGCTAAGACT

GAGGGGTATGCAGATTACGTCGAAGACAGTAGATTCGGT

TATGCTCAACGGATGCCACAAAGCCGTAGAAGTGCTGT

ACGTTGACGAAGCGTTCGCGTGCCACGCAGGAGCACTAC

TTGCCTTGATTGCTATCGTCAGGCCCCGCAAGAAGGTA

GTACTATGCGGAGACCCCATGCAATGCGGATTCTTCAAC

ATGATGCAACTAAAGGTACATTTCAATCACCCTGAAAA

AGACATATGCACCAAGACATTCTACAAGTATATCTCCCG

GCGTTGCACACAGCCAGTTACAGCTATTGTATCGACAC

TGCATTACGATGGAAAGATGAAAACCACGAACCCGTGCA

AGAAGAACATTGAAATCGATATTACAGGGGCCACAAAG

CCGAAGCCAGGGGATATCATCCTGACATGTTTCCGCGGG

TGGGTTAAGCAATTGCAAATCGACTATCCCGGACATGA

AGTAATGACAGCCGCGGCCTCACAAGGGCTAACCAGAAA

AGGAGTGTATGCCGTCCGGCAAAAAGTCAATGAAAACC

CACTGTACGCGATCACATCAGAGCATGTGAACGTGTTGC

TCACCCGCACTGAGGACAGGCTAGTGTGGAAAACCTTG

CAGGGCGACCCATGGATTAAGCAGCTCACTAACATACCT

AAAGGAAACTTTCAGGCTACTATAGAGGACTGGGAAGC

TGAACACAAGGGAATAATTGCTGCAATAAACAGCCCCAC

TCCCCGTGCCAATCCGTTCAGCTGCAAGACCAACGTTT

GCTGGGCGAAAGCATTGGAACCGATACTAGCCACGGCCG

GTATCGTACTTACCGGTTGCCAGTGGAGCGAACTGTTC

CCACAGTTTGCGGATGACAAACCACATTCGGCCATTTAC

GCCTTAGACGTAATTTGCATTAAGTTTTTCGGCATGGA

CTTGACAAGCGGACTGTTTTCTAAACAGAGCATCCCACT

AACGTACCATCCCGCCGATTCAGCGAGGCCGGTAGCTC

ATTGGGACAACAGCCCAGGAACCCGCAAGTATGGGTACG

ATCACGCCATTGCCGCCGAACTCTCCCGTAGATTTCCG

GTGTTCCAGCTAGCTGGGAAGGGCACACAACTTGATTTG

CAGACGGGGAGAACCAGAGTTATCTCTGCACAGCATAA

CCTGGTCCCGGTGAACCGCAATCTTCCTCACGCCTTAGT

CCCCGAGTACAAGGAGAAGCAACCCGGCCCGGTCGAAA

AATTCTTGAACCAGTTCAAACACCACTCAGTACTTGTGG

TATCAGAGGAAAAATTGAAGCTCCCCGTAAGAGAATC

GAATGGATCGCCCCGATTGGCATAGCCGGTGCAGATAAG

AACTACAACCTGGCTTTCGGGTTTCCGCCGCAGGCACG

GTACGACCTGGTGTTCATCAACATTGGAACTAAATACAG

AAACCACCACTTTCAGCAGTGCGAAGACCATGCGGCGA

CCTTAAAAACCCTTTCGCGTTCGGCCCTGAATTGCCTTA

ACCCAGGAGGCACCCTCGTGGTGAAGTCCTATGGCTAC

GCCGACCGCAACAGTGAGGACGTAGTCACCGCTCTTGCC

-continued

AGAAAGTTTGTCAGGGTGTCTGCAGCGAGACCAGATTG

TGTCTCAAGCAATACAGAAATGTACCTGATTTTCCGACA

ACTAGACAACAGCCGTACACGGCAATTCACCCCGCACC

ATCTGAATTGCGTGATTTCGTCCGTGTATGAGGGTACAA

GAGATGGAGTTGGAGCCGCGCCGTCATACCGCACCAAA

AGGGAGAATATTGCTGACTGTCAAGAGGAAGCAGTTGTC

AACGCAGCCAATCCGCTGGGTAGACCAGGCGAAGGAGT

CTGCCGTGCCATCTATAAACGTTGGCCGACCAGTTTTAC

CGATTCAGCCACGGAGACAGGCACCGCAAGAATGACTG

TGTGCCTAGGAAAGAAAGT

The nucleic acid sequence may comprise a variant of SEQ ID NO: 6 which shares at least 70%, at least 75%, at least 80%, at least 85%, at least 90%, at least 95% or at least 99% sequence identity with SEQ ID NO: 6 and has a functional RdRp activity.

The amino acid sequence of the nsp1, nsp2, nsp3 and nsp4 polypeptides encoded by SEQ ID NO: 6 are shown as SEQ ID NO: 7-10, respectively.

SEQ ID NO: 7

MEKPVVNVDVDPQSPFVVQLQKSFPQFEVVAQQVTPNDHANARAFSHLAS

KLIELEVPTTATILDIGSAPARRMFSEHQYHCVCPMRSPEDPDRMMKYAS

KLAEKACKITNKNLHEKIKDLRTVLDTPDAETPSLCFHNDVTCNMRAEYS

VMQDVYINAPGTIYHQAMKGVRTLYWIGFDTTQFMFSAMAGSYPAYNTNW

ADEKVLEARNIGLCSTKLSEGRTGKLSIMRKKELKPGSRVYFSVGSTLYP

EHRASLQSWHLPSVFHLNGKQSYTCRCDTVVSCEGYVVKKITISPGITGE

TVGYAVTHNSEGFLLCKVTDTVKGERVSFPVCTYIPATICDQMTGIMATD

ISPDDAQKLLVGLNQRIVINGRTNRNTNTMQNYLLPIIAQGFSKWAKERK

DDLDNEKMLGTRERKLTYGCLWAFRTKKVHSFYRPPGTQTCVKVPASFSA

FPMSSVWTTSLPMSLRQKLKLALQPKKEEKLLQVSEELVMEAKAAFEDAQ

EEARAEKLREALPPLVADKGIEAAAEVVCEVEGLQADIGA

SEQ ID NO: 8

ALVETPRGHVRIIPQANDRMIGQYIVVSPNSVLKNAKLAPAHPLADQVKI

ITHSGRSGRYAVEPYDAKVLMPAGGAVPWPEFLALSESATLVYNEREFVN

RKLYHIAMHGPAKNTEEEQYKVTKAELAETEYVFDVDKKRCVKKEEASGL

VLSGELTNPPYHELALEGLKTRPAVPYKVETIGVIGTPGSGKSAIIKSTV

TARDLVTSGKKENCREIEADVLRLRGMQITSKTVDSVMLNGCHKAVEVLY

VDEAFACHAGALLALIAIVRPRKKVVLCGDPMQCGFFNMMQLKVHFNHPE

KDICTKTFYKYISRRCTQPVTAIVSTLHYDGKMKTTNPCKKNIEIDITGA

TKPKPGDIILTCFRGWVKQLQIDYPGHEVMTAAASQGLTRKGVYAVRQKV

NENPLYAITSEHVNVLLTRTEDRLVWKTLQGDPWIKQLTNIPKGNFQATI

EDWEAEHKGIIAAINSPTPRANPFSCKTNVCWAKALEPILATAGIVLTGC

QWSELFPQFADDKPHSAIYALDVICIKFFGMDLTSGLFSKQSIPLTYHPA

DSARPVAHWDNSPGTRKYGYDHAIAAELSRRFPVFQLAGKGTQLDLQTGR

-continued

TRVISAQHNLVPVNRNLPHALVPEYKEKQPGPVEKFLNQFKHHSVLVVSE

EKIEAPRKRIEWIAPIGIAGADKNYNLAFGFPPQARYDLVFINIGTKYRN

HHFQQCEDHAATLKTLSRSALNCLNPGGTLVVKSYGYADRNSEDVVTALA

RKFVRVSAARPDCVSSNTEMYLIFRQLDNSRTRQFTPHHLNCVISSVYEG

TRDGVGA

SEQ ID NO: 9

APSYRTKRENIADCQEEAVVNAANPLGRPGEGVCRAIYKRWPTSFTDSAT

ETGTARMTVCLGKKVIHAVGPDFRKHPEAEALKLLQNAYHAVADLVNEHN

IKSVAIPLLSTGIYAAGKDRLEVSLNCLTTALDRTDADVTIYCLDKKWKE

RIDAALQLKESVTELKDEDMEIDDELVWIHPDSCLKGRKGFSTTKGKLYS

YFEGTKFHQAAKDMAEIKVLFPNDQESNEQLCAYILGETMEAIREKCPVD

HNPSSSPPKTLPCLCMYAMTPERVHRLRSNNVKEVTVCSSTPLPKHKIKN

VQKVQCTKVVLFNPHTPAFVPARKYIEVPEQPTAPPAQAEEAPEVVATPS

PSTADNTSLDVTDISLDMDDSSEGSLFSSFSGSDNSITSMDSWSSGPSSL

EIVDRRQVVVADVHAVQEPAPIPPPRLKKMARLAAARKEPTPPASNSSES

LHLSFGGVSMSLGSIFDGETARQAAVQPLATGPTDVPMSFGSFSDGEIDE

LSRRVTESEPVLFGSFEPGEVNSIISSRSAVSFPLRKQRRRRRSRRTEY

SEQ ID NO: 10

LTGVGGYIFSTDTGPGHLQKKSVLQNQLTEPTLERNVLERIHAPVLDTSK

EEQLKLRYQMMPTEANKSRYQSRKVENQKAITTERLLSGLRLYNSATDQP

ECYKITYPKPLYSSSVPANYSDPQFAVAVCNNYLHENYPTVASYQITDEY

DAYLDMVDGTVACLDTATFCPAKLRSYPKKHEYRAPNIRSAVPSAMQNTL

QNVLIAATKRNCNVTQMRELPTLDSATFNVECFRKYACNDEYWEEFARKP

IRITTEFVTAYVARLKGPKAAALFAKTYNLVPLQEVPMDRFVMDMKRDVK

VTPGTKHTEERPKVQVIQAAEPLATAYLCGIHRELVRRLTAVLLPNIHTL

FDMSAEDFDAIIAEHFKQGDPVLETDIASFDKSQDDAMALTGLMILEDLG

VDQPLLDLIECAFGEISSTHLPTGTRFKFGAMMKSGMFLTLFVNTVLNVV

IASRVLEERLKTSRCAAFIGDDNIIHGVVSDKEMAERCATWLNMEVKIID

AVIGERPPYFCGGFILQDSVTSTACRVADPLKRLFKLGKPLPADDEQDED

RRRALLDETKAWFRVGITGTLAVAVTTRYEVDNITPVLLALRTFAQSKRA

FQAIRGEIKHLYGGPK

The nsp1-4 polypeptide may comprise an amino acid sequence shown as SEQ ID NO: 7-10.

The nsp1-4 polypeptide may comprise a variant of SEQ ID NO: 7-10 which retains the functional activity of the corresponding amino acid sequence shown as SEQ ID NO: 7-10.

The variant may comprise a sequence which shares at least 70%, at least 75%, at least 80%, at least 85%, at least 90%, at least 95% or at least 99% sequence identity with SEQ ID NO: 7 and retains the functional activity of the amino acid sequence shown as SEQ ID NO: 7.

The variant may comprise a sequence which shares at least 70%, at least 75%, at least 80%, at least 85%, at least 90%, at least 95% or at least 99% sequence identity with SEQ ID NO: 8 and retains the functional activity of the amino acid sequence shown as SEQ ID NO: 8.

The variant may comprise a sequence which shares at least 70%, at least 75%, at least 80%, at least 85%, at least 90%, at least 95% or at least 99% sequence identity with SEQ ID NO: 9 and retains the functional activity of the amino acid sequence shown as SEQ ID NO: 9.

The variant may comprise a sequence which shares at least 70%, at least 75%, at least 80%, at least 85%, at least 90%, at least 95% or at least 99% sequence identity with SEQ ID NO: 10 and retains the functional activity of the amino acid sequence shown as SEQ ID NO: 10.

The temperature sensitive RdRp may be derived from any RdRp as described herein. As used herein a "temperature sensitive RdRp" has a different level of activity at different temperatures. The term "term sensitive RdRp" as used herein may be synonymous with "thermolabile RdRp".

As used herein the term "RdRp activity" or the activity of the RdRp refers to the amount of RNA (e.g. the level or number of RNA transcripts) produced by the RdRp enzyme from an RNA template. The activity of an RdRp may be determined, for example, by measuring the amount of RNA produced from the RNA template during a given time period. The amount of RNA may be determined using standard techniques in the art (e.g. RT-PCR or RT-qPCR). Suitably, the activity of an RdRp may be determined by measuring the level of protein produced from the RNA template. The level of protein may be measured by determining, for example, the expression of a reporter gene such as a fluorescent protein (e.g. GFP) using standard techniques in the art (e.g. flow cytometry).

As will be apparent, the level of RNA produced from an RNA template by the RdRp enzyme should be determined using a suitable assay in which all conditions, other than temperature, are kept the same.

An RdRp with high activity will produce more RNA from an RNA template, and provide higher levels of protein expression from an RNA template, than an RdRp with low activity. An RdRp with high activity may have for example 5, 6, 7, 8, 9, 10, 25, 50, 100, 250, 500, 750, 1000, 2500, 5000, 7500, 10000 or 15000 fold more activity than an RdRp with low activity.

By way of example, the temperature sensitive RdRp may have a higher level activity at temperatures below 35° C. compared to temperatures above 35° C. For example, the RdRp may have a higher level of activity from about 25° C. to about 29° C. compared to from about 35° C. to about 38° C. For example, RdRp may be inactive at temperatures of greater than 35° C. In one embodiment, the RdRp may have an optimal activity at 29° C. and be inactive at 37° C.

Figure 8:
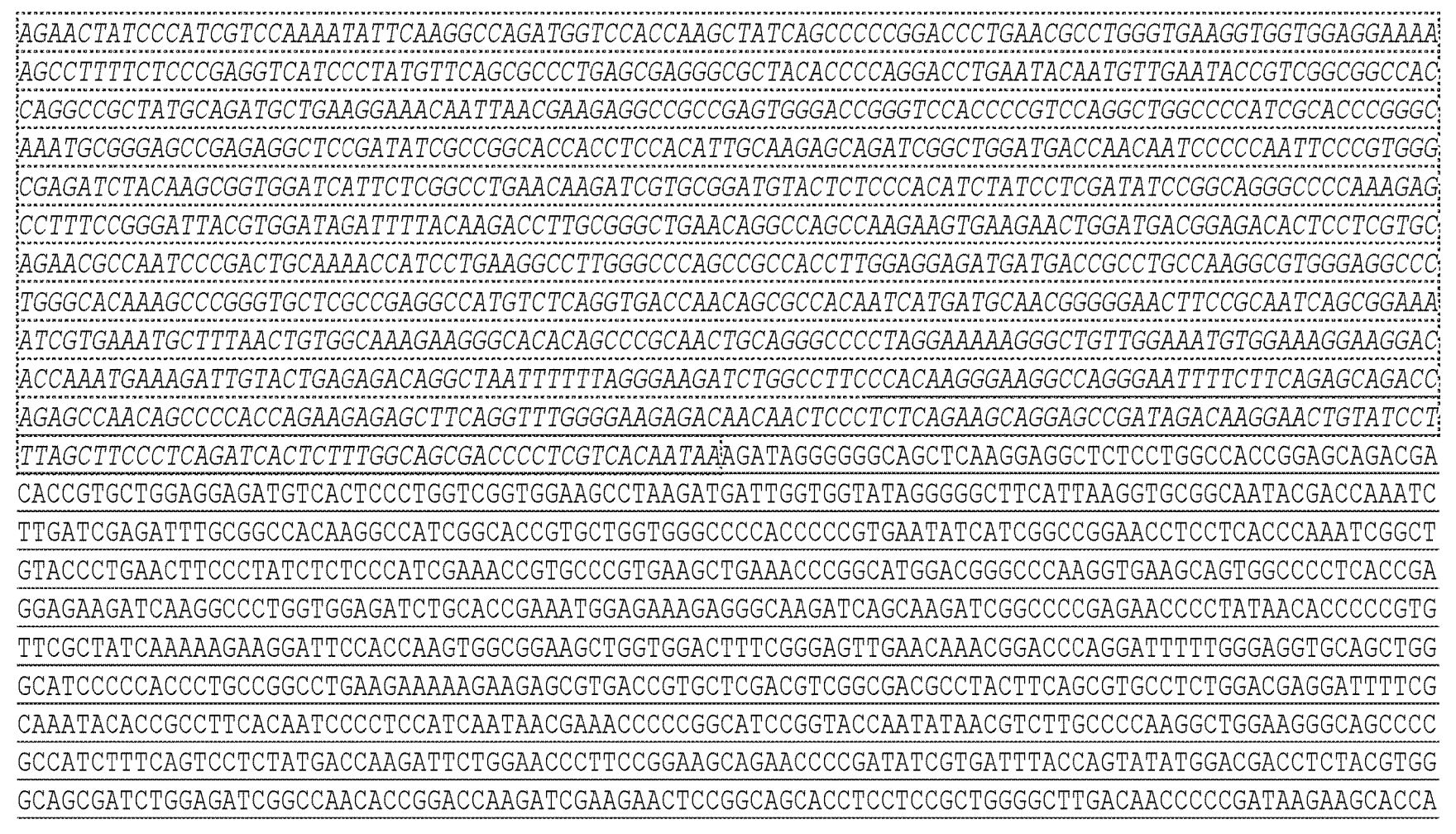
Figure 8:
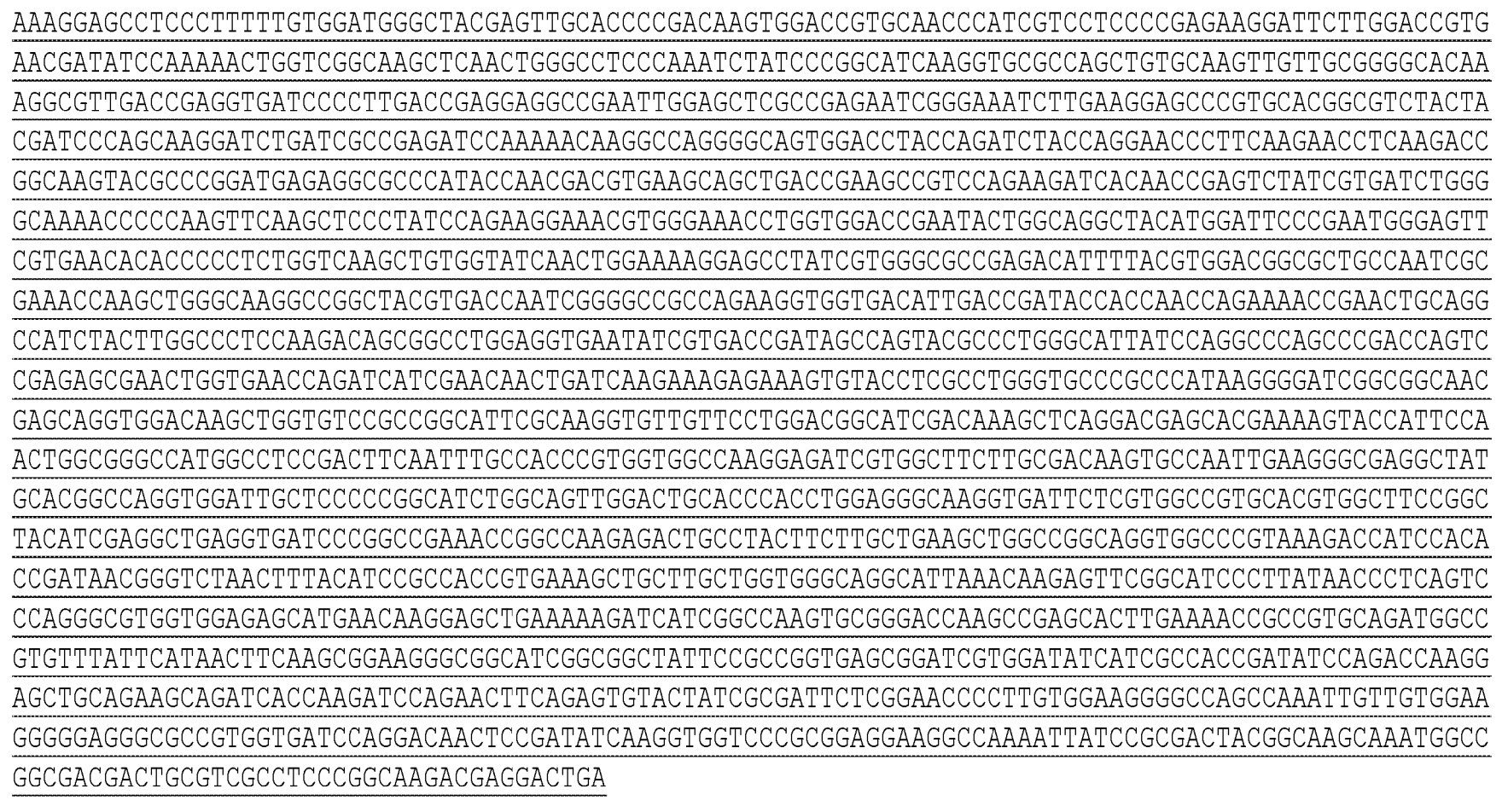

An example of such a temperature sensitive RdRp is provided by Boorsma et al. (Nature Biotechnology; 2000; vol 18; 419-432). The temperature sensitive RdRp may comprise a G to E mutation at position 153 (G153E) of the sequence shown as SEQ ID NO: 10. The temperature sensitive RdRp may further comprise a P to S mutation at position 726 (P276S) of the sequence shown as SEQ ID NO: 8. An example of such a temperature sensitive RdRp is shown as SEQ ID NO: 2 (see FIG. 8).

A temperature sensitive variant may be identified in nature (e.g. Burge J Virol. 1967 October; 1(5):956-62.). Alternatively, virus can be subjected to multiple rounds of random mutagenesis and clones screened for inability to replicate at higher temperatures. Finally, directed mutagenesis of the polymerase can be made from predicted structural information and known mutations to reduce thermostability in related enzymes.

The present inventors have demonstrated for the first time that surprisingly, a temperature sensitive RdRp may be used in a retroviral system. It is demonstrated herein that high titres of a functional virus can be produced by packaging cells at a low temperature using a temperature sensitive RdRp retroviral system.

The use of a temperature sensitive RdRp provides a particular advantage as it enables toxic retroviral proteins, such as gagpol and env proteins, to be induced in a controllable manner. In particular, if such toxic proteins are transcribed from a vector, or a packaging cell or producer cell genome under the control of a RdRp subgenomic promoter, translation of toxic proteins can be prevented by culturing the packaging cell or producer cell of the present invention at a temperature at which the temperature sensitive RdRp is inactive. At a chosen time point, for example once the cells are confluent, the temperature of the culture can be altered to a temperature at which the RdRp is active, which causes the production of large amounts of mRNA encoding, for example toxic gagpol or env protein. This is still ultimately toxic to the producer cell—but at this stage large amounts of producer cells are present and large amount of virus are produced and the cultures are terminated.

Retrovirus

The packaging cell and producer cells of the present invention may be used to produce retroviral vectors.

The concept of using viral vectors for gene therapy is well known (Verma and Somia (1997) Nature 389:239-242). As used herein the term "retroviral vector", when referring to a retroviral vector system also includes a retroviral vector particle capable of transducing a recipient cell with a nucleotide sequence of interest (NOI).

A retroviral vector particle includes the following components: a vector genome (retrovirus nucleic acid transgene construct), which contains one or more NOIs, a nucleocapsid encapsidating the nucleic acid, and a membrane surrounding the nucleocapsid.

The term "nucleocapsid" refers to at least the group of specific viral core proteins (gag) and the viral polymerase (pol) of a retrovirus genome. These proteins encapsidate the packagable sequences and are themselves further surrounded by a membrane containing an envelope glycoprotein.

The term "retrovirus nucleic acid transgene construct" refers to both to the RNA construct present in the retroviral vector particle and the integrated DNA construct. The term also embraces a separate or isolated DNA construct capable of encoding such an RNA genome. A retroviral genome should comprise at least one component part derivable from a retrovirus. The term "derivable" is used in its normal sense as meaning a nucleotide sequence or a part thereof which need not necessarily be obtained from a virus such as a lentivirus but instead could be derived therefrom. By way of example, the sequence may be prepared synthetically or by use of recombinant DNA techniques.

There are many retroviruses. For the present application, the term "retrovirus" includes, but is not limited to: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

In a preferred embodiment, the retroviral vector is derivable from a lentivirus.

Lentiviral vectors are major tools for gene delivery, providing efficient transduction of a wide variety cell types such as hematopoietic stem cells, neurons and endothelial cells. The advantages of lentiviral vectors over other systems are the ability to infect both dividing and non-dividing cells in vivo and in vitro and their greater packaging capacity that enables the expression of larger RNA transcripts.

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Details of HIV variants may also be found in the Los Alamos National Laboratory variants database. Details of EIAV variants may be found through the U.S. National Library of Medicine.

Lentiviruses have three main genes coding for the viral proteins in the order: 5'-gag-pol-env-3'. There are two regulatory genes, tat and rev. There are additional accessory genes depending on the virus (e.g., for HIV-1: vif, vpr, vpu, nef) whose products are involved in regulation of synthesis and processing viral RNA and other replicative functions. The Long terminal repeat (LTR) is about 600 nt long, of which the U3 region is 450, the R sequence 100 and the U5 region some 70 nt long. The LTR contains regulatory signals including transcriptional control elements, polyadenylation signals and sequences needed for replication and the integration of the viral genome.

Viral proteins involved in early stages of replication include Reverse Transcriptase and Integrase. Reverse Transcriptase is the virally encoded RNA-dependent DNA polymerase. The enzyme uses the viral RNA genome as a template for the synthesis of a complementary DNA copy. Reverse transcriptase also has RNaseH activity for destruction of the RNA-template. Integrase binds both the viral cDNA generated by reverse transcriptase and the host DNA.

Integrase processes the LTR before inserting the viral genome into the host DNA. Tat acts as a trans-activator during transcription to enhance initiation and elongation. The Rev responsive element acts post-transcriptionally, regulating mRNA splicing and transport to the cytoplasm.

Retrovirus Nucleic Acid Transfer Vector

In one embodiment, the present invention provides a retrovirus producer cell which is a packaging cell according to the first aspect of the present invention, further comprising a retrovirus nucleic acid transfer vector (and/or envelope or gagpol expression cassettes). The retrovirus nucleic acid transfer vector and/or envelope or gagpol expression cassettes may contain a RdRp subgenomic promoter element or elements. Thus, upon nuclear export of the transcribed retroviral components, the RdRp replicates them in the cytoplasm of the cell.

This strategy enables the RdRp to replicate and therefore amplify the transfer vector in the cytoplasm of the cell. Such cytoplasmic amplification means that nuclear export of long, complex transfer vector transgenes is no longer a limiting factor on the lentiviral titre.

Thus in one embodiment the retrovirus transfer vector comprises at least one RdRp promoter element, which promoter element(s) enables at least part of the retroviral nucleic acid transfer vector to be replicated by the RdRp. In one aspect the RdRp promoter element is operably linked to at least part of the retroviral nucleic acid transfer vector to be replicated by the RdRp.

In particular, the RdRp promoter element(s) enable retroviral components (e.g. env, gag and/or pol) or the nucleotide sequence of interest to be replicated by the RdRp.

Thus in one embodiment the retrovirus transfer vector comprises at least one RdRP promoter element, which promoter element(s) enables the retroviral nucleic acid transfer vector to be replicated by the RdRp.

The RdRp promoter element may be a PSG, rPSG or iPSG element as defined herein.

In one embodiment, the inclusion of RdRp promoters, e.g. subgenomic RdRp promoters in proximity to both the 5' and 3' end of the retroviral nucleic acid transfer vector allows it to be exponentially amplified in the cytoplasm by the RdRp via an intermediate anti-sense strand.

In one embodiment the retroviral nucleic acid transfer vector comprises the following structure:

$$5'\text{P1-rPSG-}^5\text{dLTR-P2-NOI-}^3\text{dLTR-PSG3'}$$

in which

P1 is a eukaryotic promoter which drives transcription rPSG is a sequence which acts as a negative sense sub-genomic promoter for the RdRp when at the 3' end of the negative sense strand;

$^5$dLTR is a truncated 5' retrovirus long terminal repeat where the U3 region is non-functioning P2 is a eukaryotic promoter which drives expression of the NOI;

NOI is a nucleotide sequence of interest;

$^3$dLTR is a self-inactivating 3' retrovirus long terminal repeat with a non-functioning U3;

PSG is a sequence which acts as a sub-genomic promoter for RdRp as a positive sense.

Suitably, the 5'LTR and/or the 3'LTR has been modified. Modification of the 3'LTR can be used to render the virus replication-defective, that is to say that the virus is not capable of complete replication such that infective virions are not produced. In other words, the modified LTR is non-functioning.

For example the U3 region may be a modified to a non-functional U3 region. The U3 region may be modified e.g. by deletion, truncation, substitution or insertion.

The U3 region may be modified by replacing the U3 region with a heterologous promoter to drive transcription of the viral genome during production of viral particles.

The LTR may be a modified e.g. by deletion, truncation, substitution or insertion. The 3' retrovirus long terminal repeat may be truncated or deleted.

"Non-functioning" as used herein with respect to the U3 region means that the 3'LTR cannot be used as a template for the 5' LTR U3 region during viral replication therefore the viral transcript cannot be made. The U3 region contains the enhancer and promoter elements.

"Self inactivating" (SIN) vectors refer to replication-defective vectors in which the U3 is non-functioning. The 3'LTR U3 region may be modified e.g. by deletion, truncation, mutation or substitution to prevent viral transcription beyond the first round of viral replication, ending the life cycle of the virus. The vector is able to infect and integrate into the host genome only once.

In some embodiments, the 5' LTR U3 promoter region is non-functioning e.g. by deletion, truncation, substitution or insertion and the rPSG is placed upstream of the 5'LTR R region.

In one embodiment, the 5' LTR U3 promoter region is deleted and the rPSG is placed upstream of the 5'LTR R region.

In some embodiments the 3'LTR U5 region is non-functioning e.g. by deletion, truncation, substitution or insertion so the vector is self-inactivating (SIN) and the PSG sequences integrated into the U5 region.

In one embodiment, the 3'LTR U5 region is deleted or truncated.

In some embodiments, the 5' LTR U3 promoter region is non-functioning e.g. by deletion, truncation, substitution or insertion, the rPSG is placed upstream of the 5'LTR R region and the 3'LTR U5 region is non-functioning e.g. by deletion, truncation, substitution or insertion.

In some embodiments, the 5' LTR U3 promoter region is deleted, the rPSG is placed upstream of the 5'LTR R region and the 3'LTR U5 region is deleted or truncated.

The retrovirus nucleic acid transfer vector structure above is shown in the context of a positive sense RNA strand. Positive sense RNA refers to a nucleic acid sequence which is translated or translatable into protein.

Recognition sequences which enable the replication of a RNA template by RdRp are known in the art. By way of example, sequences from Sindbis virus are described herein. FIG. 1 shows the life-cycle of the Sindbis virus genome.

Briefly, the positive sense RNA genome (the retrovirus transfer vector described herein is also positive sense RNA) is recognized by RdRp at the 3' CSE (conserved sequence element). The poly-A tail may also be needed for recognition. The combination of the poly-A tail and the 3' CSE is hence a PSG which acts at the extreme 3' of a RNA template. The action of RdRp on this template leads to a negative sense RNA strand. The positive sense RNA strand reverse CAP/5'UTR and a 5'CSE are now reverse complement at the 3' end of the negative sense RNA strand. These are now recognized by the RdRp and result in the rPSG which acts at the 5' end of a transcript. Recognition of this sequence leads to replication of the negative strand back to positive. An additional sequence is also present inside the Sindbis genome. This sequence is termed the "sub-genomic promoter" and is also recognized by the polymerase when in the negative sense. This generates a shorter species of sense RNA (Thal, M. A. et al. Virology 358, 221-232 (2007)).

A "promoter" as used herein refers to a recognition site of a polynucleotide (DNA or RNA) to which an RNA polymerase binds. An RNA polymerase initiates and transcribes polynucleotides operably linked to the promoter.

"Operably linked" as used herein means that there is a functional linkage between a nucleic acid expression control sequence (e.g. a promoter and/or enhancer) and a second polynucleotide sequence.

Illustrative sequences are detailed in the figures and are also provided by the canonical sequence of the Sindbis virus (NCBI Reference Sequence: NC_001547.1, and summarized in the table below.

| Region | Function | Nt position |
|---|---|---|
| 5'UTR + 5'CSE | Primes full-length anti-sense as template | 1-425 |
| Sub-genomic promoter | Primes internal anti-sense as template | 7300-7646 |
| 3'CSE | Primes amplification sense as template | 11350-11703 |

Thus, a PSG is a nucleic acid sequence which enables the 3' to 5' replication of the retrovirus nucleic acid transfer vector by a RdRp as described herein.

The PSG sequence may comprise the sequence shown as SEQ ID NO: 11.

-Sindbis 3'CSE (PSG)

SEQ ID NO: 11

CTTGCAGCATGATGCTGACTAGCACACGAAGATGACCGCTACGCCCCAAT

GATCCGACCAGCAAAACTCGATGTACTTCCGAGGAACTGATGTGCATAAT

GCATCAGGCTGGTACATTAGATCCCCGCTTACCGCGGGCAATATAGCAAC

ACTAAAAACTCGATGTACTTCCGAGGAAGCGCAGTGCATAATGCTGCGCA

GTGTTGCCACATAACCACTATATTAACCATTTATCTAGCGGACGCCAAAA

ACTCAATGTATTTCTGAGGAAGCGTGGTGCATAATGCCACGCAGCGTCTG

CATAACTTTTATTATTTCTTTTATTAATCAACAAAATTTTGTTTTTAACA

TTTC

The PSG sequence may comprise a variant which shares at least 80%, at least 85%, at least 90%, at least 95%, or at least 99% sequence identity with SEQ ID NO: 11 and retains the ability to recruit an RdRp.

The PSG sequence may comprise a truncated version of SEQ ID NO: 11 or truncated version of a variant of SEQ ID NO: 11 which retains ability to recruit a RdRp.

Accordingly, the RdRp expressed in a packaging/producer cell of the present invention replicates the positive sense retrovirus nucleic acid transfer vector structure described above from the PSG sequence in a 3' to 5' direction and thus generates a corresponding, complementary negative sense RNA strand.

rPSG is a reverse-orientation promoter for the RdRp. Positive to negative strand replication of the nucleic acid transfer vector as described above results in the generation of a negative strand copy of the nucleic acid transfer vector structure in which the rPSG is now in the correct orientation to recruit RdRp to replicate the negative sense nucleic acid transfer vector structure in the 3' to 5' direction. This second stage of replication (from negative sense to positive sense) results in the generation of a new copy of the positive sense nucleic acid transfer vector.

By way of example, the rPSG sequence may comprise the sequence shown as SEQ ID NO: 12.

-5'UTR + 5'CSE (rPSG)

SEQ ID NO: 12

ATTGACGGCGTAGTACACACTATTGAATCAAACAGCCGACCAATTGCACT

ACCATCACAATGGAGAAGCCAGTAGTAAACGTAGACGTAGACCCCCAGAG

TCCGTTTGTCGTGCAACTGCAAAAAAGCTTCCCGCAATTTGAGGTAGTAG

CACAGCAGGTCACTCCAAATGACCATGCTAATGCCAGAGCATTTTCGCAT

CTGGCCAGTAAACTAATCGAGCTGGAGGTTCCTACCACAGCGACGATCTT

GGACATAGGCAGCGCACCGGCTCGTAGAATGTTTTCCGAGCACCAGTATC

-continued

```
ATTGTGTCTGCCCCATGCGTAGTCCAGAAGACCCGGACCGCATGATGAAA

TACGCCAGTAAACTGGCGGAAAAAGCGTGCAAGATTACAAACAAGAACTT

GCATGAGAAGATTAAGGATCTCCGG
```

The rPSG sequence may comprise a variant which shares at least 80%, at least 85%, at least 90%, at least 95%, or at least 99% sequence identity with SEQ ID NO: 12 and retains the ability to recruit an RdRp.

The rPSG sequence may comprise a truncated version of SEQ ID NO: 12 or truncated version of a variant of SEQ ID NO: 12 which retains ability to recruit a RdRp.

"P1" may be any eukaryotic promoter which is capable of driving expression of the NOI within a host cell to be transduced with the retroviral vector. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus (RSV). A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

"P2" may be any eukaryotic promoter suitable for expression of the NOI and its selection depends on the application of the vector.

The "NOI" may be any nucleic acid sequence of interest to be expressed in a target host cell. For example, the NOI may encode a therapeutic protein such as a chimeric antigen receptor (CAR) or a missing gene in monogenic disorder.

Retroviral Helper Element Nucleotide Sequences

In another embodiment present invention may improve vector production by enabling retroviral proteins to be expressed at high level. This is useful since high levels of viral proteins are needed to facilitate a high viral titre.

In this embodiment the retrovirus packaging cell or producer cell according to the present invention comprises a retroviral helper element nucleotide sequence comprising (i) a nucleic acid sequence which encodes a retrovirus protein and (ii) a RdRp promoter element(s) which enables the nucleic acid sequence which encodes the retrovirus protein to be replicated by the RdRp. In one aspect the RdRp promoter element(s) are operably linked to the nucleic acid sequence which encodes the retrovirus protein to be replicated by the RdRp.

The RdRp promoter element may be a PSG, rPSG or iPSG element as defined herein.

As used herein, the terms PSG and rPSG may be referred to as a promoter for RdRp or a sub-genomic promoter for RdRp.

In one embodiment, the inclusion of an RdRp promoter or promoters at both the 5' and 3' end of the retroviral helper element nucleotide sequence allows the nucleic acid sequence which encodes the retroviral protein to be exponentially amplified in the cytoplasm by the RdRp.

In one embodiment the retroviral helper element nucleotide sequence comprises the following structure:

5'P-rPSG-RetroP-PSG3' in which

P is a eukaryotic promoter;

rPSG is a sequence which acts as a negative sense sub-genomic promoter for the RdRp when at the 3' end of the negative sense strand;

RetroP is nucleic acid sequence which encodes a retrovirus protein; and

PSG is a sequence which acts as a sub-genomic promoter for RdRp as positive sense.

In one embodiment the packaging cell or producer cell or the present invention comprises a retroviral helper element nucleotide sequence and a temperature sensitive RdRp as described herein. The use of a temperature sensitive RdRp enables the expression of the toxic retroviral proteins to be induced in a controllable manner (e.g. following a reduction in the temperature at which the packaging cell or producer cell is cultured).

Translation of toxic retroviral proteins can therefore be prevented, for example, until producer cell cultures are confluent. At this point the temperature of the culture can be altered, which causes the production of large amounts of mRNA. This is still ultimately toxic to the producer cell— but at this stage large amounts of producer cells are present and large amount of virus are produced and the cultures are terminated.

The retroviral helper element nucleotide sequence may have the following structure:

5'P-rPSG-rRetroP-PSG3' in which

P is a eukaryotic promoter;

rPSG is a sequence which acts as a negative sense sub-genomic promoter for the RdRp when at the 3' end of the negative sense strand rRetroP is nucleic acid sequence which encodes a retrovirus protein in reverse orientation PSG is a sequence which acts as a sub-genomic promoter for RdRp as a positive sense.

In this configuration, without activity of the RdRP, only negative-sense of the retroviral protein is generated. This cannot be translated. Upon altering cell culture temperature, RdRp is active and the transcript is amplified. Amplification results in a negative sense strand which now has a positive sense of the open-reading frame which can now be translated. This configuration allows amplification of retroviral protein transcript which can only be translated upon activation of RdRp solving the problems of having high levels of protein but only when viral production is needed.

In another embodiment, the retroviral helper element nucleotide sequence may have the following structure:

5'P-MG-STOP-iPSG-RetroP-PSG3' in which

P is a eukaryotic promoter;

MG is an open reading frame of a non-toxic marker gene

STOP is a stop signal or a series of stop signals iPSG is a reverse-orientation RdPg sub-genomic promoter which works internally RetroP is nucleic acid sequence which encodes a retrovirus protein; and PSG is a sequence which acts as a sub-genomic promoter for RdRp as a positive sense.

In this configuration, without RdRp activity, a transcript is generated which only translates to a marker gene since the ribosome is instructed to disengage from the transcript due to the stop signals after the marker gene reading frame. Upon RdRp activation, a shorter transcript is generated from the internal subgenomic promoter (iPSG). This shorter transcript lacks the marker gene and its stop signals, so the retroviral element can be translated. This has the advantage that the marker gene is constitutively expressed, allowing easy determination that stable integration of the cassette has occurred; however the retroviral protein is inducible upon RdRp activation avoiding basal toxicity.

A possible sequence for iPSG is SEQ ID NO: 13.

-sub-genomic promoter for RdRp which acts
internally (iPSG)
SEQ ID NO: 13
AAGATTCGGTTACTTCCACAGCGTGCCGCGTGGCGGATCCCCTGAAAAGG

CTGTTTAAGTTGGGTAAACCGCTCCCAGCCGACGACGAGCAAGACGAAGA

CAGAAGACGCGCTCTGCTAGATGAAACAAAGGCGTGGTTTAGAGTAGGTA

TAACAGGCACTTTAGCAGTGGCCGTGACGACCCGGTATGAGGTAGACAAT

ATTACACCTGTCCTACTGGCATTGAGAACTTTTGCCCAGAGCAAAAGAGC

ATTCCAAGCCATCAGAGGGGAAATAAAGCATCTCTACGGTGGTCCTAAAT

AGTCAGCATAGTACATTTCATCTGACTAATACTACAACACCACCACC

The iPSG sequence may comprise a variant which shares at least 80%, at least 85%, at least 90%, at least 95%, or at least 99% sequence identity with SEQ ID NO: 13 and retains the ability to recruit an RdRp.

The iPSG sequence may comprise a truncated version of SEQ ID NO: 13 or truncated version of a variant of SEQ ID NO: 13 which retains ability to recruit a RdRp.

The helper element nucleic acid sequence may further comprise a nucleic acid sequence between the iPSG and RetroP which enables the retroviral protein to be translated from the corresponding nucleic acid sequence. Such nucleic acid sequences are well known in the art. For example, the nucleic acid sequence may be a Kozak sequence. In one aspect the further nucleic acid sequence may be operably linked to the nucleic acid sequence which encodes the retroviral protein.

In this embodiment, a useful marker gene is the first open-reading frame on the transcript. A stop signal follows this frame, next is the internal sub-genomic promoter and the retroviral protein follows this. Now, without RdRp activity, the marker gene is translated, but the stop signal prevents the retroviral protein from being translated. When RdRp becomes active, the subgenomic promoter acts to generate a shorter transcript without the marker gene and stop signal. This short transcript is greatly amplified and further can now be translated. This configuration results in a system where at the ground state i.e. when RdRp is inactive or has low activity, only a useful marker gene is expressed, and the toxic retroviral protein is not expressed but when RdRp is activated or has high activity, a large amount of retroviral protein is generated.

Suitable stop signals are stop codons such as TGA or TAA or TAG. To reduce ribosomal read-through, a series of stop codons can be used. For example, at least 2, 3, 4, 5, 6, 7, 8, 9 or 10 stop codons may be used.

The marker gene may encode a detectable marker protein. The detectable marker may be any protein where the expression level can be determined, for example at the single cell level. In particular, the detectable marker may be detected without disrupting the cell.

For example, the detectable marker may be a fluorescent protein or a cell surface protein.

The expression level of the detectable marker may be determined using flow cytometry. Methods for using techniques such as flow cytometry to determine the expression levels of proteins are well known in the art. As such, the detectable marker may be a cell surface protein which can be detected using flow cytometry by using a reagent(s) which allows expression of the cell surface protein to be determined. For example, the reagent may be an antibody, for example a labelled antibody such as a fluorescently labelled antibody which specifically binds the cell surface protein. The detectable marker may be a fluorescent protein which is inherently detectable by flow cytometry due to its fluorescent characteristics.

In another embodiment, the retroviral helper element nucleotide sequence may have the following structure:

5'P-rPSG-MG-STOP-iPSG-RetroP-PSG3' in which
P is a eukaryotic promoter;
rPSG is a sequence which acts as a negative sense sub-genomic promoter for the RdRp when at the 3' end of the negative sense strand
MG is an open reading frame of a non-toxic marker gene
STOP is a stop signal or a series of stop signals
iPSG is a reverse-orientation RdPg sub-genomic promoter which works internally
RetroP is nucleic acid sequence which encodes a retrovirus protein; and
PSG is a sequence which acts as a sub-genomic promoter for RdRp as a positive sense This embodiment has the additional property that the entire transcript is exponentially amplified by RdRp via the PSG and rPSG sub-genomic promoter elements, with additional amplification from the internal sub-genomic promoter leading to higher levels of retroviral protein. This configuration most closely resembles the natural viral configuration.

Cell Surface Protein

In one embodiment the detectable marker is a cell surface protein. The cell surface protein may be any cell surface protein which is not natively expressed on the surface of the cell type which is used as the packaging cell or producer cell.

A cell surface protein typically comprises a membrane targeting domain and an extracellular domain. When expressed at the cell surface at least one domain of the cell surface protein is exoplasmic (i.e. on the exterior of the cell). This domain of the cell surface protein is therefore accessible for antibody binding.

In a preferred embodiment the cell surface protein is less than 200 amino acids in length. The use of a cell surface protein of less than 200 amino acids is advantageous because the smaller nucleic acid sequences which encode such proteins are easier to transfect and stably integrate into cells.

In one embodiment, the detectable marker is not an antibiotic resistance marker.

Retroviral Protein

The retroviral protein may be Gag, Pol, Env or Rev.

Group-specific antigen (gag) proteins are major components of the viral capsid, which are about 2000-4000 copies per virion. Pol proteins are responsible for synthesis of viral DNA and integration into host DNA after infection. Env proteins play a role in association and entry of virions into the host cell. A functional copy of an env gene is what makes retroviruses distinct from retroelements. The ability of the retrovirus to bind to its target host cell using specific cell-surface receptors is given by the surface component (SU) of the Env protein, while the ability of the retrovirus to enter the cell via membrane fusion is imparted by the membrane-anchored trans-membrane component (TM). Thus the Env protein is what enables the retrovirus to be infectious.

The retroviral protein may be gagpol. The nucleic acid sequence which encodes gagpol may comprise the nucleic acid sequence shown as SEQ ID NO: 5. The nucleic acid sequence which encodes gagpol may comprise a variant of SEQ ID NO: 5 which shares at least 70%, at least 75%, at least 80%, at least 85%, at least 90%, at least 95% or at least 99% sequence identity to SEQ ID NO: 4 and encodes functional Gag and Pol proteins.

The retroviral env protein may be the RD114 SU or TM protein or the RDPRO SU or TM protein.

In one embodiment, the env protein is VSV-G (glycoprotein G of the Vesicular stomatitis virus (VSV)). VSV-G is a commonly used env protein for lentiviral pseudotyping as it is capable of transducing all cell types.

The retroviral env protein may comprise the sequence shown as SEQ ID NO: 4. The retroviral env protein may comprise a variant of SEQ ID NO: 4 which retains ability to provide a functional env protein. The variant may share at least 70%, at least 75%, at least 80%, at least 85%, at least 90%, at least 95% or at least 99% sequence identity to SEQ ID NO: 4. 'Retroviral envelope protein' refers to the SU and/or TM proteins, as described above in relation to lentiviruses.

In one embodiment the packaging or producer cell is used to produce a lentivirus vector and the retroviral protein may be Rev. Rev is specifically expressed by lentivirus and acts post-transcriptionally, regulating mRNA splicing and transport to the cytoplasm.

Transposon Element

The nucleic acid transfer vector and/or the retroviral helper element nucleotide sequence encoding a retroviral protein may be stably integrated into the packaging cell or producer cell of the present invention.

Stable insertions into a cell line genome may be achieved using a variety of methods which are known in the art. For example, stable insertion may be achieved by transposition, transfection and selection or targeted insertion using genome editing tools.

The nucleic acid transfer vector and/or the retroviral helper element nucleotide sequence encoding a retroviral protein may be stably integrated into the packaging cell or producer cell of the present invention using any method known in the art including those listed above.

In one embodiment the nucleic acid transfer vector and/or the retroviral helper element nucleotide sequence encoding a retroviral protein is stably integrated into the packaging cell or producer cell of the present invention by transposition.

In one embodiment, stable integration is achieved by the use of transposon elements. The transposon elements may flank the nucleic acid sequence to be stably inserted into the genome of the packaging cell or producer cell.

Various transposon elements are well known in the art. Any suitable transposon may be used in the present invention.

The transposition process is catalysed by the transposase, and can be divided into four steps: (i) the transposase recognizes and binds to the ends of the transposon; (ii) the transposase and two transposon ends form a complex called synaptic or paired end complex; (iii) the transposon is excised from the donor site; and (iv) the excised transposon is transferred to a new location by the transposase.

In one embodiment of the invention, the transposon element or sequence comprises (or consists of) a piggyBac transposon. The piggyBac (PB) transposon was isolated from the cabbage looper moth, Trichoplusiani, and is recognized as one of the most efficient DNA transposons currently available for manipulating mammalian genomes. It is a mobile genetic element that can efficiently transpose between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and integrates them into TTAA chromosomal sites.

Unique features of PiggyBac transposons are that there is relatively no cargo limit as it can carry a transgene of up to 14 kbp and it is also reversible: genomes containing an inserted PiggyBac vector can be transiently re-transfected with the PB tranposase expression vector and the transposase will remove the transposons from the genome, footprint-free. More importantly, PB has been found capable of mediating stable integration of up to 4 independent transposons simultaneously in human cells following a single transfection.

An example of 5' and 3' PB transposon sequence are shown as SEQ ID NO: 14 and SEQ ID NO: 15

```
-PiggyBAC 5' Terminal Repeat
                                          SEQ ID NO 14
CATTCTAGATTAACCCTAGAAAGATAGTCTGCGTAAAATTGACGCATGCA

TTCTTGAAATATTGCTCTCTCTTTCTAAATAGCGCGAATCCGTCGCTGTG

CATTTAGGACATCTCAGTCGCCGCTTGGAGCTCCCGTGAGGCGTGCTTGT

CAATGCGGTAAGTGTCACTGATTTTGAACTATAACGACCGCGTGAGTCAA

AATGACGCATGATTATCTTTTACGTGACTTTTAAGATTTAACTCATACGA

TAATTATATTGTTATTTCATGTTCTACTTACGTGATAACTTATTATATAT

ATATTTTCTTGTTATAGATATCAACTAGAATGCTAGCATGGGCCCAT

-PiggyBAC 3' Terminal Repeat
                                          SEQ ID NO 15
AGTTTTGTTACTTTATAGAAGAAATTTTGAGTTTTTGTTTTTTTTTAATA

AATAAATAAACATAAATAAATTGTTTGTTGAATTTATTATTAGTATGTAA

GTGTAAATATAATAAAACTTAATATCTATTCAAATTAATAAATAAACCTC

GATATACAGACCGATAAAACACATGCGTCAATTTTACGCATGATTATCTT

TAACGTACGTCACAATATGATTATCTTTCTAGGGTTAATCTAG
```

In one embodiment, the nucleic acid construct may comprise a PiggyBAC 5' terminal repeat and a PiggyBAC 3' terminal repeat such that the construct can insert into the host genome. The PiggyBAC 5' and 3' terminal repeats may flank the sequence which is to be inserted into the host genome.

The PiggyBAC 5' Terminal Repeat may comprise or consist of a variant which shares at least 80%, at least 85%, at least 90%, at least 95%, or at least 99% sequence identity with SEQ ID NO: 14 and retains the ability to recruit an RdRp. The PiggyBAC 5' Terminal Repeat may comprise or consist of SEQ ID NO: 14.

The PiggyBAC 5' Terminal Repeat may comprise or consist of a truncated version of SEQ ID NO: 14 or truncated version of a variant of SEQ ID NO: 14 which retains ability to facilitate insertion into the host genome.

The PiggyBAC 3' Terminal Repeat may comprise or consist of a variant which shares at least 80%, at least 85%, at least 90%, at least 95%, or at least 99% sequence identity with SEQ ID NO: 15 and retains the ability to recruit an RdRp. The PiggyBAC 3' Terminal Repeat may comprise or consist of SEQ ID NO: 15.

The PiggyBAC 3' Terminal Repeat may comprise or consist of a truncated version of SEQ ID NO: 15 or truncated version of a variant of SEQ ID NO: 15 which retains ability to facilitate insertion into the host genome.

A hyperactive piggyBac transposase (hyPBase) was recently generated by an error-prone polymerase chain reaction (PCR)-based genetic screen and is believed to be the most active transposase known (see Yusa et al; PNAS 108, 1531-1536 (2011). hyPBase may be used for generation of stable insertions of the present invention.

Suitably, stable integration of the nucleotide sequence encoding any of the vectors described herein including a retrovirus nucleic acid transfer vector or any of the retroviral helper elements described herein may be achieved by the use of transposon elements. The transposon elements may flank the nucleotide sequence to be integrated into the genome of the packaging or producer cell. Any suitable transposon may be used including the piggyback transposon e.g. the 5' and 3' PB transposon sequences set forth in SEQ ID NO: 14 and SEQ ID NO: 15.

In one aspect the nucleic acid transfer vector for transposition comprises the nucleotide sequence set forth in SEQ ID NO: 16 or a variant thereof having at least about 70%, 75%, 80%, 85%, 90%, 95%, 97%, 98%, or 99% sequence identity thereto wherein the product of the variant nucleic acid transfer vector maintains the biological activity of the product encoded by SEQ ID NO: 16 e.g. the variant sequence allows stable integration of the nucleic acid transfer vector into the genome of the packing or producer cell, functional transcription, replication by the RdRp and expression of the nucleotide of interest by the packing or producer cell.

Suitably the nucleic acid transfer vector for transposition comprises the nucleotide sequence set forth in SEQ ID NO: 16.

-Sequence of a transposable sindbis amplifiable lentiviral transfer cassette

SEQ ID NO: 16

```
   1  gcaactgttg ggaagggcga tcggtgcggg cctcttcgct attacgccag ctggcgaaag ggggatgtgc tgcaaggcga ttaagttggg taacgccagg
 101  gttttcccag tcacgacgtt gtaaaacgac ggccagtgag cgcgcgtaat acgactcact atagggcgaa ttggggcgcg ccattctaga ttaaccctag
                                                                                                     >>......PB5TR......>

201  aaagatagtc tgcgtaaaat tgacgcatgc attcttgaaa tattgctctc tctttctaaa tagcgcgaat ccgtcgctgt gcatttagga catctcagtc
      >...................................................PB5TR...................................................>
 301  gccgcttgga gctcccgtga ggcgtgcttg tcaatgcggt aagtgtcact gattttgaac tataacgacc gcgtgagtca aaatgacgca tgattatctt
      >...................................................PB5TR...................................................>
 401  ttacgtgact tttaagattt aactcatacg ataattatat tgttatttca tgttctactt acgtgataac ttattatata tatattttct tgttatagat
      >...................................................PB5TR...................................................>
 501  atcaactaga atgctagcgc ggccgcctcg agggatccgg agtcttatgc aatactcttg tagtcttgca acatggtaac gatgagttag caacatgcct
      >...PB5TR...>>
                                                >>..........................RSV-LTR............................>
 601  tacaaggaga gaaaaagcac cgtgcatgcc gattggtgga agtaaggtgg tacgatcgtg ccttattagg aaggcaacag acgggtctga catggattgg
      >..................................................RSV-LTR..................................................>
 701  acgaaccact gaattccgca ttgcagagat attgtattta agtgcctagc tcgataccgt cgagattgac ggcgtagtac acactattga atcaaacagc
      >.........................RSV-LTR.........................>>
 801  cgaccaattg cactaccatc acaatggaga agccagtagt aaacgtagac gtagaccccc agagtccgtt tgtcgtgcaa ctgcaaaaaa gcttcccgca
                                >>..................................NSP1d....................................>
                                >>................................sind5CSE...................................>
                                >>...................................orf.....................................>
 901  atttgaggta gtagcacagc aggtcactcc aaatgaccat gctaatgcca gagcattttc gcatctggcc agtaaactaa tcgagctgga ggttcctacc
      >>..............................................NSP1d...............................................>
      >>............................................sind5CSE..............................................>
      >>...............................................orf................................................>
1001  acagcgacga tcttggacat aggcagcgca ccggctcgta gaatgttttc cgagcaccag tatcattgtg tctgccccat gcgtagtcca gaagacccgg
      >>..............................................NSP1d...............................................>
      >>............................................sind5CSE..............................................>
      >>...............................................orf................................................>
1101  accgcatgat gaaatatgcc agtaaactgg cggaaaaagc gtgcaagatt acaaacaaga acttgcatga gaagattaag gatctccgga ccgtacttga
      >>..............................................NSP1d...............................................>
      >>........................................sind5CSE.........................................>>
      >>...............................................orf................................................>
1201  tacgccggat gctgaaacac catcgctctg ctttcacaac gatgttacct gcaacatgcg tgccgaatat tccgtcatgc aggacgtgta tagagccgag
      >>.........................................NSP1d..........................................>>
      >>...............................................orf................................................>
                                                                                                         >>......>
1301  ggccgagggt ccctcctgac atgcggagac gttgaggaaa atcctggacc aatgggaacc tcacttcttt gctggatggc actttgtctt cttggagccg
      >>...............................................orf................................................>
      >......................FMD-2A.......................>>
                                                       >>......................MYC8.......................>
1401  atcacgcaga tgctgagcag aagctcatca gtgaagagga cttgtctgga gggggaggga gtccggctcc caggccgcca acacctgcgc caactatcgc
      >>...............................................orf................................................>
      >>..............................................MYC8................................................>
1501  ctcccagcca ttgtccttga ggccagaggc atgtcgcccc gcagcgggag gcgccgtcca tacccgcggt ttggacttcg catgtgatat ttatatttgg
      >>...............................................orf................................................>
      >>..............................................MYC8................................................>
1601  gctccactcg cgggtacatg cggagtcttg ttgctctctc ttgtgattac gctttactgc aaccaccgga acagaaggcg agtatgtaaa tgtccccggc
      >>...............................................orf................................................>
      >>..............................................MYC8................................................>
```

```
                                         -continued 1701  cgtagtata gtcagcatag tacatttcat ctgactaata ctacaacacc accaccccta gaaccggtaa ggcaagcttt attgaggctt aagcagtggg
      >..orf...>>
      >..MYC8...>>
               >>.......sindSGP.................>>

1801  ttccctagtt agccagagag ctcccaggct cagatctggt ctaaccagag agaccagta caagcaaaaa gcagatcttg tcttcgttgg gagtgaatta
                                                                                                    <<.....<<
                                                                       <<......3R.............
                                                                       <<......dLTR'................
               >........3R...........

1901  gcccttcag tcccccttt tcttttaaaa agtgctaag atccacagct gcttgtaag tcattgtct taaagtacc gagctcgaat tccaggcggg
      <...dLTR'.<<

2001  gaggcggccc aaagggagat ccgactcgtc tgagggcgaa ggcgaagagc cggaagaggc cgcagagggg gcagcaggcc gcggaaagga agtccgctg
                                                                                                             v
                                                                        mtPRE............

2101  gattgaggg cgaaggacg tagcagaagg acgtcccgcg cagaatcgag gtgcaacac aggcgagcag acgcagatgc ccaaggaaag tccccgacaa
                                                                        mtPRE............                   v 2201  caccacgaa ttgtcagtgc ccaaagcccg agccctgtc cagcagccgg caagccaggc ggcgatgagt tccgccgtgg caataggag gggaaagcg
                                                                        mtPRE............                   v 2301  aaagtcccgg aaagggagct acagtggtg gcaatgcccc aaccagtggg ggtgcgtca gcaaaacag tgcaccac gccacgttgc ctgacaacgg
                                                                        mtPRE............                   v 2401  gccacaactc ctcataaaga dacagcaaac aggatttata caaggagaga aaaatgaaag ccatacggga agcaatagca tgatacaaag gcattaaagc
                                                                        mtPRE............                   v 2501  agcgtatcca catagcgtaa aaggagcaac atagtaaga ataccagtca atcttcaca aattttgtaa tccagaggtt gattgtcgag cccggatct
                  mtPRE............                                                                         v 2601  ctcgagacgc gttcacgg gtggcaggg ctgcatgtc aggcgtcgt aggtgtcctt gtgggcgt ctcagccct cgttgtacag gcccctctg gtcgtgccc
                                                                        orf....                             v 2701  ttgcccggc gccgctcgc cggccatc tcgggtcc gtcccgccg atctcgctgt aggcctccgc catctgtcc ttctgcagct cgttgcagt gccctcctg ggattcttcc
                <<........                                              orf....                             v 2801  ggcgaggctt gccgccatc tcgggtcc gtcccgccg ctgtccac acgtcgtact ctcccccgg ctcccgctc agtcgttgc tccttctgcg acagctgtt
                                                                        orf....                             v 2901  ctggcccctgc tgtagccgg gggcgtcggc gtcggctc aacttcaccc gcagctcgca gccgcttcc tcttcctcgg ggaaccggca gctgcagccg
                                                                        orf....                             v 3001  tcctccccct gggtggctg cacgggcgc atgaagggct gcttgaagat gtacagcagc ttcttccgc ccgtttgca atacagtga atcaccaggg
                                                                        orf....                             v 3101  acagcagcag cacccgccat gtcccggca ggggggccca gatatagatg tcaggcgca tcgcaggcga cctggtgtgc acggctcctc cggccgcagg
                                                                        orf....                             v 3201  cctgcagct tcaggccga ggctcagggg ctggctgggc atggtgggag cagggtagg ctggcctgc cagggtagg gctgggagg tgtgggatc cgaccgttc
                                                                        orf....                             v 3301  agctccagct tggtgccgg gccgaaggtc agaggattga tgtccactg ctggcagtag gtgtgcgg cgtcctgggc ctccatgtt ttgatggtca
                                                                        orf....                             v 3401  ggagtagct ggtgccctg ccgtgccgc atgaagggct tgaaacggtc tgccctgcgc ctgccagct tgctggtgtc gtagatccac cgcttaggc tggtccgct
                                                                        orf....                             v 3501  cttctgtgg taccagtga tgtgctgca tgtagtcac gcgtgcagg ccgtgcac tcatggtgct ggcctggcgc tcatgatgc agggtctgg
                                                                        orf....                             v 3601  gtcacgacgg tctgcgtgcc gcctccgca gagcacccc cgccagagcc gccaccctc gagctcacgg tcaggtggt gcccggccc cagtagtcca
                                                                        orf....                             v 3701  ggtagtcgcc gtacacgcag ctccggcgcg agaagtacac gggcgtgcc tgctggtca ggctgtcag ctgtgagcgg cggtggtgc tgtctgtc
                                                                        orf....                             v 3801  ggcggtcagg gtgccttgt ccttgaactt gccgtgtag ttgtgtcct cgtcgccggg gtagatccgg cgatccact ccaggcctt gccaggcgc
                                                                        orf....                             v 3901  tgcttcaccc agttcatcca gctgctgctg aaggcgtagc cgctgtgatc ttcacgctg ctcccgggct caccagctgg gtccgtct
                                                                        orf....                             v
```

```
                                                                     -continued
4001  gctgcagctg cacctgggcg tcggcgtggt cggctcccag caggcacagg gcatccccag acagcaggct ggtgcccatg gtggcgtcga cctggggag
                                                                                                     <<..hPGK.<
4101  agaggtcggt gattcgtca acgagggagc cgactgccga cgtgcgctcc ggaggcttgc agaatgcgga acaccgcgcg ggcaggaaca gggccacac
      <............................................................hPGK............................................<
4201  taccgcccca caccccgcct cccgcaccgc cccttcccgg ccctgcgcgc cgctgcccgc tgctgagcag ccgctattgg ccacagccca tcgcggtcgg
      <............................................................hPGK............................................<
4301  cgcctgcca ttgctccctg gcagtcccg gcgctgtccg tctcgaggg tactagtgag actgcggct gag actcccggca cgcgcgaac cgcaaggaac
      <............................................................hPGK............................................<
4401  cttcccgact tagggcgga gcaggaagcg tgcgttccc ggaccacgc ggcacaaag gtagcggca gatgcggga acgacgtga agaatgcg
      <............................................................hPGK............................................<
4501  agaccaggg tcggccgcgc tgcgttccgc ggaaccacgc ccagagcacg ccgtccctg cgcaaaccgc gggctgcctt ggaaaaggcg caacccaac
      <............................................................hPGK............................................<
4601  cccgtggcct gcagggaat tcgataaaat tttgaatttt gtaattgtt tttgtaatc ttagttgt atgtcgttg ctattagtc tactattctt
      <............................................................hPGK............................................<
4701  tcccctgcac tgtaccccc aatcccccct tttctttaa aagtaaacg ataccgtga gatccgtca ctaatcgaat ggatctgtct ctgtctctct
      <.......................sindb_frag........................<                                   .RAE.
4801  ctccactc tctctatt cctgggcc tgtcgggtcc cctcgggtgg tctgaaacga tctgttgaa tcctcctgc caattgtt tatgtttaaac
                                                                                          .RAE.
4901  cactatagaa agtacagca aaactattct taaactacc agctccca ctatcattat gaattattt atataccaca gccaattgt tatgtttaaac
                                                                                          .RAE.
5001  caattccaca aactgccca tttatctaat tccaataatt ctgttcatt cttgttttgc atgtttgcg attcttcaat taaggagtgt attaagttg
                                                                                          .RAE.
5101  tgtaattgtt aatttctg tccccactcg tccagtcgt gtgattccaa atctgttcca gagattatt actccaacta gcattccaag gcacagagt
      <.......sindb_frag..........<                                                                  .RAE.
5201  ggtcaatg agtttccag agcaaccca atagagggt gctactgtat tatataatga gctactgtat tatatatga tctaagttct ctgaaggga
                                                                                                     <<
5301  cccagactg tgagtgcaa cagatgctgt tgcgcctcaa tagccccgc caaattgtc tgctgctgca ctataccaga cttaccctgg ctgttatg
                                                                                                     .PSI.
5401  ccgcagcgt cattgacgct gcgccatag tgctcctgc tgttcctgc tgtcccaga acaaagctcc tattccccact gctctttt ctctccgcac
                                                                                                     .PSI.
5501  caccctctc tttgccttgg tgggtgctac tcctaatggt tcaatttta ctactttata tcacttctc aattgtccct catattctct
                                                                                                     .PSI.
5601  ccctccagg ctgaagatcag cggccgttg ctgtcggtg gcttactt tgtttgtc ttccctatc ttgtctaaag cttccttggt gtctttatc
                                                                                                     .PSI.
5701  tctatccttt gatgcacaca atagagggt gctactgtat gctactgtat tatataatga gctactgtat tatataatga gctactgta
                                                                                                     'dLTR'
5801  tttgtctaca gccctttgat gttctcaaca ggccaaggatt aactgcgaat cgttctagct ccctgcttg ctgactgc ccatactata tgtttaatt
                                                                                                     'dLTR'
5901  ctttccccct ggcctaacc gaatttttc ccatcgat ctaattctc cccgcttaat actgacgtcc tcgcaccat ctctcctt ctagcctcg
                                                                                                     'dLTR'
6001  ctagtcaaaa tttttggcgt actccacagt cgcccccct cgccctccgt cgtgcgggct tcagcaagcc gagtcctgcg tcgagagagc tcctctggtt
                                                                                                     'dLTR'
6101  tccctttgc tttcaagtcc ctgtcgggc ctgttcggg gccactgcta gagatttcc acactgacta aaagggtctg agggatctct agtaccaga gtcacacaac
                                                                                                     'dLTR'
6201  agacgggcac acactacttg aagcactcaa ggcaagcttt attgaggctt ttgaagctt aagcagtggg ttccctagt agccagagag ctccagggt cagatctgt
      <........dLTR........<
6301  ctaaccagag agaccaccg gtccgctacg cccaatgatc cgaccagcaa aactcgatgt acttccagg cataatgcag gaattcgata
      <........SindFrag........>
```

| | | | | | | | | |
|---|---|---|---|---|---|---|---|---|
| 6401 | tcaagctaga | tctcacgtga | gcatgcaggc | cttgggccca | atgatccgac | cagcaaaact | cgattactt | ccgaggaact | gattactt |
| | ^ | | | | >> | | | .Sind3UTR/CSE | |
| 6501 | ctggtacatt | agatcccgc | tataccgcgg | caatatagca | acactaaaa | ctgatgtac | ttccgaggaa | gcgcagtgca | taatgctgcg |
| 6601 | acataaccac | tatattaacc | atttatctag | cggacgccaa | aaactcaatg | tatttctgag | gaagcgtggt | gcataatgcc | accgcagtc |
| 6701 | ttatattc | ttttattaat | caacaaaatt | ttgtttttaa | catttcaaaa | aaaaaaaaaa | aaaaaaaaaa | aaaaaaaaaa | aaggaatt |
| | ^ | | | | ....Sind3UTR/CSE. | | | >> | |
| 6801 | ttattgcagc | ttataatggt | tacaaataaa | gcaatagcat | cacaaatttc | acaaataaag | catttttttc | actgcattct | agtgtggtt |
| 6901 | catcaatgta | tcttatcatg | tctgatccg | tccgagacgcg | ctgcattaga | tccattcatg | aatgaattca | tgtcgacata | ctagttaaa |
| 7001 | gttttgttac | aaatttgag | tttttgttt | ttttaataa | ataaataaac | ataaataaat | tgttgttga | atttattatt | agtatgtaag |
| 7101 | tgtaaaata | ataaaactta | atatctattc | aaattaataa | ataaacctg | atatacgac | cgataaaaca | catgcgtcaa | tttacgcat |
| 7201 | aacgtacgtc | acaataatgat | tatctttcta | gggttaatct | agtatacgcg | gcacgacct | gactgtttga | caattaatca | tcggcatagt |
| 7301 | agtataatac | gactcactat | aggagggcca | ccatgattga | acaagatgga | ttgcacgcag | gttctccgc | cgcttgggtg | gagaggctat |
| 7401 | ctggacaa | cagagacaatcg | gctgtctga | tgccgccgtg | ttccggctgt | cagccagggg | cgcccggtt | cttttgtca | agaccgacct |
| 7501 | ctgaatgaac | tgcaggacga | ggcagcgcgg | ctatcgtggc | tggccacgac | gggcgttcct | tgcgcagctg | tgctcgacgt | tgtcactgaa |
| 7601 | actggctgct | attgggcgaa | gtgccggggc | aggatctcct | gtcatctcac | cttgctcctg | ccgagaaagt | atccatcatg | gctgatgcaa |
| 7701 | gcatacgctt | gatccggcta | cctgcccatt | cgaccaccaa | gcgaaacatc | gcatcgagcg | agcacgtact | cggatggaag | ccggtcttgt |
| 7801 | cgatcaggat | gatctggacg | aagagcatca | ggggctcgcg | ccagccgaac | tgttcgccag | gctcaaggcg | agcatgcccg | acggcgagga |
| 7901 | atctcgtcgt | gacccatggc | gatgcctgct | tgccgaatat | catggtggaa | aatggccgct | tttctgcatc | atcgactgtg | gccgcggac |
| 8001 | tgtcctcggg | cctcactgaa | atgccgatc | aggatggatc | gcatcgagcc | agcagtacgc | gaattcgtac | gcatggtca | gcagcagtgt |
| 8101 | ggctaccgt | gatatgctg | aagagcttg | cggcgaatgg | gctgaccgc | ttcctcgtgc | tttacggtat | cgccgctccc | gattcgcagc |
| 8201 | tatctcgtt | gatccggca | aagccatga | cggcaagcag | gcttaccta | gaccacgaa | aaggcgtcaa | gcatggcga |
| 8301 | gcggtttgg | ccagctgtg | caccacaac | aggtttaac | aaggctgct | gggattttt | gatagataa | tgtgcctga |
| 8401 | acgagacac | aagctgg | ccagcagcaacaag | ggtttcaaag | tgaaagac | atctccagct | agccacacg | atttgctgg | gtgagctg |
| 8501 | caggcggac | ctggcagtag | acgagcatac | ccttttatt | cctgatttc | cagggattc | cagcagtgtt | gttgccgag | gttgacggc |
| 8601 | cgcggtg | cagaacgtg | caagaggcag | agttgcctaa | gccagaagc | aagggattgtca | caggttgctc | cagaattcca | aagcagccagc |

```
8701  cggtaagcgg cagggtcgga acaggagagc gcacgaggga gcttccaggg ggaaacgcct ggtatcttta tagtcctgtc gggtttcgcc acctctgact
      ^.........................................................ORI...................................^
8801  tgagcgtcga tttttgtgat gctcgtcagg gggcggagc ctatgaaaa cgccagcaa cgcggccttt ttacggttcc tggcctttg
      ^.........................................................ORI...................^
8901  gctcacatgt tctttaattaa cagggcgcgt cccattcgcc attcaggctg c
```

Plasmid

In one aspect the present invention provides a plasmid comprising a retroviral nucleic acid transfer vector or a retroviral helper element nucleotide sequence of the present invention.

The term plasmid covers any DNA transcription unit comprising a retroviral nucleic acid transfer vector or a retroviral helper element nucleotide sequence according to the invention and the elements necessary for its in vivo expression in a desired cell; and, in this regard, it is noted that a supercoiled or non-supercoiled, circular plasmid, as well as a linear form, are intended to be within the scope of the invention.

Variant

As used herein, a variant sequence may be an amino acid sequence or a nucleic acid sequence which is at least 70, 80, 85, 90, 95, 98 or 99% identical, preferably at least 95 or 99% identical to a sequence shown herein.

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % sequence identity. The software typically does this as part of the sequence comparison and generates a numerical result.

The terms "variant" according to the present invention includes any substitution of, variation of, modification of, replacement of, deletion of or addition of one (or more) amino acids from or to the sequence providing the resultant amino acid sequence retains substantially the same activity as the unmodified sequence.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

A nucleic acid sequence or amino acid sequence as described herein may comprise, consist of or consist essentially of a nucleic acid sequence or amino acid sequence as shown herein.

Method

In one aspect the present invention relates to a method for making a packaging cell according to the present invention which comprises the step of introducing a nucleic acid construct encoding a RdRp as defined herein into a cell, such that the cell expresses the RdRp.

The nucleic acid construct may be provided as a plasmid as described herein.

The nucleic acid construct may be introduced into a cell by a variety of methods which are known in the art, for example using standard transfection methods such as electroporation or lipofection.

In one embodiment the method may comprise the step of introducing a retroviral helper element nucleotide sequence encoding a retroviral protein as described herein into the cell. The method may comprise the step of introducing a plurality of retroviral helper element nucleotide sequences as defined herein into the cell, wherein each retroviral helper element nucleotide sequence encodes a different retroviral protein.

In one aspect the present invention provides a method for making a producer cell which comprises the steps of making a packaging cell as defined herein and further comprises the step of introducing a retroviral nucleic acid transfer vector into the cell.

The nucleic acid sequence nucleic acid encoding a RdRp as defined herein, the retroviral nucleic acid transfer vector and/or the a retroviral helper element nucleotide sequence encoding a retroviral protein as described herein may be introduced into the cell during the same step of the method (e.g. transfected at the same time) or at different steps in the method (e.g. transfected at different times).

The retroviral nucleic acid transfer vector may be introduced into the cell during the same step of the method as the retroviral helper element nucleotide sequences (e.g. transfected at the same time) or at different steps in the method to the retroviral helper element nucleotide sequence (e.g. transfected at different times, particularly after the retroviral helper element nucleotide sequences have been introduced into the cell).

Accordingly, the present invention provides a method for making a producer cell which comprises the step of introducing a retroviral nucleic acid transfer vector into a packaging cell according to the present invention.

The present invention further provides a method for producing a retrovirus vector particle which comprises the steps of culturing a producer cell according to the present invention and isolating the retrovirus vector.

In one embodiment the method for producing a retrovirus vector particle comprises the steps of culturing a producer cell according to the present invention at a relatively high temperature (e.g. to propagate the producer cell) and then culturing the producer cell at a relatively low temperature (e.g. to produce the retrovirus vector). The method may further comprise the step of isolating the retrovirus vector.

Suitably, the RdRp has low activity at the relatively high temperature and a high activity at the relatively low temperature.

The method may comprise culturing the producer cell at a relatively high temperature until the producer cell cultures reach the desired confluency. The desired confluency may be e.g. 70, 80, 90, 95 or 100% confluent.

The method may further comprise reducing the temperature of the culture to a relatively low temperature once the producer cells reach the desired confluency.

At the relatively low temperature the RdRp is highly active and large amounts of virus are produced by the producer.

The producer cell may be cultured using standard culture conditions suitable for the particular cell type used to make the producer cell. During culture, retrovirus vector particles are released into the culture supernatant. The retrovirus vector may be isolated using standard techniques, for example, ultracentrifugation, ultrafiltration or affinity purification Kit The present invention further provides a kit for making a packaging cell according to the present invention which comprises at least two retroviral helper element nucleotide sequences as defined herein.

In one embodiment the kit may comprise:
(i) a retroviral helper element nucleotide sequence as defined herein which encodes gag-pol; and
(ii) a retroviral helper element nucleotide sequence as defined herein which encodes env.

In present invention further provides a kit for making a producer cell according to the present invention which comprises a retroviral nucleic acid transfer vector as defined herein and at least one retroviral helper element nucleotide sequence as defined herein.

Definitions of terms appear throughout the specification. Before the exemplary embodiments are described in more detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and equivalents thereof known to those skilled in the art, and so forth.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The invention will now be further described by way of Examples, which are meant to serve to assist one of ordinary skill in the art in carrying out the invention and are not intended in any way to limit the scope of the invention.

EXAMPLES

Example 1—Temperature Regulation of eGFP Expression

Figure 3:
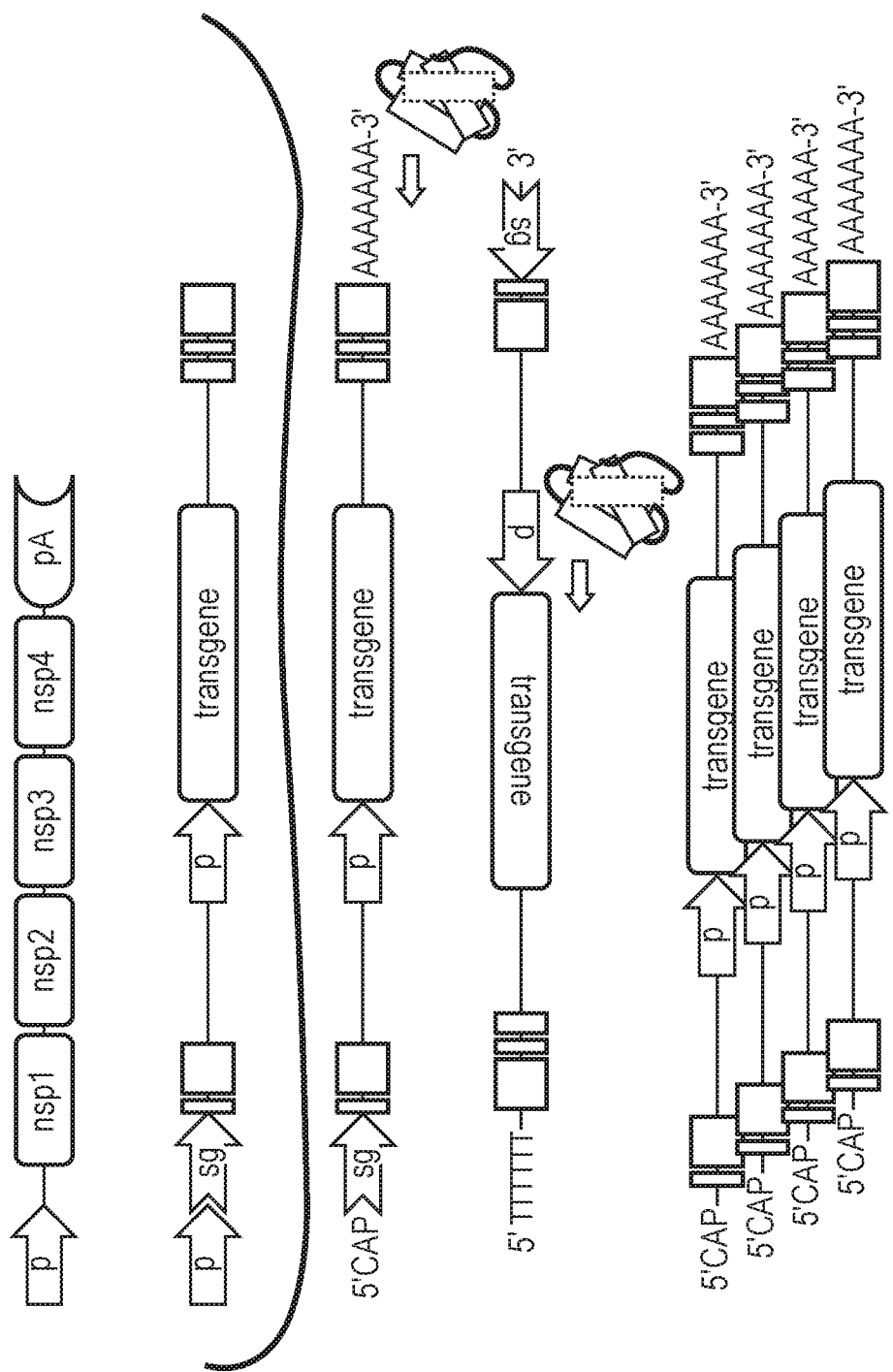
FIG. 3—Schematic diagram of temperature-regulated retroviral protein amplification. The recombinant retroviral helper element nucleotide sequence encoding a retroviral protein is integrated into the packaging cell genome. The retroviral protein (e.g. gagpol or VSV-G env) is cloned after the subgenomic promoter (PSG). The DNA is transcribed by the usual mammalian machinery and the mRNA exported to the cytoplasm for translation of the NSPs. There is a stop codon after the last NSP so little or none of the retroviral protein is translated. A mutation in the NSP4 domain (G153E) renders the enzyme inactive at temperature above 35° C. but active below 35° C. (see SEQ ID NO: 2). Once active, NSP proteins act to bind to the 3' end of the transcript and transcribe the reverse strand and cap it. Next, the complex binds the subgenomic promoter (Psg) on the reverse strand and initiates its transcription. These small positive strands lack the NSP frame and a kozak sequence leads to translation of the retroviral protein.

The temperature-dependent regulation of expression of the RdRp from 987*SinRep (SEQ ID NO: 2) was tested in HEK293T cells. The eGFP open reading frame (SEQ ID NO: 3) was cloned downstream of the subgenomic promoter. Subsequently, both the control plasmid 987SinRep-eGFP and the mutated plasmid 987*SinRep-eGFP were transfected into HEK293T cells using GeneJuice (as per manufacturer's protocol). Cells were either incubated at 37° C. and 29° C. and then eGFP expression was assessed 48 hrs post-transfection by Flow Cytometry (FIG. 3).

The percentage of eGFP-positive cells in cells transfected with 987*SinRep plasmid was two log higher at 29° C. than at 37° C., whereas that of the 987SinRep control plasmid was a quarter of a log lower at 29° C. than 37° C. (FIG. 3($a$)). Moreover the MFI of eGFP positive cells transfected with 987*SinRep was significantly higher at 29° C. than at 37° C., while the opposite was seen for the control plasmid 987SinRep (FIG. 3($b$)).

These results indicate that the RdRp expressed in 987*SinRep plasmid is able to regulate eGFP expression in a temperature-dependent manner.

Example 2—Cytotoxic Effects of VSV-G

To evaluate the feasibility of regulating cytotoxic lentiviral protein using the thermolabile RdRp, VSV-G (SEQ ID NO: 4) was cloned downstream of the subgenomic promoter of 987*SinRep plasmid. Next, HEK293T cells were transiently transfected with both VSV-G (wild-type) and 987*SinRep-VSV-G using GeneJuice and incubated for 37° C. and 29° C. for 48 hours.

Figure 4:
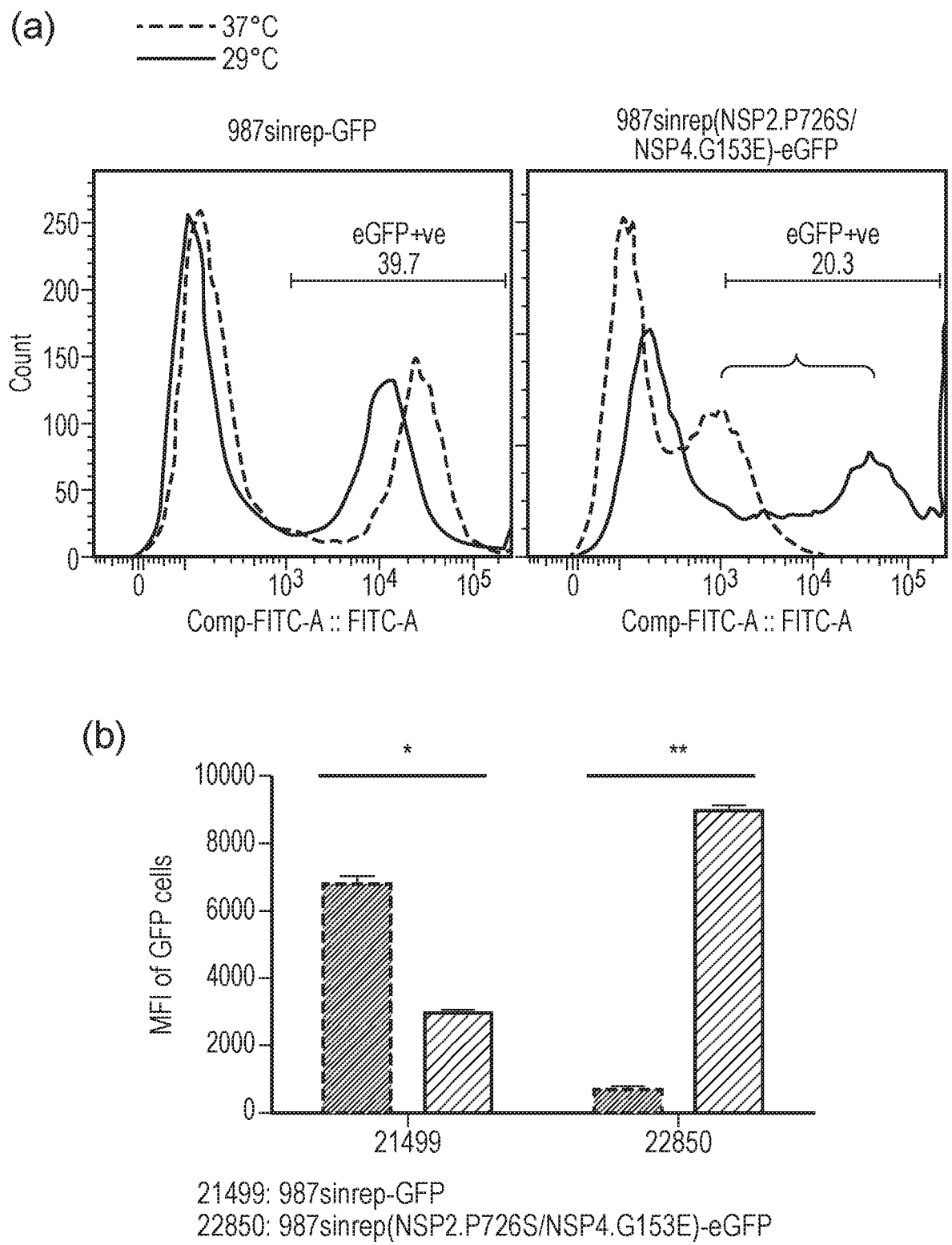
FIG. 4—Induction of eGFP expression by temperature control. (a) HEK293T cells were transiently transfected with 987SinRep-eGFP and 987*SinRep-eGFP that has both NSP2 P726S and NSP4 G153E substitution mutations. Cells were incubated at 37° C. and 29° C. for 48 hours when eGFP expression was determined by Flow Cytometry. (b) Mean fluorescence intensity of eGFP positive cells of both control plasmid (21499) and temperature-regulated-RdRp plasmid (22850) is plotted (n=3) with * p=0.5; ** p<0.5.

Syncytium formation was clearly visible for cells transfected with VSV-G at 37° C. while the cell density was lower than the control (NT, non-transfected) at 29° C. (FIG. 4($a$)). This was further apparent when the absolute live cell numbers was determined and both temperature conditions had similar very low live cell count (FIG. 4($b$)). Conversely, no syncytium formation was seen in cells transfected with 987*SinRep-VSV-G at both 37° C. and 29° C. (FIG. 4($a$)). However, cells incubated at 29° C. had a significantly lower absolute cell count than cells incubated at 37° C. (FIG. 4($b$)).

These results clearly indicate the regulation of VSV-G's cytotoxicity in expressing cells in a temperature-dependent manner.

Example 3—Temperature Induction of Lentiviral Vector Production

To determine whether the lentiviral helper genes (VSV-G and Gagpol), expressed under the transcriptional regulation of RdRp, can be induced for viral vector production, human codon optimized Gagpol (SEQ ID NO: 5) was cloned downstream the subgenomic promoter of 987*SinRep. HEK293T cells were transiently transfected with 2nd generation packaging system; 987*SinRep-VSV-G, Gagpol and a transfer vector encoding eGFP, and with a 3rd generation packaging system; VSV-G, 987*SinRep-Gagpol, REV and a transfer vector encoding eGFP. All conditions were incubated at both 37° C. and 29° C. for 48 hours upon transfection. Subsequently, supernatants were collected and processed to remove cellular debris. Serial dilutions were prepared for each condition (6 points, 1:2) and each fraction was added onto NT-293T cells to assess transduction and viral titres.

Figure 5:
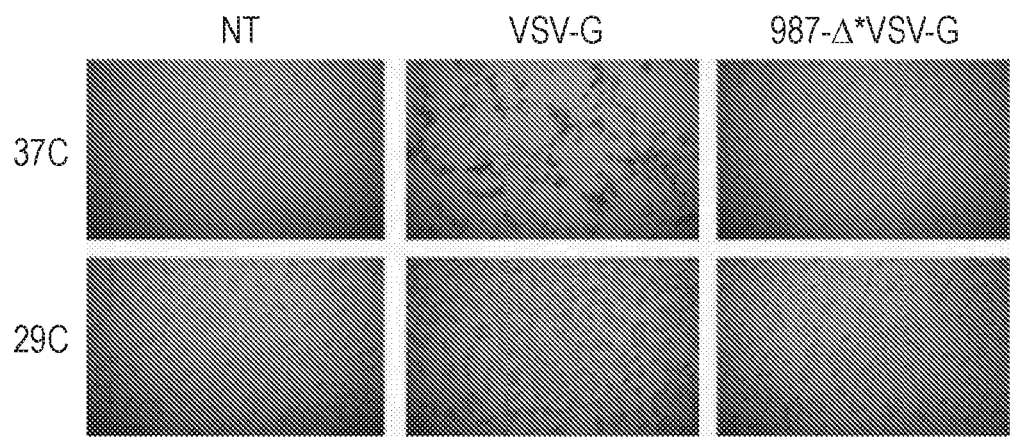
FIG. 5—Prevention of cytopathic effects by temperature control. HEK293T cells were transfected with VSV.G and 987*SinRep-VSV-G (contains NSP2 P726S and NSP4 G153E substitution mutations) and incubated at both 37° C. and 29° C. for 48 hours. (a) Cultures were documented for cellular morphology to detect syncytium formation. (b) Cells were harvested and stained with a viability dye and counting beads to plot the absolute live cell number (n=3) with * p=0.5.
Figure 5:
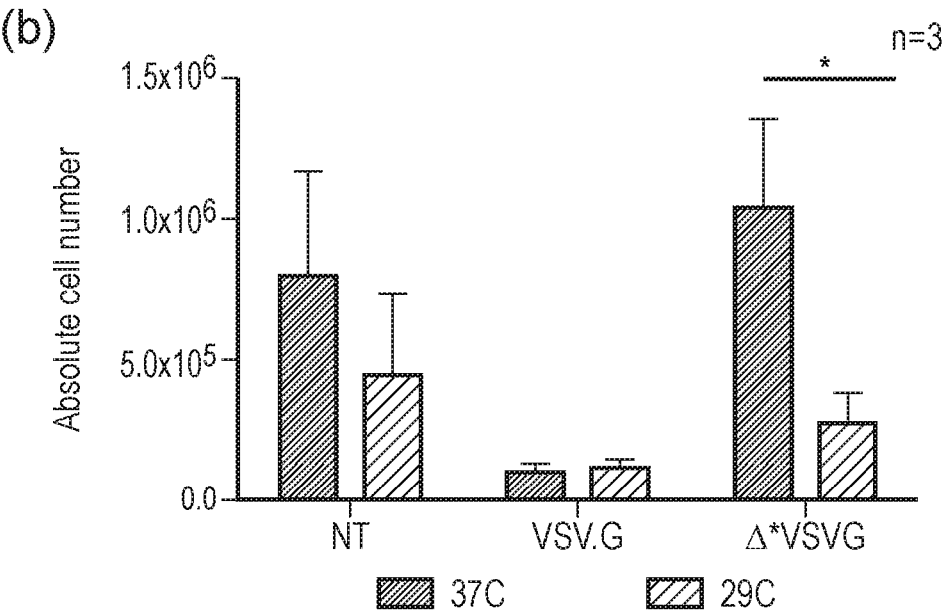
Figure 6:
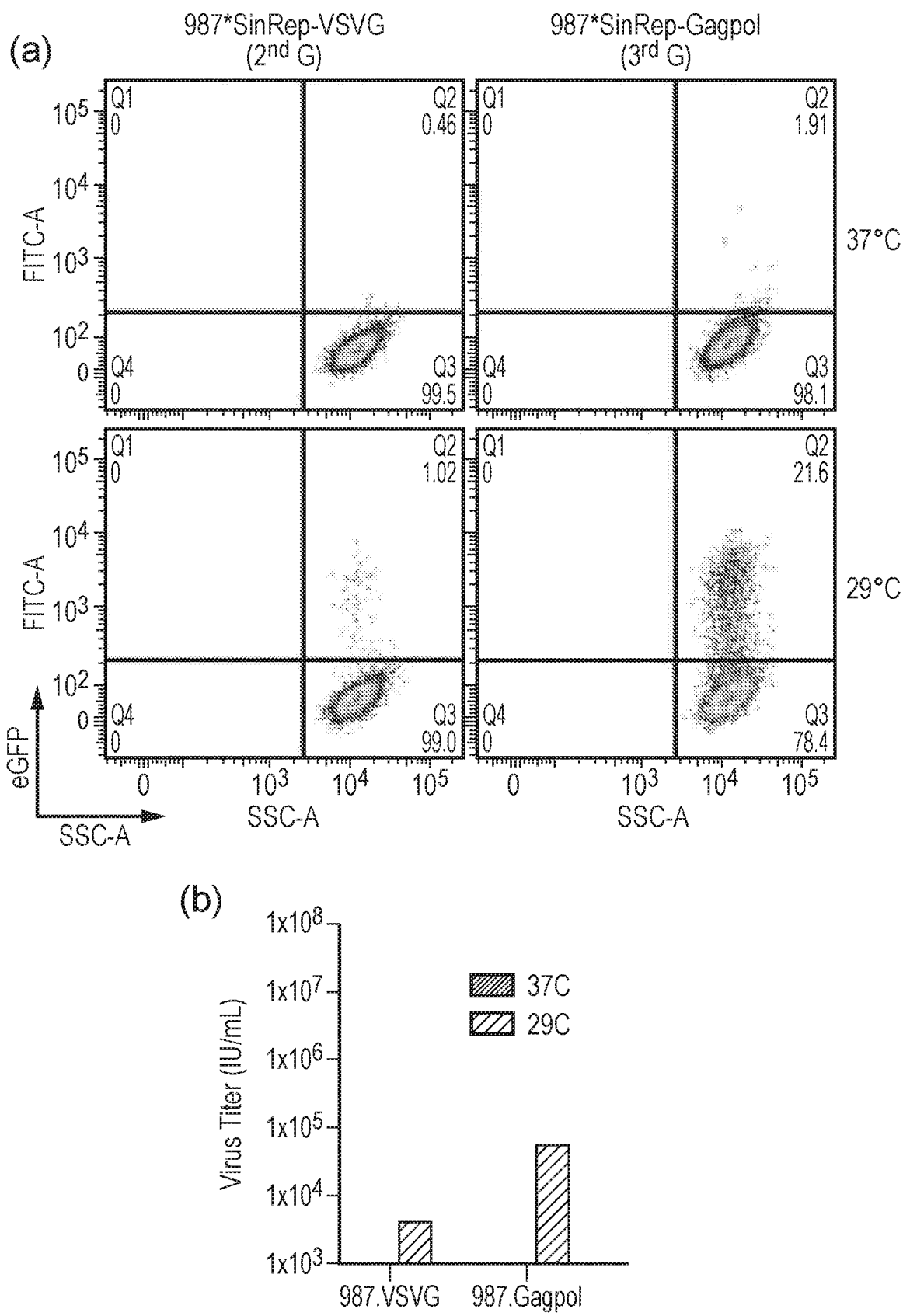
FIG. 6—Temperature induction of lentiviral vector production. HEK293T cells were transiently transfected to produce lentiviral (LV) supernatant; 2nd generation packaging system (2nd G) using 987*SinRep-VSV-G, Gagpol and Transfer vector (pCCL.PGK.eGFP) and a 3rd generation packaging system (3rd G) using 987*SinRep-Gagpol, VSV-G, REV and Transfer vector (pCCL.PGK.eGFP). Both systems were incubated at 37° C. and 29° C. for 48 hours. Then the supernatants were harvested and spun at 1000 G for 10 mins at 4° C., followed by ultrafiltration through 0.45 um filters. All LV supernatants were serially diluted starting from 500 uL, 6 points with a dilution of factor of 1:2. All fractions were then added onto NT-293T cells in the presence of 5 ug/mL of the transfection reagent Polybrene. (a) eGFP expression was then determined 72 hours post-transduction by Flow Cytometry (500 uL LV supernatant/well transduction). (b) Viral titres were determined by eGFP expression of serial diluted viral fractions and plotted.
Figure 7:
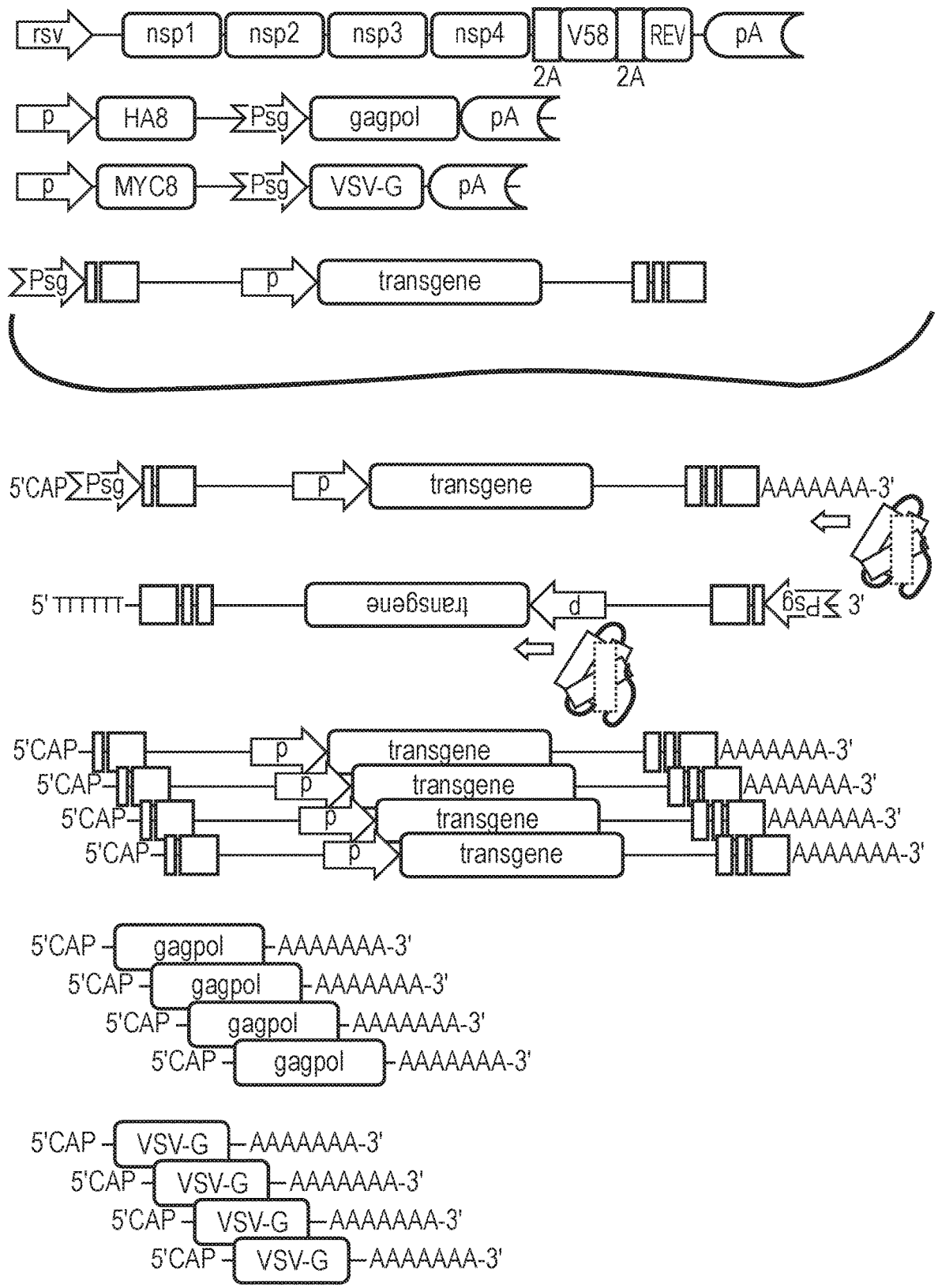
FIG. 7—An illustrative combined approach for efficient lentiviral vector production. The sinbnis non-structural protein is supplied co-expressed with lentiviral rev using a 2A peptide. A marker gene (V58) is also co-expressed with this. Gagpol and VSV-G env have marker genes 5' to their orf separated by the subgenomic promoter—this means the initial transcript only expresses the marker genes but not the toxic gagpol or VSV-G env. The transfer vector has the subgenomic promoter ahead of the R region of the 3' LTR. Once the sinbis non-structural components activate with a drop in temperature, anti-sense and then sense transcripts are generated at high levels.

Supernatant produced with 987*SinRep-VSV-G at 29° C. infected HEK293T cells with a transduction efficiency of 1.02% compared to a void transduction with supernatant produced at 37° C. (FIG. 5($a$)); thus the former generated a functional infectious titre of $4 \times 10^{-3}$ IU/mL at 29° C. (FIG. 5($b$)). Moreover, supernatant produced with 987*SinRep-Gagpol at 29° C. transduced HEK293T at 21% eGFP-positive cells whereas that produced at 37° C. seemed to have a very low/undetectable transduction levels (FIG. 5($a$)). 987*SinRep-Gagpol at 29° C. successfully packaged viral particles with a titre of $5.6 \times 10^{-4}$ IU/mL with no detectable infectious virus at 37° C. (FIG. 5($b$)).

These results indicate that the functional expression of both 987*SinRep-VSV-G and Gagpol are temperature regulated thus inducing viral vector production at 29° C. with no detectable titres at 37° C.

Example 4—Sindbis Amplification in a Transposable Cassette

To test whether the Sindbis non-structural proteins and expression amplification cassette would function when permanently integrated into a host cell genome by means of transposition, a transposable reporting cassette was generated.

This comprised of flanking piggyBAC transposon terminal repeats, the thermolabile Sindbis non-structural proteins (NS1, NS2, NS3 and NS4) expressed by a CMV promoter, the Sindbis subgenomic promoter and eGFP. 293T cells were next transfected with this cassette along with an expression cassette which expresses the piggyBAC transposase. After incubation for 12 days, transient expression from the transfection is lost, so any expression remaining is due to cassette permanently transposed into the 293T cell genome. 293T cells were then incubated at either 37° C. or at 28° C. eGFP expression was determined by flow cytometery. Control cells which were either non-transfected, or non-transposed (i.e. transfected with the transposon but not the transposase) were also incubated at both temperatures and analysed.

Figure 9:
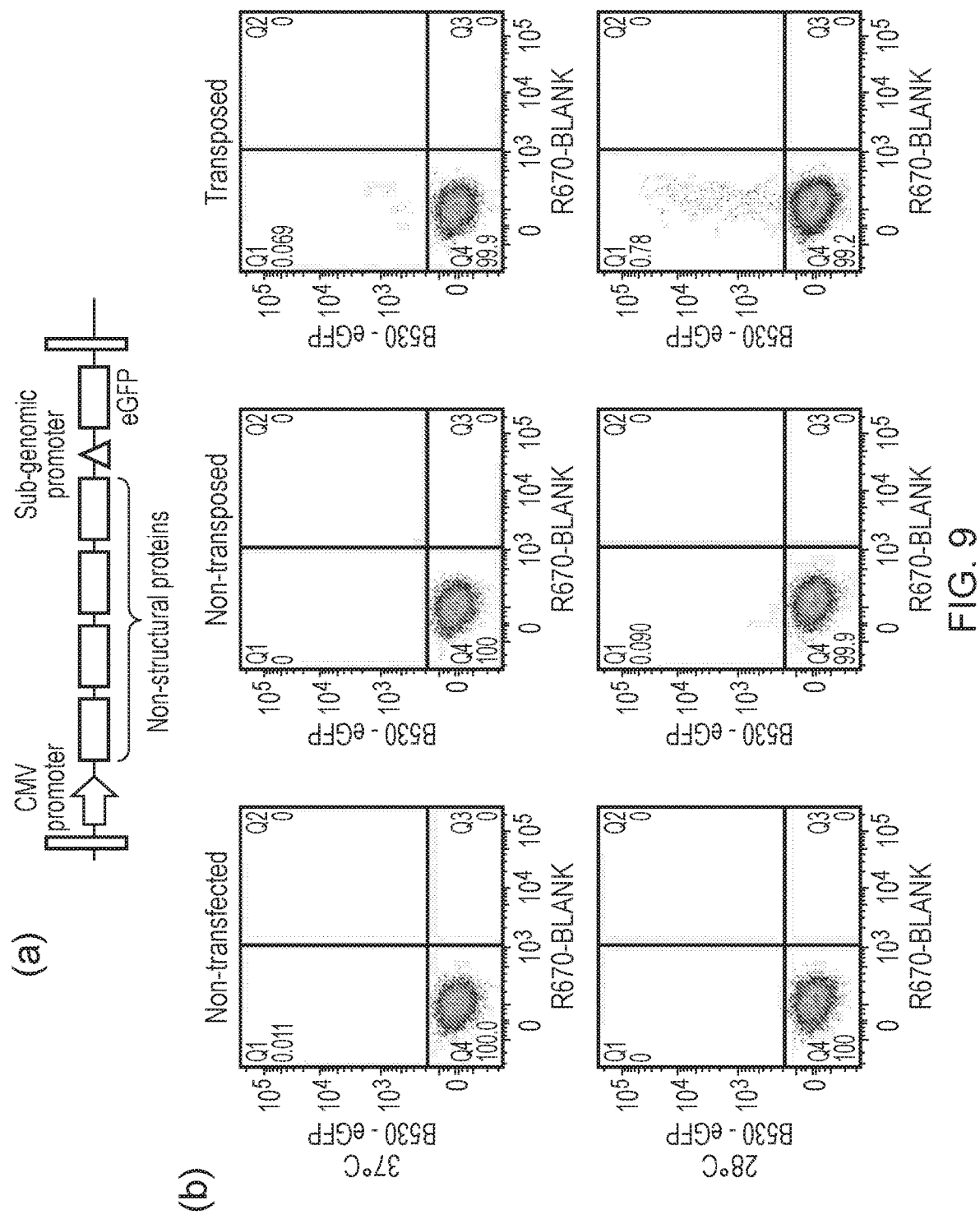
FIG. 9—Transposition of a thermolabile sindbis cassette: (a) Sindbis virus non-structural elements were cloned into a transposable cassette which is flanked on either side by piggyBAC terminal repeats. The eGFP coding sequence was cloned after the sindbis virus subgenomic promoter. (b) Flow cytometry plots of 293T cells 12 days after they were transposed with the above cassette. 293T cells were incubated either at 37° C. or at 28° C. Control 293T cells which were not transfected or which were not transposed were also tested. (c) Graphical representation of induction of eGFP expression from transposed 293T cells by incubation at 28° C.
Figure 9:
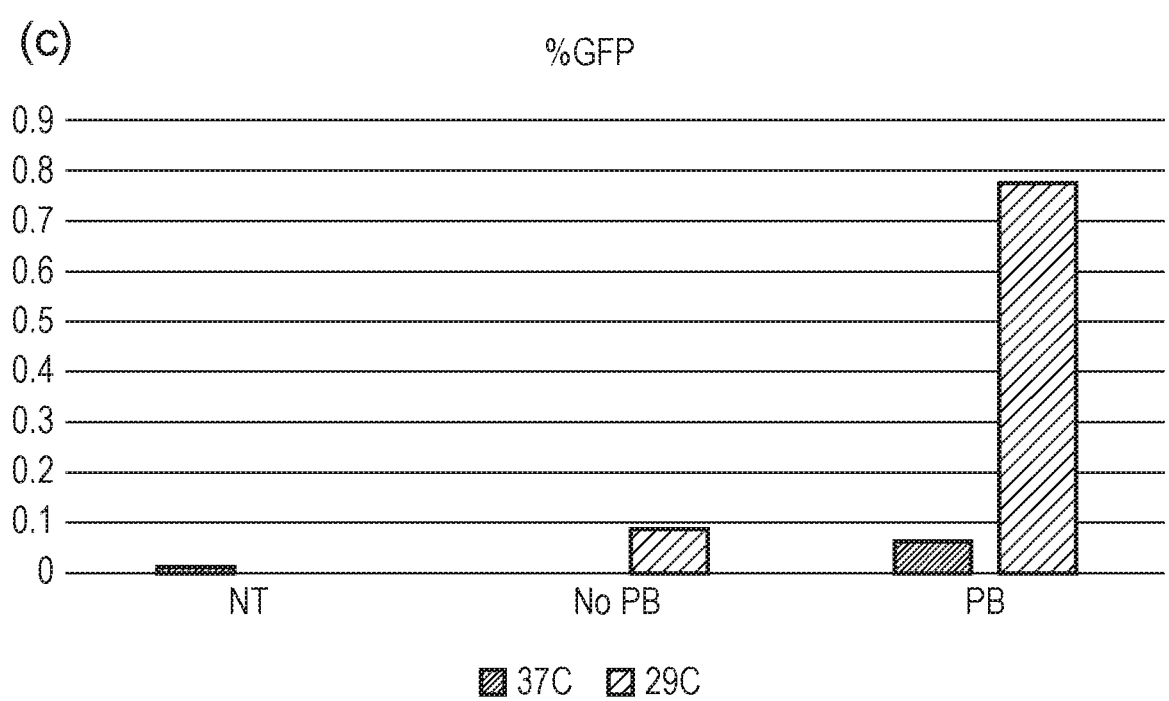

Transposed 293T cells had a 10-fold increase in eGFP expression after incubating at 28° C. see FIG. 9.

Example 5—Basal Toxicity of Gagpol in 293T Cells

One of the challenges of making a packaging cell line is that high level expression of viral transgenes is toxic to the packaging cell. While toxic effects of the VSV-G envelope are widely understood, effects of gagpol on 293T cells are not as well characterized.

To determine how difficult it is to express high-levels of gagpol in 293T cells we generated a transposable gagpol expression cassette co-expressed with a surface expressed tag (the HA tag co-expressed with the CD8 stalk and transmembrane domain) which can be detected by flow-cytometry. This tag was fused with the ZEO resistance gene.

As a control, an identical construct was made where a single amino-acid change in gagpol was made so the gapol protease was no longer active (D25A). 293T cells were transposed with these cassettes and placed under Zeocin selection.

Figure 10:
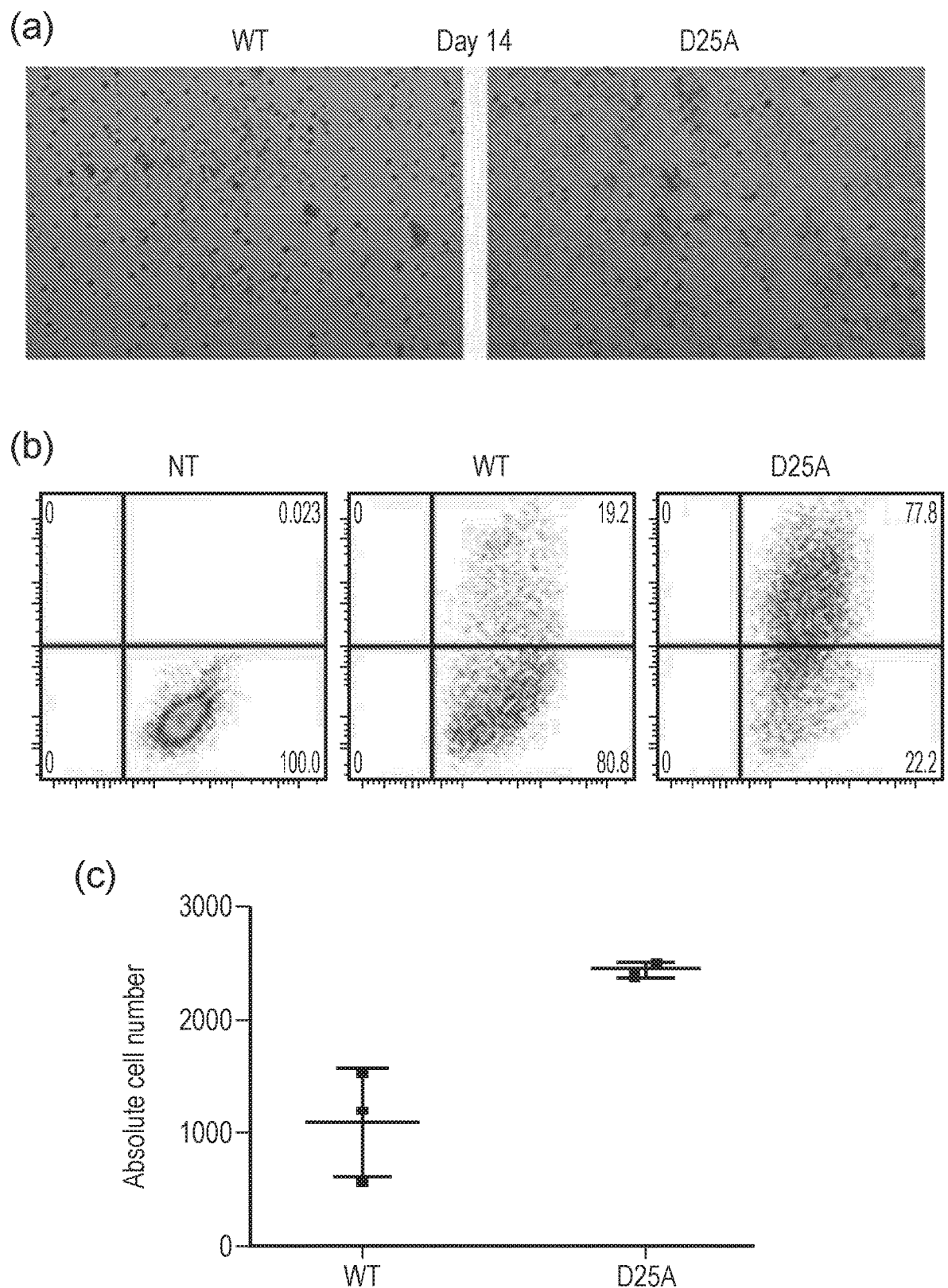
FIG. 10—Demonstration of cytopathic toxicity of lentiviral gagpol protease. 293T cells were transposed with an expression cassette expressing either wild-type gagpol, or gagpol mutated with a single amino acid substitution so that the protease is no longer active (D25A). The cassette also co-expresses a surface marker gene (HA tag on a CD8 stalk), and ZEO (the Zeomycin resistance gene). (a) photomicrographs of 293T cells transposed with gagpol and inactive gagpol constructs and plased under selection; (b) 293T cells either non-transposed or transposed with either the active gagpol construct or control and analysed for tag expression by flow-cytometery with tag expression shown on the y-axis; (c) Absolute number of 293 Ts cell either construct after Zeomycin selection.

By microscopy, most of the 293T cells transposed with the active protease developed cytopathic appearances and detached. In contrast, the 293T cells transposed with the D25A mutants appeared healthy and quickly became confluent. This visual data was quantified by flow-cytometric analysis of the proportion and absolute numbers of cells expressing transgene. Both measurements are decreased with an active protease in comparison with the mutant FIG. 10.

Example 6—Design of a Cassette to Allow Sindbis Amplification of Lentiviral Vector Transfer Cassette The entire cassette needs to be contained within the terminal repeats of a transposon—ideally one which can transpose a large payload such as PiggyBAC. A promoter which is highly active in 293T cells (such as the RSV) drives expression of the transcript which starts with the sindbis 5' CTE elements. These are located within the sindbis 5' UTR as well as part of the open reading frame reading into the first part of nsp1. Co-expressing the entire nsp complex in the same cassette may lead to a cassette which is too large and hence these proteins can be supplied in trans. The fragment of the 1$^{st}$ nsp1 will be translated but this protein fragment may be unstable and inactive.

Figure 11:
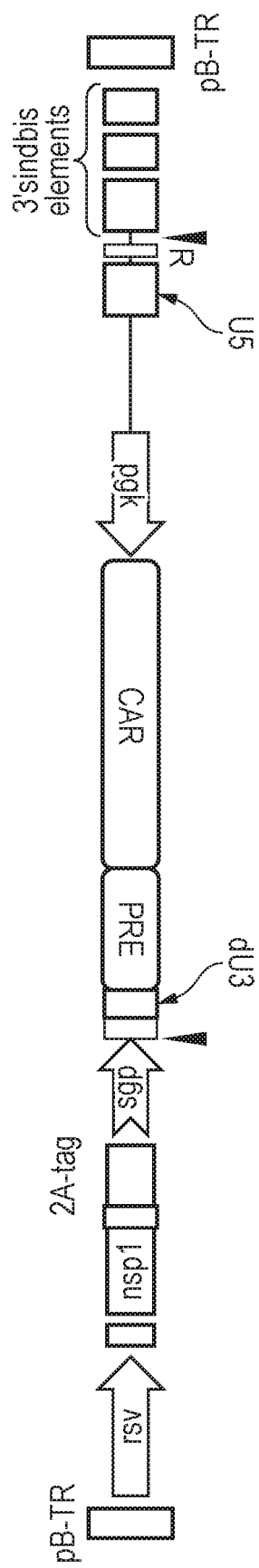
FIG. 11—Detailed design of a transposable sindbis amplifiable lentiviral transfer cassette. pB-TR: piggyBAC terminal repeat; rsv—Rous Sarcoma Virus promoter; nsp1—sindbis non-structural protein 1; 2A-tag—foot-and-mouth disease 2A peptide in frame with a surface expressed tag; sgp—subgenomic promoter; dU3—truncated LTR U3 region; PRE—woodchuck pre-processing element; CAR—chimeric antigen receptor (example transgene); pgk—phosphoglycerate kinase promoter; U5—lentiviral LTR U5 region; R—lentiviral LTR R region; 3' sindbis element—3' elements of sindbis transcript.

To allow co-expression of a marker gene a foot-and-mouth 2A like peptide is cloned in frame with the fragment of nsp1 and a tag protein is cloned in frame to the 2A. The tag protein is then expressed constitutively. Next, the sindbis subgenomic element flanks the amplification cassette. At the other end of the cassette, the sindbis 3' CTE element which includes the sindbis 3' UTR and polyadenylation signal is included. Between the subgenomic promoter and the sindbis 3' CTE the lentiviral cassette is located. This is cloned in reverse orientation so the internal promoter does not interfere with the 5' promoter of the entire cassette. The 5' LTR U3 region is truncated, and the 3' LTR U5 region is truncated. Sindbis replicon will replicate the transfer cassette into anti-sense (being sense and allowing lentiviral packaging), and sense which will act as template for further cytoplasmic amplification. See FIG. 11 which shows a schematic design of a transposable sindbis amplifiable lentiviral transfer cassette. An annotated sequence of a transposable sindbis amplifiable lentiviral transfer cassette is shown as as SEQ ID NO:16.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

---

The invention claimed is:

1. A retrovirus packaging cell which expresses a temperature sensitive RNA-dependent-RNA polymerase (RdRp), wherein the temperature sensitive RdRp comprises the sequence shown as SEQ ID NO: 2 or a variant thereof.

2. A retrovirus packaging cell according to claim 1 wherein the RdRp is encoded by a nucleic acid sequence which is stably integrated into the genome of the packaging cell.

3. A retrovirus packaging cell according to claim 1 wherein the RdRp is an alphavirus RdRp.

4. A retrovirus packaging cell according to claim 1 wherein the RdRp is a Sindbis virus RdRp.

5. A retrovirus producer cell which is a packaging cell according to claim 1 further comprising a retroviral nucleic acid transfer vector which comprises at least one RdRp promoter element which enables the retroviral nucleic acid transfer vector to be replicated by the RdRp.

6. A retrovirus producer cell according to claim 5 wherein the retroviral nucleic acid transfer vector comprises the following structure:

5'P1-rPSG-$^5$dLTR-P2-NOI-$^3$dLTR-PSG3' in which
- P1 is a eukaryotic promoter which drives transcription
- rPSG is a sequence which acts as a negative sense sub-genomic promoter for the RdRp when at the 3' end of the negative sense strand;
- $^5$dLTR is a 5' retrovirus long terminal repeat where the U3 region is non-functional;
- P2 is a eukaryotic promoter which drives expression of the NOI;
- NOI is a nucleotide sequence of interest;
- $^3$dLTR is a self-inactivating 3' retrovirus long terminal repeat with a non-functional U3;
- PSG is a sequence which acts as a sub-genomic promoter for RdRp as positive sense.

7. A retrovirus packaging cell according to claim 1 which comprises at least one retroviral helper element nucleotide sequence comprising the following structure:

5'P-rPSG-RetroP-PSG3'    i)

in which
- P is a eukaryotic promoter;
- rPSG is a sequence which acts as a negative sense sub-genomic promoter for the RdRp when at the 3' end of the negative sense strand;
- RetroP is nucleic acid sequence which encodes a retrovirus protein; and
- PSG is a sequence which acts as a sub-genomic promoter for RdRp as positive sense; or 5'P-rPSG-rRetroP-PSG3'    ii)

in which
- P is a eukaryotic promoter;
- rPSG is a sequence which acts as a negative sense sub-genomic promoter for the RdRp when at the 3' end of the negative sense strand;
- rRetroP is nucleic acid sequence which encodes a retrovirus protein in reverse orientation;
- PSG is a sequence which acts as a sub-genomic promoter for RdRp as a positive sense; or 5'P-MG-STOP-iPSG-RetroP-PSG3'    iii)

in which
- P is a eukaryotic promoter;
- MG is an open reading frame of a non-toxic marker gene;
- STOP is a stop signal;
- iPSG is a reverse-orientation RdRp sub-genomic promoter which works internally;
- RetroP is nucleic acid sequence which encodes a retrovirus protein; and
- PSG is a sequence which acts as a sub-genomic promoter for RdRp as a positive sense;

or

5'P-rPSG-MG-STOP-iPSG-RetroP-PSG3' in which
- P is a eukaryotic promoter;
- rPSG is a sequence which acts as a negative sense sub-genomic promoter for the RdRp when at the 3' end of the negative sense strand
- MG is an open reading frame of a non-toxic marker gene
- STOP is a stop signal or a series of stop signals
- iPSG is a reverse-orientation RdRp sub-genomic promoter which works internally
- RetroP is nucleic acid sequence which encodes a retrovirus protein; and
- PSG is a sequence which acts as a sub-genomic promoter for RdRp as a positive sense.

8. A retrovirus packaging cell or producer cell according to claim 1 which is a lentiviral packaging cell or a producer cell.

9. A retroviral nucleic acid transfer vector which comprises at least one RdRp promoter element which enables the retroviral nucleic acid transfer vector to be replicated by the RdRp, wherein the RdRp comprises the sequence shown as SEQ ID NO: 2 or a variant thereof.

10. A retroviral nucleic acid transfer vector of claim 9 comprising the following structure:

$$^5P1\text{-}rPSG\text{-}^5dLTR\text{-}P2\text{-}NOI\text{-}^3dLTR\text{-}PSG^{3'}$$

in which
- P1 is a eukaryotic promoter which drives transcription
- rPSG is a sequence which acts as a negative sense sub-genomic promoter for the RdRp when at the 3' end of the negative sense strand;
- $^5$dLTR is a 5' retrovirus long terminal repeat where the U3 region is non-functional;
- P2 is a eukaryotic promoter which drives expression of the NOI;
- NOI is a nucleotide sequence of interest;
- $^3$dLTR is a self-inactivating 3' retrovirus long terminal repeat with a non-functional U3;
- PSG is a sequence which acts as a sub-genomic promoter for RdRp as a positive sense.

11. A retroviral helper element nucleotide sequence comprising at least one RdRp promoter element which enables a nucleic acid sequence which encodes a retroviral protein to be replicated by the RdRp, wherein the RdRp comprises the sequence shown as SEQ ID NO: 2 or a variant thereof.

12. A plasmid comprising a retroviral nucleic acid transfer vector as defined in claim 9.

13. A method for making a packaging cell which comprises the step of introducing a nucleic acid sequence encoding a RdRp as defined in claim 1 into a cell, such that the cell expresses the RdRp.

14. A method for making a producer cell which comprises the step of introducing retroviral nucleic acid transfer vector as defined in claim 5 into a retrovirus packaging cell.

15. A method for making a retrovirus vector which comprises the step of culturing a producer cell as defined in claim 14, and isolating the retrovirus vector.

16. A method according to claim 15 which comprises culturing the producer cell at a relatively low temperature and isolating the retrovirus vector.

17. A method according to claim 15 which comprises expanding the population of producer cells by culturing the cells at a relatively high temperature and subsequently culturing the producer cells at a relatively low temperature and isolating the retrovirus vector.

18. A method for expanding a population of packaging cells or producer cells according to claim 1 by culturing the cells at a relatively high temperature.

19. A method for increasing the production of retroviral proteins in a packaging cell or producer cell according to claim 1 by decreasing the temperature of the culture medium.

* * * * *

SEQUENCE LISTING

```
<160> NUMBER OF SEQ ID NOS: 16

<210> SEQ ID NO 1
<211> LENGTH: 11581
<212> TYPE: DNA
<213> ORGANISM: Artificial Sequence
<220> FEATURE:
<223> OTHER INFORMATION: Sindbis plasmid (987SinRep) base pair sequence

<400> SEQUENCE: 1
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgatta gggtgatggt tcacgtagtg     240
ggccatcgcc ctgatagacg gttttcgcc ctttgacgtt ggagtccacg ttctttaata     300
gtggactctt gttccaaact ggaacaacac tcaaccctat ctcggtctat tcttttgatt     360
tataagggat tttgccgatt tcggcctatt ggttaaaaaa tgagctgatt taacaaaaat     420
ttaacgcgaa ttttaacaaa atattaacgc ttacaatttc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgaat tgtaatacga ctcactatag ggcgaattgg atccgaccgc     660
gaaggtcaat gccccgtaca ttcgcattcg agcacagcaa ctctccaaga gtcgacagta     720
catgtcctgg agaaaggagc ggtgacagta cactttagca ccgcgagtcc acaggcgaac     780
tttatcgtat cgctgtgtgg gctagtggat ccggagtctt atgcaatact cttgtagtct     840
```

```
tgcaacatgg taacgatgag ttagcaacat gccttacaag gagagaaaaa gcaccgtgca     900
tgccgattgg tggaagtaag gtggtacgat cgtgccttat taggaaggca acagacgggt     960
ctgacatgga ttggacgaac cactgaattc cgcattgcag agatattgta tttaagtgcc    1020
tagctcgata ccgtcgagat tgacggcgta gtacacacta ttgaatcaaa cagccgacca    1080
attgcactac catcacaatg agaaagccag tagtaaacgt agacgtagac ccccagagtc    1140
cgtttgtcgt gcaactgcaa aaagcttccc gcaatttga ggtagtagca cagcaggtca    1200
ctccaaatga ccatgctaat gccagagcat tttcgcatct ggccagtaaa ctaatcgagc    1260
tggaggttcc taccacagcg acgatcttgg acataggcag cgcaccggct cgtagaatgt    1320
tttccgagca ccagtatcat tgtgtctgcc ccatgcgtag tccagaagac ccggaccgca    1380
tgatgaaata tgccagtaaa ctggcggaaa aagcgtgcaa gattacaaac aagaacttgc    1440
atgagaagat taaggatctc cggaccgtac ttgatacgcc ggatgctgaa acaccatcgc    1500
tctgctttca caacgatgtt acctgcaaca tgcgtgccga atattccgtc atgcaggacg    1560
tgtatatcaa cgctcccgga actatctatc atcaggctat gaaaggcgtg cggaccctgt    1620
actggattgg cttcgacacc acccagttca tgttctcggc tatggcaggt tcgtaccctg    1680
cgtacaacac caactgggcc gacgagaaag tcctgaagc gcgtaacatc ggactttgca    1740
gcacaaagct gagtgaaggt aggacaggaa aattgtcgat aatgaggaag aaggagttga    1800
agcccgggtc gcgggtttat ttctccgtag gatcgacact ttatccagaa cacagagcca    1860
gcttgcagag ctggcatctt ccatcggtgt tccacttgaa tggaaagcag tcgtacactt    1920
gccgctgtga tacagtggtg agttgcgaag gctacgtagt gaagaaaatc accatcagtc    1980
ccggatcac gggagaaacc gtgggatacg cggttacaca caatagcgag gcttcttgc    2040
tatgcaaagt tactgacaca gtaaaaggag aacgggtatc gttccctgtg tgcacgtaca    2100
tcccggccac catatgcgat cagatgactg gtataatggc cacgatata tcacctgacg    2160
atgcacaaaa acttctggtt gggctcaacc agcgaattgt cattaacggt aggactaaca    2220
ggaacaccaa caccatgcaa aattaccttc tgccgatcat agcacaaggg ttcagcaaat    2280
gggctaagga gcgcaaggat gatcttgata acgagaaaat gctgggtact agagaacgca    2340
agcttacgta tggctgcttg tgggcgtttc gcactaagaa agtacattcg ttttatcgcc    2400
cacctggaac gcagacctgc gtaaaagtcc cagcctcttt tagcgctttt cccatgtcgt    2460
ccgtatggac gacctctttg cccatgtcgc tgaggcagaa attgaaactg gcattgcaac    2520
caaagaagga ggaaaaactg ctgcaggtct cggaggaatt agtcatggag gccaaggctg    2580
cttttgagga tgctcaggag gaagccagag cggagaagct ccgagaagca cttccaccat    2640
tagtggcaga caaaggcatc gaggcagccg cagaagttgt ctgcgaagtg gaggggctcc    2700
aggcggacat cggagcagca ttagttgaaa ccccgcgcgg tcacgtaagg ataataccctc    2760
aagcaaatga ccgtatgatc ggacagtata tcgttgtctc gccaaactct gtgctgaaga    2820
atgccaaact cgcaccagcg cacccgctag cagatcaggt taagatcata acacactccg    2880
gaagatcagg aagtacgcg gtcgaaccat acgacgctaa agtactgatg ccagcaggag    2940
gtgccgtacc atgccagaa ttcctagcac tgagtgagag cgccacgtta gtgtacaacg    3000
aaagagagtt tgtgaaccgc aaactatacc acattgccat gcatggcccc gccaagaata    3060
cagaagagga gcagtacaag gttacaaagg cagagcttgc agaaacagag tacgtgtttg    3120
acgtggacaa gaagcgttgc gttaagaagg aagaagcctc aggtctggtc ctctcgggag    3180
```

```
aactgaccaa ccctccctat catgagctag ctctggaggg actgaagacc cgacctgcgg    3240
tcccgtacaa ggtcgaaaca ataggagtga taggcacacc ggggtcgggc aagtcagcta    3300
ttatcaagtc aactgtcacg gcacgagatc ttgttaccag cggaaagaaa gaaaattgtc    3360
gcgaaattga ggccgacgtg ctaagactga ggggtatgca gattacgtcg aagacagtag    3420
attcggttat gctcaacgga tgccacaaag ccgtagaagt gctgtacgtt gacgaagcgt    3480
tcgcgtgcca cgcaggagca ctacttgcct tgattgctat cgtcaggccc cgcaagaagg    3540
tagtactatg cggagacccc atgcaatgcg gattcttcaa catgatgcaa ctaaaggtac    3600
atttcaatca ccctgaaaaa gacatatgca ccaagacatt ctacaagtat atctcccggc    3660
gttgcacaca gccagttaca gctattgtat cgacactgca ttacgatgga agatgaaaa    3720 ccacgaaccc gtgcaagaag aacattgaaa tcgatattac aggggccaca aagccgaagc    3780
caggggatat catcctgaca tgtttccgcg ggtgggttaa gcaattgcaa atcgactatc    3840
ccggacatga agtaatgaca gccgcggcct cacaagggct aaccagaaaa ggagtgtatg    3900
ccgtccggca aaaagtcaat gaaaacccac tgtacgcgat cacatcagag catgtgaacg    3960
tgttgctcac ccgcactgag gacaggctag tgtggaaaac cttgcagggc gacccatgga    4020
ttaagcagct cactaacata cctaaaggaa actttcaggc tactatagag gactgggaag    4080
ctgaacacaa gggaataatt gctgcaataa acagccccac tccccgtgcc aatccgttca    4140
gctgcaagac caacgtttgc tgggcgaaag cattggaacc gatactagcc acggccggta    4200
tcgtacttac cggttgccag tggagcgaac tgttcccaca gtttgcggat gacaaaccac    4260
attcggccat ttacgcctta gacgtaattt gcattaagtt tttcggcatg gacttgacaa    4320
gcggactgtt ttctaaacag agcatcccac taacgtacca tcccgccgat tcagcgaggc    4380
cggtagctca ttgggacaac agcccaggaa cccgcaagta tgggtacgat cacgccattg    4440
ccgccgaact ctcccgtaga tttccggtgt tccagctagc tgggaagggc acacaacttg    4500
atttgcagac ggggagaacc agagttatct ctgcacagca taacctggtc ccggtgaacc    4560
gcaatcttcc tcacgcctta gtccccgagt acaaggagaa gcaacccggc ccggtcgaaa    4620
aattcttgaa ccagttcaaa caccactcag tacttgtggt atcagaggaa aaaattgaag    4680
ctccccgtaa gagaatcgaa tggatcgccc cgattggcat agccggtgca gataagaact    4740
acaacctggc tttcgggttt ccgccgcagg cacggtacga cctggtgttc atcaacattg    4800
gaactaaata cagaaaccac cactttcagc agtgcgaaga ccatgcggcg accttaaaaa    4860
ccctttcgcg ttcggccctg aattgcctta acccaggagg caccctcgtg gtgaagtcct    4920
atggctacgc cgaccgcaac agtgaggacg tagtcaccgc tcttgccaga aagtttgtca    4980
gggtgtctgc agcgagacca gattgtgtct caagcaatac agaaatgtac ctgatttttc    5040
gacaactaga caacagccgt acacggcaat tcaccccgca ccatctgaat tgcgtgattt    5100
cgtccgtgta tgagggtaca agagatggag ttggagccgc gccgtcatac cgcaccaaaa    5160
gggagaatat tgctgactgt caagaggaag cagttgtcaa cgcagccaat ccgctgggta    5220
gaccaggcga aggagtctgc cgtgccatct ataaacgttg gccgaccagt tttaccgatt    5280
cagccacgga gacaggcacc gcaagaatga ctgtgtgcct aggaaagaaa gtgatccacg    5340
cggtcggccc tgatttccgg aagcacccag aagcagaagc cttgaaattg ctacaaaacg    5400
cctaccatgc agtggcagac ttagtaaatg aacataacat caagtctgtc gccattccac    5460
tgctatctac aggcatttac gcagccggaa aagaccgcct tgaagtatca cttaactgct    5520
tgacaaccgc gctagacaga actgacgcgg acgtaaccat ctattgcctg gataagaagt    5580
```

```
ggaaggaaag aatcgacgcg gcactccaac ttaaggagtc tgtaacagag ctgaaggatg    5640
aagatatgga gatcgacgat gagttagtat ggattcatcc agacagttgc ttgaagggaa    5700
gaaagggatt cagtactaca aaaggaaaat tgtattcgta cttcgaaggc accaaattcc    5760
atcaagcagc aaaagacatg gcggagataa aggtcctgtt ccctaatgac caggaaagta    5820
atgaacaact gtgtgcctac atattgggtg agaccatgga agcaatccgc gaaaagtgcc    5880
cggtcgacca taacccgtcg tctagcccgc ccaaaacgtt gccgtgcctt tgcatgtatg    5940
ccatgacgcc agaaagggtc cacagactta gaagcaataa cgtcaaagaa gttacagtat    6000
gctcctccac cccccttcct aagcacaaaa ttaagaatgt tcagaaggtt cagtgcacga    6060
aagtagtcct gtttaatccg cacactcccg cattcgttcc cgcccgtaag tacatagaag    6120
tgccagaaca gcctaccgct cctcctgcac aggccgagga ggcccccgaa gttgtagcga    6180
caccgtcacc atctacagct gataacacct cgcttgatgt cacagacatc tcactggata    6240
tggatgacag tagcgaaggc tcacttttt cgagctttag cggatcggac aactctatta    6300
ctagtatgga cagttggtcg tcaggaccta gttcactaga gatagtagac cgaaggcagg    6360
tggtggtggc tgacgttcat gccgtccaag agcctgcccc tattccaccg ccaaggctaa    6420
agaagatggc ccgcctggca gcggcaagaa aagagcccac tccaccggca agcaatagct    6480
ctgagtccct ccacctctct tttggtgggg tatccatgtc cctcggatca attttcgacg    6540
gagagacggc ccgccaggca gcggtacaac ccctggcaac aggccccacg gatgtgccta    6600
tgtctttcgg atcgttttcc gacggagaga ttgatgagct gagccgcaga gtaactgagt    6660
ccgaacccgt cctgtttgga tcatttgaac cgggcgaagt gaactcaatt atatcgtccc    6720
gatcagccgt atcttttcct ctacgcaagc agagacgtag acgcaggagc aggaggactg    6780
aatactgact aaccggggta ggtgggtaca tattttcgac ggacacaggc cctgggcact    6840
tgcaaaagaa gtccgttctg cagaaccagc ttacagaacc gaccttggag cgcaatgtcc    6900
tggaaagaat tcatgccccg gtgctcgaca cgtcgaaaga ggaacaactc aaactcaggt    6960
accagatgat gccccaccga agccaacaaa gtaggtacca gtctcgtaaa gtagaaaatc    7020
agaaagccat aaccactgag cgactactgt caggactacg actgtataac tctgccacag    7080
atcagccaga atgctataag atcacctatc cgaaaccatt gtactccagt agcgtaccgg    7140
cgaactactc cgatccacag ttcgctgtag ctgtctgtaa caactatctg catgagaact    7200
atccgacagt agcatcttat cagattactg acgagtacga tgcttacttg gatatggtag    7260
acgggacagt cgcctgcctg gatactgcaa ccttctgccc cgctaagctt agaagttacc    7320
cgaaaaaaca tgagtataga gccccgaata tccgcagtgc ggttccatca gcgatgcaga    7380
acacgctaca aaatgtgctc attgccgcaa ctaaaagaaa ttgcaacgtc acgcagatgc    7440
gtgaactgcc aacactggac tcagcgacat tcaatgtcga atgctttcga aaatatgcat    7500
gtaatgacga gtattgggag gagttcgctc ggaagccaat taggattacc actgagtttg    7560
tcaccgcata tgtagctaga ctgaaaggcc ctaaggccgc cgcactattt gcaaagacgt    7620
ataatttggt cccattgcaa gaagtgccta tggatagatt cgtcatggac atgaaaagag    7680
acgtgaaagt tacaccaggc acgaaacaca cagaagaaag accgaaagta caagtgatac    7740
aagccgcaga acccctggcg actgcttact atgcgggat tcaccgggaa ttagtgcgta    7800
ggcttacggc cgtcttgctt ccaaacattc acacgctttt tgacatgtcg gcggaggatt    7860
ttgatgcaat catagcagaa cacttcaagc aaggcgaccc ggtactggag acggatatcg    7920
```

```
catcattcga caaaagccaa gacgacgcta tggcgttaac cggtctgatg atcttggagg    7980
acctgggtgt ggatcaacca ctactcgact tgatcgagtg cgcctttgga gaaatatcat    8040
ccacccatct acctacgggt actcgtttta aattcggggc gatgatgaaa tccggaatgt    8100
tcctcacact ttttgtcaac acagttttga atgtcgttat cgccagcaga gtactagaag    8160
agcggcttaa aacgtccaga tgtgcagcgt tcattggcga cgacaacatc atacatggag    8220
tagtatctga caaagaaatg gctgagaggt gcgccacctg gctcaacatg gaggttaaga    8280
tcatcgacgc agtcatcggt gagagaccac cttacttctg cggcggattt atcttgcaag    8340
attcggttac ttccacagcg tgccgcgtgg cggatcccct gaaaaggctg tttaagttgg    8400
gtaaaccgct cccagccgac gacgagcaag acgaagacag aagacgcgct ctgctagatg    8460
aaacaaaggc gtggtttaga gtaggtataa caggcacttt agcagtggcc gtgacgaccc    8520
ggtatgaggt agacaatatt acacctgtcc tactggcatt gagaactttt gcccagagca    8580
aaagagcatt ccaagccatc agaggggaaa taaagcatct ctacggtggt cctaaatagt    8640
cagcatagta catttcatct gactaatact acaacaccac cacctctaga ccgcgccgtt    8700
cgctaccatt accagttggt ctggtgtcaa aaataataat aaccgggcag ggggatcct    8760
agacgctacg ccccaatgat ccgaccagca aaactcgatg tacttccgag gaactgatgt    8820
gcataatgca ggaattcgat atcaagctag atctcacgtg agcatgcagg ccttgggccc    8880
aatgatccga ccagcaaaac tcgatgtact tccgaggaac tgatgtgcat aatgcatcag    8940
gctggtacat tagatccccg cttaccgcgg gcaatatagc aacactaaaa actcgatgta    9000
cttccgagga agcgcagtgc ataatgctgc gcagtgttgc cacataacca ctatattaac    9060
catttatcta gcggacgcca aaaactcaat gtatttctga ggaagcgtgg tgcataatgc    9120
cacgcagcgt ctgcataact tttattattt cttttattaa tcaacaaaat tttgttttta    9180
acatttcaaa aaaaaaaaaa aaaaaaaaa aaaaaaaaa aaagggaat cccaacttg    9240
tttattgcag cttataatgg ttacaaataa agcaatagca tcacaaattt cacaaataaa    9300
gcatttttt cactgcattc tagttgtggt ttgtccaaac tcatcaatgt atcttatcat    9360
gtctggatcc gtcgagacgc gtccaattcg ccctatagtg agtcgtatta cgcgcgcttg    9420
gcgtaatcat ggtcatagct gtttcctgtg tgaaattgtt atccgctcac aattccacac    9480
aacatacgag ccggaagcat aaagtgtaaa gcctggggtg cctaatgagt gagctaactc    9540
acattaattg cgttgcgctc actgcccgct ttccagtcgg gaaacctgtc gtgccagctg    9600
cattaatgaa tcggccaacg cgcggggaga ggcggtttgc gtattgggcg ctcttccgct    9660
tcctcgctca ctgactcgct gcgctcggtc gttcggctgc ggcgagcggt atcagctcac    9720
tcaaaggcgg taatacggtt atccacagaa tcagggata acgcaggaaa gaacatgtga    9780
gcaaaaggcc agcaaaaggc caggaaccgt aaaaaggccg cgttgctggc gtttttccat    9840
aggctccgcc cccctgacga gcatcacaaa aatcgacgct caagtcagag gtggcgaaac    9900
ccgacaggac tataaagata ccaggcgttt ccccctggaa gctccctcgt gcgctctcct    9960
gttccgaccc tgccgcttac cggatacctg tccgcctttc tcccttcggg aagcgtggcg    10020
ctttctcaat gctcacgctg taggtatctc agttcggtgt aggtcgttcg ctccaagctg    10080
ggctgtgtgc acgaaccccc cgttcagccc gaccgctgcg ccttatccgg taactatcgt    10140
cttgagtcca acccggtaag acacgactta tcgccactgg cagcagccac tggtaacagg    10200
attagcagag cgaggtatgt aggcggtgct acagagttct tgaagtggtg cctaactac    10260
ggctacacta gaaggacagt atttggtatc tgcgctctgc tgaagccagt taccttcgga    10320
```

-continued

```
aaaagagttg gtagctcttg atccggcaaa caaaccaccg ctggtagcgg tggttttttt    10380
gtttgcaagc agcagattac gcgcagaaaa aaaggatctc aagaagatcc tttgatcttt    10440
tctacggggt ctgacgctca gtggaacgaa aactcacgtt aagggatttt ggtcatgaga    10500
ttatcaaaaa ggatcttcac ctagatcctt taaattaaa aatgaagttt taaatcaatc    10560
taaagtatat atgagtaaac ttggtctgac agttaccaat gcttaatcag tgaggcacct    10620
atctcagcga tctgtctatt tcgttcatcc atagttgcct gactccccgt cgtgtagata    10680
actacgatac gggagggctt accatctggc cccagtgctg caatgatacc gcgagaccca    10740
cgctcaccgg ctccagattt atcagcaata accagccag ccggaagggc cgagcgcaga    10800
agtggtcctg caactttatc cgcctccatc cagtctatta attgttgccg ggaagctaga    10860
gtaagtagtt cgccagttaa tagtttcgc aacgttgttg ccattgctac aggcatcgtg    10920
gtgtcacgct cgtcgtttgg tatggcttca ttcagctccg gttcccaacg atcaaggcga    10980
gttacatgat cccccatgtt gtgcaaaaaa gcggttagct ccttcggtcc tccgatcgtt    11040
gtcagaagta agttggccgc agtgttatca ctcatggtta tggcagcact gcataattct    11100
cttactgtca tgccatccgt aagatgcttt tctgtgactg gtgagtactc aaccaagtca    11160
ttctgagaat agtgtatgcg cgaccgagt tgctcttgcc cggcgtcaat acgggataat    11220
accgcgccac atagcagaac tttaaaagtg ctcatcattg gaaaacgttc ttcggggcga    11280
aaactctcaa ggatcttacc gctgttgaga tccagttcga tgtaacccac tcgtgcaccc    11340
aactgatctt cagcatcttt tactttcacc agcgtttctg ggtgagcaaa aacaggaagg    11400
caaaatgccg caaaaaaggg aataagggcg acacggaaat gttgaatact catactcttc    11460
ctttttcaat attattgaag catttatcag ggttattgtc tcatgagcgg atacatattt    11520
gaatgtattt agaaaaataa acaaataggg gttccgcgca catttccccg aaaagtgcca    11580
c                                                                   11581
```

<210> SEQ ID NO 2
<211> LENGTH: 2512
<212> TYPE: PRT
<213> ORGANISM: Artificial Sequence
<220> FEATURE:
<223> OTHER INFORMATION: 987.SinRep amino acid sequence with P726S
      (non-cytotoxic) and G153E (RdRp-temprature-regulated) mutations -continued Asp Ala Glu Thr Pro Ser Leu Cys Phe His Asn Asp Val Thr Cys Asn
    130                 135                 140

Met Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
            180                 185                 190

Tyr Pro Ala Tyr Asn Thr Asn Trp Ala Asp Glu Lys Val Leu Glu Ala
        195                 200                 205

Arg Asn Ile Gly Leu Cys Ser Thr Lys Leu Ser Glu Gly Arg Thr Gly
210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Asn Gly Lys Gln Ser
            260                 265                 270

Tyr Thr Cys Arg Cys Asp Thr Val Val Ser Cys Glu Gly Tyr Val Val
        275                 280                 285

Lys Lys Ile Thr Ile Ser Pro Gly Ile Thr Gly Glu Thr Val Gly Tyr
    290                 295                 300

Ala Val Thr His Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                325                 330                 335

Ala Thr Ile Cys Asp Gln Met Thr Gly Ile Met Ala Thr Asp Ile Ser
            340                 345                 350

Pro Asp Asp Ala Gln Lys Leu Leu Val Gly Leu Asn Gln Arg Ile Val
        355                 360                 365

Ile Asn Gly Arg Thr Asn Arg Asn Thr Asn Thr Met Gln Asn Tyr Leu
370                 375                 380

Leu Pro Ile Ile Ala Gln Gly Phe Ser Lys Trp Ala Lys Glu Arg Lys
385                 390                 395                 400

Asp Asp Leu Asp Asn Glu Lys Met Leu Gly Thr Arg Glu Arg Lys Leu
                405                 410                 415

Thr Tyr Gly Cys Leu Trp Ala Phe Arg Thr Lys Lys Val His Ser Phe
            420                 425                 430

Tyr Arg Pro Pro Gly Thr Gln Thr Cys Val Lys Val Pro Ala Ser Phe
        435                 440                 445

Ser Ala Phe Pro Met Ser Ser Val Trp Thr Thr Ser Leu Pro Met Ser
450                 455                 460

Leu Arg Gln Lys Leu Lys Leu Ala Leu Gln Pro Lys Lys Glu Glu Lys
465                 470                 475                 480

Leu Leu Gln Val Ser Glu Glu Leu Val Met Glu Ala Lys Ala Ala Phe
                485                 490                 495

Glu Asp Ala Gln Glu Glu Ala Arg Ala Glu Lys Leu Arg Glu Ala Leu
            500                 505                 510

Pro Pro Leu Val Ala Asp Lys Gly Ile Glu Ala Ala Glu Val Val
        515                 520                 525

Cys Glu Val Glu Gly Leu Gln Ala Asp Ile Gly Ala Ala Leu Val Glu
530                 535                 540

-continued

Thr Pro Arg Gly His Val Arg Ile Ile Pro Gln Ala Asn Asp Arg Met
545                 550                 555                 560

Ile Gly Gln Tyr Ile Val Val Ser Pro Asn Ser Val Leu Lys Asn Ala
                565                 570                 575

Lys Leu Ala Pro Ala His Pro Leu Ala Asp Gln Val Lys Ile Ile Thr
            580                 585                 590

His Ser Gly Arg Ser Gly Arg Tyr Ala Val Glu Pro Tyr Asp Ala Lys
        595                 600                 605

Val Leu Met Pro Ala Gly Gly Ala Val Pro Trp Pro Glu Phe Leu Ala
    610                 615                 620

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
                645                 650                 655

Glu Glu Gln Tyr Lys Val Thr Lys Ala Glu Leu Ala Glu Thr Glu Tyr
                660                 665                 670

Val Phe Asp Val Asp Lys Lys Arg Cys Val Lys Glu Glu Ala Ser
            675                 680                 685

Gly Leu Val Leu Ser Gly Glu Leu Thr Asn Pro Pro Tyr His Glu Leu
    690                 695                 700

Ala Leu Glu Gly Leu Lys Thr Arg Pro Ala Val Pro Tyr Lys Val Glu
705                 710                 715                 720

Thr Ile Gly Val Ile Gly Thr Pro Gly Ser Gly Lys Ser Ala Ile Ile
                725                 730                 735

Lys Ser Thr Val Thr Ala Arg Asp Leu Val Thr Ser Gly Lys Lys Glu
            740                 745                 750

Asn Cys Arg Glu Ile Glu Ala Asp Val Leu Arg Leu Arg Gly Met Gln
        755                 760                 765

Ile Thr Ser Lys Thr Val Asp Ser Val Met Leu Asn Gly Cys His Lys
    770                 775                 780

Ala Val Glu Val Leu Tyr Val Asp Glu Ala Phe Ala Cys His Ala Gly
785                 790                 795                 800

Ala Leu Leu Ala Leu Ile Ala Ile Val Arg Pro Arg Lys Lys Val Val
                805                 810                 815

Leu Cys Gly Asp Pro Met Gln Cys Gly Phe Phe Asn Met Met Gln Leu
            820                 825                 830

Lys Val His Phe Asn His Pro Glu Lys Asp Ile Cys Thr Lys Thr Phe
        835                 840                 845

Tyr Lys Tyr Ile Ser Arg Arg Cys Thr Gln Pro Val Thr Ala Ile Val
    850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
                885                 890                 895

Asp Ile Ile Leu Thr Cys Phe Arg Gly Trp Val Lys Gln Leu Gln Ile
            900                 905                 910

Asp Tyr Pro Gly His Glu Val Met Thr Ala Ala Ser Gln Gly Leu
        915                 920                 925

Thr Arg Lys Gly Val Tyr Ala Val Arg Gln Lys Val Asn Glu Asn Pro
    930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys

```
                    965             970             975
Gln Leu Thr Asn Ile Pro Lys Gly Asn Phe Gln Ala Thr Ile Glu Asp
                980             985             990

Trp Glu Ala Glu His Lys Gly Ile Ile Ala Ala Ile Asn Ser Pro Thr
                995            1000            1005

Pro Arg Ala Asn Pro Phe Ser Cys Lys Thr Asn Val Cys Trp Ala
       1010            1015            1020

Lys Ala Leu Glu Pro Ile Leu Ala Thr Ala Gly Ile Val Leu Thr
       1025            1030            1035

Gly Cys Gln Trp Ser Glu Leu Phe Pro Gln Phe Ala Asp Asp Lys
       1040            1045            1050

Pro His Ser Ala Ile Tyr Ala Leu Asp Val Ile Cys Ile Lys Phe
       1055            1060            1065

Phe Gly Met Asp Leu Thr Ser Gly Leu Phe Ser Lys Gln Ser Ile
       1070            1075            1080

Pro Leu Thr Tyr His Pro Ala Asp Ser Ala Arg Pro Val Ala His
       1085            1090            1095

Trp Asp Asn Ser Pro Gly Thr Arg Lys Tyr Gly Tyr Asp His Ala
       1100            1105            1110

Ile Ala Ala Glu Leu Ser Arg Arg Phe Pro Val Phe Gln Leu Ala
       1115            1120            1125

Gly Lys Gly Thr Gln Leu Asp Leu Gln Thr Gly Arg Thr Arg Val
       1130            1135            1140

Ile Ser Ala Gln His Asn Leu Val Pro Val Asn Arg Asn Leu Pro
       1145            1150            1155

His Ala Leu Val Pro Glu Tyr Lys Glu Lys Gln Pro Gly Pro Val
       1160            1165            1170

Glu Lys Phe Leu Asn Gln Phe Lys His His Ser Val Leu Val Val
       1175            1180            1185

Ser Glu Glu Lys Ile Glu Ala Pro Arg Lys Arg Ile Glu Trp Ile
       1190            1195            1200

Ala Pro Ile Gly Ile Ala Gly Ala Asp Lys Asn Tyr Asn Leu Ala
       1205            1210            1215

Phe Gly Phe Pro Pro Gln Ala Arg Tyr Asp Leu Val Phe Ile Asn
       1220            1225            1230

Ile Gly Thr Lys Tyr Arg Asn His His Phe Gln Gln Cys Glu Asp
       1235            1240            1245

His Ala Ala Thr Leu Lys Thr Leu Ser Arg Ser Ala Leu Asn Cys
       1250            1255            1260

Leu Asn Ser Gly Gly Thr Leu Val Val Lys Ser Tyr Gly Tyr Ala
       1265            1270            1275

Asp Arg Asn Ser Glu Asp Val Val Thr Ala Leu Ala Arg Lys Phe
       1280            1285            1290

Val Arg Val Ser Ala Ala Arg Pro Asp Cys Val Ser Ser Asn Thr
       1295            1300            1305

Glu Met Tyr Leu Ile Phe Arg Gln Leu Asp Asn Ser Arg Thr Arg
       1310            1315            1320

Gln Phe Thr Pro His His Leu Asn Cys Val Ile Ser Ser Val Tyr
       1325            1330            1335

Glu Gly Thr Arg Asp Gly Val Gly Ala Ala Pro Ser Tyr Arg Thr
       1340            1345            1350

Lys Arg Glu Asn Ile Ala Asp Cys Gln Glu Glu Ala Val Val Asn
       1355            1360            1365
```

-continued

Ala Ala Asn Pro Leu Gly Arg Pro Gly Glu Gly Val Cys Arg Ala
1370            1375                1380

Ile Tyr Lys Arg Trp Pro Thr Ser Phe Thr Asp Ser Ala Thr Glu
1385            1390                1395

Thr Gly Thr Ala Arg Met Thr Val Cys Leu Gly Lys Lys Val Ile
1400            1405                1410

His Ala Val Gly Pro Asp Phe Arg Lys His Pro Glu Ala Glu Ala
1415            1420                1425

Leu Lys Leu Leu Gln Asn Ala Tyr His Ala Val Ala Asp Leu Val
1430            1435                1440

Asn Glu His Asn Ile Lys Ser Val Ala Ile Pro Leu Leu Ser Thr
1445            1450                1455

Gly Ile Tyr Ala Ala Gly Lys Asp Arg Leu Glu Val Ser Leu Asn
1460            1465                1470

Cys Leu Thr Thr Ala Leu Asp Arg Thr Asp Ala Asp Val Thr Ile
1475            1480                1485

Tyr Cys Leu Asp Lys Lys Trp Lys Glu Arg Ile Asp Ala Ala Leu
1490            1495                1500

Gln Leu Lys Glu Ser Val Thr Glu Leu Lys Asp Glu Asp Met Glu
1505            1510                1515

Ile Asp Asp Glu Leu Val Trp Ile His Pro Asp Ser Cys Leu Lys
1520            1525                1530

Gly Arg Lys Gly Phe Ser Thr Thr Lys Gly Lys Leu Tyr Ser Tyr
1535            1540                1545

Phe Glu Gly Thr Lys Phe His Gln Ala Ala Lys Asp Met Ala Glu
1550            1555                1560

Ile Lys Val Leu Phe Pro Asn Asp Gln Glu Ser Asn Glu Gln Leu
1565            1570                1575

Cys Ala Tyr Ile Leu Gly Glu Thr Met Glu Ala Ile Arg Glu Lys
1580            1585                1590

Cys Pro Val Asp His Asn Pro Ser Ser Ser Pro Pro Lys Thr Leu
1595            1600                1605

Pro Cys Leu Cys Met Tyr Ala Met Thr Pro Glu Arg Val His Arg
1610            1615                1620

Leu Arg Ser Asn Asn Val Lys Glu Val Thr Val Cys Ser Ser Thr
1625            1630                1635

Pro Leu Pro Lys His Lys Ile Lys Asn Val Gln Lys Val Gln Cys
1640            1645                1650

Thr Lys Val Val Leu Phe Asn Pro His Thr Pro Ala Phe Val Pro
1655            1660                1665

Ala Arg Lys Tyr Ile Glu Val Pro Glu Gln Pro Thr Ala Pro Pro
1670            1675                1680

Ala Gln Ala Glu Glu Ala Pro Glu Val Val Ala Thr Pro Ser Pro
1685            1690                1695

Ser Thr Ala Asp Asn Thr Ser Leu Asp Val Thr Asp Ile Ser Leu
1700            1705                1710

Asp Met Asp Asp Ser Ser Glu Gly Ser Leu Phe Ser Ser Phe Ser
1715            1720                1725

Gly Ser Asp Asn Ser Ile Thr Ser Met Asp Ser Trp Ser Ser Gly
1730            1735                1740

Pro Ser Ser Leu Glu Ile Val Asp Arg Arg Gln Val Val Val Ala
1745            1750                1755

```
Asp Val His Ala Val Gln Glu Pro Ala Pro Ile Pro Pro Pro Arg
    1760                1765                1770

Leu Lys Lys Met Ala Arg Leu Ala Ala Ala Arg Lys Glu Pro Thr
    1775                1780                1785

Pro Pro Ala Ser Asn Ser Ser Glu Ser Leu His Leu Ser Phe Gly
    1790                1795                1800

Gly Val Ser Met Ser Leu Gly Ser Ile Phe Asp Gly Glu Thr Ala
    1805                1810                1815

Arg Gln Ala Ala Val Gln Pro Leu Ala Thr Gly Pro Thr Asp Val
    1820                1825                1830

Pro Met Ser Phe Gly Ser Phe Ser Asp Gly Glu Ile Asp Glu Leu
    1835                1840                1845

Ser Arg Arg Val Thr Glu Ser Glu Pro Val Leu Phe Gly Ser Phe
    1850                1855                1860

Glu Pro Gly Glu Val Asn Ser Ile Ile Ser Ser Arg Ser Ala Val
    1865                1870                1875

Ser Phe Pro Leu Arg Lys Gln Arg Arg Arg Arg Ser Arg Arg
    1880                1885                1890

Thr Glu Tyr Leu Thr Gly Val Gly Gly Tyr Ile Phe Ser Thr Asp
    1895                1900                1905

Thr Gly Pro Gly His Leu Gln Lys Lys Ser Val Leu Gln Asn Gln
    1910                1915                1920

Leu Thr Glu Pro Thr Leu Glu Arg Asn Val Leu Glu Arg Ile His
    1925                1930                1935

Ala Pro Val Leu Asp Thr Ser Lys Glu Glu Gln Leu Lys Leu Arg
    1940                1945                1950

Tyr Gln Met Met Pro Thr Glu Ala Asn Lys Ser Arg Tyr Gln Ser
    1955                1960                1965

Arg Lys Val Glu Asn Gln Lys Ala Ile Thr Thr Glu Arg Leu Leu
    1970                1975                1980

Ser Gly Leu Arg Leu Tyr Asn Ser Ala Thr Asp Gln Pro Glu Cys
    1985                1990                1995

Tyr Lys Ile Thr Tyr Pro Lys Pro Leu Tyr Ser Ser Val Pro
    2000                2005                2010

Ala Asn Tyr Ser Asp Pro Gln Phe Ala Val Ala Val Cys Asn Asn
    2015                2020                2025

Tyr Leu His Glu Asn Tyr Pro Thr Val Ala Ser Tyr Gln Ile Thr
    2030                2035                2040

Asp Glu Tyr Asp Ala Tyr Leu Asp Met Val Asp Glu Thr Val Ala
    2045                2050                2055

Cys Leu Asp Thr Ala Thr Phe Cys Pro Ala Lys Leu Arg Ser Tyr
    2060                2065                2070

Pro Lys Lys His Glu Tyr Arg Ala Pro Asn Ile Arg Ser Ala Val
    2075                2080                2085

Pro Ser Ala Met Gln Asn Thr Leu Gln Asn Val Leu Ile Ala Ala
    2090                2095                2100

Thr Lys Arg Asn Cys Asn Val Thr Gln Met Arg Glu Leu Pro Thr
    2105                2110                2115

Leu Asp Ser Ala Thr Phe Asn Val Glu Cys Phe Arg Lys Tyr Ala
    2120                2125                2130

Cys Asn Asp Glu Tyr Trp Glu Glu Phe Ala Arg Lys Pro Ile Arg
    2135                2140                2145

Ile Thr Thr Glu Phe Val Thr Ala Tyr Val Ala Arg Leu Lys Gly
```

2150                2155                2160
Pro Lys Ala Ala Ala Leu Phe Ala Lys Thr Tyr Asn Leu Val Pro
    2165                2170                2175

Leu Gln Glu Val Pro Met Asp Arg Phe Val Met Asp Met Lys Arg
    2180                2185                2190

Asp Val Lys Val Thr Pro Gly Thr Lys His Thr Glu Glu Arg Pro
    2195                2200                2205

Lys Val Gln Val Ile Gln Ala Ala Glu Pro Leu Ala Thr Ala Tyr
    2210                2215                2220

Leu Cys Gly Ile His Arg Glu Leu Val Arg Arg Leu Thr Ala Val
    2225                2230                2235

Leu Leu Pro Asn Ile His Thr Leu Phe Asp Met Ser Ala Glu Asp
    2240                2245                2250

Phe Asp Ala Ile Ile Ala Glu His Phe Lys Gln Gly Asp Pro Val
    2255                2260                2265

Leu Glu Thr Asp Ile Ala Ser Phe Asp Lys Ser Gln Asp Asp Ala
    2270                2275                2280

Met Ala Leu Thr Gly Leu Met Ile Leu Glu Asp Leu Gly Val Asp
    2285                2290                2295

Gln Pro Leu Leu Asp Leu Ile Glu Cys Ala Phe Gly Glu Ile Ser
    2300                2305                2310

Ser Thr His Leu Pro Thr Gly Thr Arg Phe Lys Phe Gly Ala Met
    2315                2320                2325

Met Lys Ser Gly Met Phe Leu Thr Leu Phe Val Asn Thr Val Leu
    2330                2335                2340

Asn Val Val Ile Ala Ser Arg Val Leu Glu Glu Arg Leu Lys Thr
    2345                2350                2355

Ser Arg Cys Ala Ala Phe Ile Gly Asp Asp Asn Ile Ile His Gly
    2360                2365                2370

Val Val Ser Asp Lys Glu Met Ala Glu Arg Cys Ala Thr Trp Leu
    2375                2380                2385

Asn Met Glu Val Lys Ile Ile Asp Ala Val Ile Gly Glu Arg Pro
    2390                2395                2400

Pro Tyr Phe Cys Gly Gly Phe Ile Leu Gln Asp Ser Val Thr Ser
    2405                2410                2415

Thr Ala Cys Arg Val Ala Asp Pro Leu Lys Arg Leu Phe Lys Leu
    2420                2425                2430

Gly Lys Pro Leu Pro Ala Asp Asp Glu Gln Asp Glu Asp Arg Arg
    2435                2440                2445

Arg Ala Leu Leu Asp Glu Thr Lys Ala Trp Phe Arg Val Gly Ile
    2450                2455                2460

Thr Gly Thr Leu Ala Val Ala Val Thr Thr Arg Tyr Glu Val Asp
    2465                2470                2475

Asn Ile Thr Pro Val Leu Leu Ala Leu Arg Thr Phe Ala Gln Ser
    2480                2485                2490

Lys Arg Ala Phe Gln Ala Ile Arg Gly Glu Ile Lys His Leu Tyr
    2495                2500                2505

Gly Gly Pro Lys
    2510

<210> SEQ ID NO 3
<211> LENGTH: 239
<212> TYPE: PRT
<213> ORGANISM: Artificial Sequence

```
<220> FEATURE:
<223> OTHER INFORMATION: eGFP amino acid sequence

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 4
<211> LENGTH: 511
<212> TYPE: PRT
<213> ORGANISM: Artificial Sequence
<220> FEATURE:
<223> OTHER INFORMATION: VSV-G (glycoprotein G of the Vesicular
      stomatitis virus (VSV)) amino acid sequence

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95
```

```
Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```

<210> SEQ ID NO 5
<211> LENGTH: 4307
<212> TYPE: DNA
<213> ORGANISM: Artificial Sequence
<220> FEATURE:
<223> OTHER INFORMATION: Gag.Pol DNA sequence

<400> SEQUENCE: 5

| | | | | | |
|---|---|---|---|---|---|
| atgggagcac | gggctagtgt | tctttctgga | ggtgagcttg | acaggtggga | gaagatcaga | 60 |
| ctgcgccccg | gcggcaaaaa | gaagtacaag | ctgaagcaca | tcgtgtgggc | ctctcgcgaa | 120 |
| ttggagaggt | ttgccgtgaa | ccccgggctc | ctggagacaa | gcgaggggtg | ccggcagatc | 180 |
| ctcggccaat | gcagcccag | tttgcaaacc | ggcagcgagg | agttgcggag | cctgtacaac | 240 |
| accgtggcca | cattgtactg | cgtccaccag | cgcatcgaaa | tcaaggatac | aaaagaggcc | 300 |
| ctggataaaa | tcgaagagga | acagaataag | agcaaaaaga | aggcccaaca | agccgccgct | 360 |
| gataccggcc | attctaacca | agtgtctcag | aactatccca | tcgtccaaaa | tattcaaggc | 420 |
| cagatggtcc | accaagctat | cagccccgg | accctgaacg | cctgggtgaa | ggtggtggag | 480 |
| gaaaaagcct | tttctcccga | ggtcatccct | atgttcagcg | ccctgagcga | gggcgctaca | 540 |
| ccccaggacc | tgaatacaat | gttgaatacc | gtcggcggcc | accaggccgc | tatgcagatg | 600 |
| ctgaaggaaa | caattaacga | agaggccgcc | gagtgggacc | gggtccaccc | cgtccaggct | 660 |
| ggccccatcg | cacccgggca | aatgcgggag | ccgagaggct | ccgatatcgc | cggcaccacc | 720 |
| tccacattgc | aagagcagat | cggctggatg | accaacaatc | cccaattcc | cgtgggcgag | 780 |
| atctacaagc | ggtggatcat | tctcggcctg | aacaagatcg | tgcggatgta | ctctcccaca | 840 |
| tctatcctcg | atatccggca | gggccccaaa | gagccttcc | gggattacgt | ggatagattt | 900 |
| tacaagacct | tgcgggctga | caggccagc | caagaagtga | gaactggat | gacggagaca | 960 |
| ctcctcgtgc | agaacgccaa | tcccgactgc | aaaaccatcc | tgaaggcctt | gggcccagcc | 1020 |
| gccaccttgg | aggagatgat | gaccgcctgc | caaggcgtgg | gaggccctgg | cacaaagcc | 1080 |
| cgggtgctcg | ccgaggccat | gtctcaggtg | accaacagcg | ccacaatcat | gatgcaacgg | 1140 |
| gggaacttcc | gcaatcagcg | gaaaatcgtg | aaatgcttta | actgtggcaa | agaagggcac | 1200 |
| acagcccgca | actgcagggc | ccctaggaaa | agggctgtt | ggaaatgtgg | aaaggaagga | 1260 |
| caccaaatga | agattgtac | tgagagacag | gctaattttt | tagggaagat | ctggccttcc | 1320 |
| cacaagggaa | ggccagggaa | ttttcttcag | agcagaccag | agccaacagc | cccaccagaa | 1380 |
| gagagcttca | ggtttgggga | agagacaaca | actccctctc | agaagcagga | gccgatagac | 1440 |
| aaggaactgt | atcctttagc | ttccctcaga | tcactctttg | gcagcgaccc | ctcgtcacaa | 1500 |
| taaagatagg | ggggcagctc | aaggaggctc | tcctggccac | cggagcagac | gacaccgtgc | 1560 |
| tggaggagat | gtcactccct | ggtcggtgga | agcctaagat | gattggtggt | ataggggct | 1620 |
| tcattaaggt | gcggcaatac | gaccaaatct | tgatcgagat | ttgcggccac | aaggccatcg | 1680 |
| gcaccgtgct | ggtgggcccc | acccccgtga | atatcatcgg | ccgaaccctc | ctcacccaaa | 1740 |
| tcggctgtac | cctgaacttc | cctatctctc | ccatcgaaac | cgtgcccgtg | aagctgaaac | 1800 |
| ccggcatgga | cggcccaag | gtgaagcagt | ggcccctcac | cgaggagaag | atcaaggccc | 1860 |
| tggtggagat | ctgcaccgaa | atggagaaag | agggcaagat | cagcaagatc | ggccccgaga | 1920 |
| acccctataa | cacccccgtg | ttcgctatca | aaaagaagga | ttccaccaag | tggcggaagc | 1980 |
| tggtggactt | cgggagttg | aacaaacgga | cccaggattt | tgggaggtg | cagctgggca | 2040 |
| tcccccaccc | tgccggcctg | aagaaaaaga | agagcgtgac | cgtgctcgac | gtcggcgacg | 2100 |

```
cctacttcag cgtgcctctg gacgaggatt ttcgcaaata caccgccttc acaatcccct   2160
ccatcaataa cgaaaccccc ggcatccggt accaatataa cgtcttgccc caaggctgga   2220
agggcagccc cgccatcttt cagtcctcta tgaccaagat tctggaaccc ttccggaagc   2280
agaaccccga tatcgtgatt taccagtata tggacgacct ctacgtgggc agcgatctgg   2340
agatcggcca acaccggacc aagatcgaag aactccggca gcacctcctc cgctggggct   2400
tgacaacccc cgataagaag caccaaaagg agcctcccct tttgtggatg ggctacgagt   2460
tgcaccccga caagtggacc gtgcaaccca tcgtcctccc cgagaaggat tcttggaccg   2520
tgaacgatat ccaaaaactg gtcggcaagc tcaactgggc ctcccaaatc tatcccggca   2580
tcaaggtgcg ccagctgtgc aagttgttgc ggggcacaaa ggcgttgacc gaggtgatcc   2640
ccttgaccga ggaggccgaa ttggagctcg ccgagaatcg ggaaatcttg aaggagcccg   2700
tgcacggcgt ctactacgat cccagcaagg atctgatcgc cgagatccaa aaacaaggcc   2760
aggggcagtg gacctaccag atctaccagg aacccttcaa gaacctcaag accggcaagt   2820
acgcccggat gagaggcgcc cataccacg acgtgaagca gctgaccgaa gccgtccaga   2880
agatcacaac cgagtctatc gtgatctggg gcaaaacccc caagttcaag ctccctatcc   2940
agaaggaaac gtgggaaacc tggtggaccg aatactggca ggctacatgg attcccgaat   3000
gggagttcgt gaacacaccc cctctggtca agctgtggta tcaactggaa aaggagccta   3060
tcgtgggcgc cgagacattt tacgtggacg gcgctgccaa tcgcgaaacc aagctgggca   3120
aggccggcta cgtgaccaat cggggccgcc agaaggtggt gacattgacc gataccacca   3180
accagaaaac cgaactgcag gccatctact tggccctcca agacagcggc ctggaggtga   3240
atatcgtgac cgatagccag tacgccctgg gcattatcca ggcccagccc gaccagtccg   3300
agagcgaact ggtgaaccag atcatcgaac aactgatcaa gaaagagaaa gtgtacctcg   3360
cctgggtgcc cgcccataag gggatcggcg gcaacgagca ggtggacaag ctggtgtccg   3420
ccggcattcg caaggtgttg ttcctggacg gcatcgacaa agctcaggac gagcacgaaa   3480
agtaccattc caactggcgg gccatggcct ccgacttcaa tttgccaccc gtggtggcca   3540
aggagatcgt ggcttcttgc gacaagtgcc aattgaaggg cgaggctatg cacggccagg   3600
tggattgctc ccccggcatc tggcagttgg actgcaccca cctggagggc aaggtgattc   3660
tcgtggccgt gcacgtggct tccggctaca tcgaggctga ggtgatcccg gccgaaaccg   3720
gccaagagac tgcctacttc ttgctgaagc tggccggcag gtggcccgta aagaccatcc   3780
acaccgataa cgggtctaac tttacatccg ccaccgtgaa agctgcttgc tggtgggcag   3840
gcattaaaca agagttcggc atcccttata accctcagtc ccagggcgtg gtggagagca   3900
tgaacaagga gctgaaaaag atcatcggcc aagtgcggga ccaagccgag cacttgaaaa   3960
ccgccgtgca gatggccgtg tttattcata acttcaagcg gaagggcggc atcggcggct   4020
attccgccgg tgagcggatc gtggatatca tcgccaccga tatccagacc aaggagctgc   4080
agaagcagat caccaagatc cagaacttca gagtgtacta tcgcgattct cggaaccccct   4140 tgtggaaggg gccagccaaa ttgttgtgga ggggaggg cgccgtggtg atccaggaca   4200
actccgatat caaggtggtc ccgcggagga aggccaaaat tatccgcgac tacggcaagc   4260
aaatggccgg cgacgactgc gtcgcctccc ggcaagacga ggactga         4307
```

<210> SEQ ID NO 6
<211> LENGTH: 5332
<212> TYPE: DNA
<213> ORGANISM: Artificial Sequence
<220> FEATURE:
<223> OTHER INFORMATION: nucleic acid sequence which encodes nsp1234 of a Sindbis virus

<400> SEQUENCE: 6

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgaat tgtaatacga ctcactatag ggcgaattgg atccgaccgc    660
gaaggtcaat gccccgtaca ttcgcattcg agcacagcaa ctctccaaga gtcgacagta    720
catgtcctgg agaaaggagc ggtgacagta cactttagca ccgcgagtcc acaggcgaac    780
tttatcgtat cgctgtgtgg gctagtggat ccggagtctt atgcaatact cttgtagtct    840
tgcaacatgg taacgatgag ttagcaacat gccttacaag gagagaaaaa gcaccgtgca    900
tgccgattgg tggaagtaag gtggtacgat cgtgccttat taggaaggca acagacgggt    960
ctgacatgga ttggacgaac cactgaattc cgcattgcag agatattgta tttaagtgcc   1020
tagctcgata ccgtcgagat tgacggcgta gtacacacta ttgaatcaaa cagccgacca   1080
attgcactac catcacaatg gagaagccag tagtaaacgt agacgtagac ccccagagtc   1140
cgtttgtcgt gcaactgcaa aaaagcttcc cgcaatttga ggtagtagca cagcaggtca   1200
ctccaaatga ccatgctaat gccagagcat tttcgcatct ggccagtaaa ctaatcgagc   1260
tggaggttcc taccacagcg acgatcttgg acataggcag cgcaccggct cgtagaatgt   1320
tttccgagca ccagtatcat tgtgtctgcc ccatgcgtag tccagaagac ccggaccgca   1380
tgatgaaata tgccagtaaa ctggcggaaa aagcgtgcaa gattacaaac aagaacttgc   1440
atgagaagat taaggatctc cggaccgtac ttgatacgcc ggatgctgaa acaccatcgc   1500
tctgctttca caacgatgtt acctgcaaca tgcgtgccga atattccgtc atgcaggacg   1560
tgtatatcaa cgctcccgga actatctatc atcaggctat gaaaggcgtg cggaccctgt   1620
actggattgg cttcgacacc acccagttca tgttctcggc tatggcaggt tcgtaccctg   1680
cgtacaacac caactgggcc gacgagaaag tccttgaagc gcgtaacatc ggactttgca   1740
gcacaaagct gagtgaaggt aggacaggaa aattgtcgat aatgaggaag aaggagttga   1800
agcccgggtc gcgggtttat ttctccgtag gatcgacact ttatccagaa cacagagcca   1860
gcttgcagag ctggcatctt ccatcggtgt tccacttgaa tggaaagcag tcgtacactt   1920
gccgctgtga tacagtggtg agttgcgaag gctacgtagt gaagaaaatc accatcagtc   1980
ccgggatcac gggagaaacc gtgggatacg cggttacaca caatagcgag ggcttcttgc   2040
tatgcaaagt tactgacaca gtaaaaggag aacgggtatc gttccctgtg tgcacgtaca   2100
tcccggccac catatgcgat cagatgactg gtataatggc cacggatata tcacctgacg   2160
atgcacaaaa acttctggtt gggctcaacc agcgaattgt cattaacggt aggactaaca   2220
```

```
ggaacaccaa caccatgcaa aattaccttc tgccgatcat agcacaaggg ttcagcaaat    2280
gggctaagga gcgcaaggat gatcttgata acgagaaaat gctgggtact agagaacgca    2340
agcttacgta tggctgcttg tgggcgtttc gcactaagaa agtacattcg ttttatcgcc    2400
cacctggaac gcagacctgc gtaaaagtcc cagcctcttt tagcgctttt cccatgtcgt    2460
ccgtatggac gacctctttg cccatgtcgc tgaggcagaa attgaaactg cattgcaac     2520 caaagaagga ggaaaaactg ctgcaggtct cggaggaatt agtcatggag gccaaggctg    2580
cttttgagga tgctcaggag gaagccagag cggagaagct ccgagaagca cttccaccat    2640
tagtggcaga caaaggcatc gaggcagccg cagaagttgt ctgcgaagtg gaggggctcc    2700
aggcggacat cggagcagca ttagttgaaa ccccgcgcgg tcacgtaagg ataataccct    2760
aagcaaatga ccgtatgatc ggacagtata tcgttgtctc gccaaactct gtgctgaaga    2820
atgccaaact cgcaccagcg cacccgctag cagatcaggt taagatcata acacactccg    2880
gaagatcagg aaggtacgcg gtcgaaccat acgacgctaa agtactgatg ccagcaggag    2940
gtgccgtacc atggccagaa ttcctagcac tgagtgagag cgccacgtta gtgtacaacg    3000
aaagagagtt tgtgaaccgc aaactatacc acattgccat gcatggcccc gccaagaata    3060
cagaagagga gcagtacaag gttacaaagg cagagcttgc agaaacagag tacgtgtttg    3120
acgtggacaa gaagcgttgc gttaagaagg aagaagcctc aggtctggtc ctctcgggag    3180
aactgaccaa ccctccctat catgagctag ctctggaggg actgaagacc cgacctgcgg    3240
tcccgtacaa ggtcgaaaca ataggagtga taggcacacc ggggtcgggc aagtcagcta    3300
ttatcaagtc aactgtcacg gcacgagatc ttgttaccag cggaaagaaa gaaaattgtc    3360
gcgaaattga ggccgacgtg ctaagactga ggggtatgca gattacgtcg aagacagtag    3420
attcggttat gctcaacgga tgccacaaag ccgtagaagt gctgtacgtt gacgaagcgt    3480
tcgcgtgcca cgcaggagca ctacttgcct tgattgctat cgtcaggccc cgcaagaagg    3540
tagtactatg cggagacccc atgcaatgcg gattcttcaa catgatgcaa ctaaaggtac    3600
atttcaatca ccctgaaaaa gacatatgca ccaagacatt ctacaagtat atctcccggc    3660
gttgcacaca gccagttaca gctattgtat cgacactgca ttacgatgga aagatgaaaa    3720
ccacgaaccc gtgcaagaag aacattgaaa tcgatattac aggggccaca aagccgaagc    3780
caggggatat catcctgaca tgtttccgcg ggtgggttaa gcaattgcaa atcgactatc    3840
ccggacatga agtaatgaca gccgcggcct cacaagggct aaccagaaaa ggagtgtatg    3900
ccgtccggca aaaagtcaat gaaaacccac tgtacgcgat cacatcagag catgtgaacg    3960
tgttgctcac ccgcactgag gacaggctag tgtggaaaac cttgcagggc gacccatgga    4020
ttaagcagct cactaacata cctaaaggaa actttcaggc tactatagag gactgggaag    4080
ctgaacacaa gggaataatt gctgcaataa acagccccac tccccgtgcc aatccgttca    4140
gctgcaagac caacgtttgc tgggcgaaag cattggaacc gatactagcc acggccggta    4200
tcgtacttac cggttgccag tggagcgaac tgttcccaca gtttgcggat gacaaaccac    4260
attcggccat ttacgcctta gacgtaattt gcattaagtt tttcggcatg gacttgacaa    4320
gcggactgtt ttctaaacag agcatccac taacgtacca tccccgccgat tcagcgaggc    4380 cggtagctca ttgggacaac agcccaggaa cccgcaagta tgggtacgat cacgccattg    4440
ccgccgaact ctcccgtaga tttcggtgt tccagctagc tgggaagggc acacaacttg    4500
atttgcagac ggggagaacc agagttatct ctgcacagca taacctggtc ccggtgaacc    4560
```

```
gcaatcttcc tcacgcctta gtccccgagt acaaggagaa gcaacccggc ccggtcgaaa    4620
aattcttgaa ccagttcaaa caccactcag tacttgtggt atcagaggaa aaaattgaag    4680
ctccccgtaa gagaatcgaa tggatcgccc cgattggcat agccggtgca gataagaact    4740
acaacctggc tttcgggttt ccgccgcagg cacggtacga cctggtgttc atcaacattg    4800
gaactaaata cagaaaccac cactttcagc agtgcgaaga ccatgcggcg accttaaaaa    4860
ccctttcgcg ttcggccctg aattgcctta acccaggagg caccctcgtg gtgaagtcct    4920
atggctacgc cgaccgcaac agtgaggacg tagtcaccgc tcttgccaga aagtttgtca    4980
gggtgtctgc agcgagacca gattgtgtct caagcaatac agaaatgtac ctgattttcc    5040
gacaactaga caacagccgt acacggcaat tcaccccgca ccatctgaat tgcgtgattt    5100
cgtccgtgta tgagggtaca agagatggag ttggagccgc gccgtcatac cgcaccaaaa    5160
gggagaatat tgctgactgt caagaggaag cagttgtcaa cgcagccaat ccgctgggta    5220
gaccaggcga aggagtctgc cgtgccatct ataaacgttg gccgaccagt tttaccgatt    5280
cagccacgga gacaggcacc gcaagaatga ctgtgtgcct aggaaagaaa gt            5332
```

<210> SEQ ID NO 7
<211> LENGTH: 540
<212> TYPE: PRT
<213> ORGANISM: Artificial Sequence
<220> FEATURE:
<223> OTHER INFORMATION: nsp1 polypeptide

<400> SEQUENCE: 7

```
Met Glu Lys Pro Val Val Asn Val Asp Pro Gln Ser Pro Phe
1               5                   10                  15

Val Val Gln Leu Gln Lys Ser Phe Pro Gln Phe Glu Val Val Ala Gln
                20                  25                  30

Gln Val Thr Pro Asn Asp His Ala Asn Ala Arg Ala Phe Ser His Leu
            35                  40                  45

Ala Ser Lys Leu Ile Glu Leu Glu Val Pro Thr Thr Ala Thr Ile Leu
        50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140

Met Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
            180                 185                 190

Tyr Pro Ala Tyr Asn Thr Asn Trp Ala Asp Glu Lys Val Leu Glu Ala
        195                 200                 205

Arg Asn Ile Gly Leu Cys Ser Thr Lys Leu Ser Glu Gly Arg Thr Gly
    210                 215                 220

Lys Leu Ser Ile Met Arg Lys Lys Glu Leu Lys Pro Gly Ser Arg Val
```

```
            225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Asn Gly Lys Gln Ser
            260                 265                 270

Tyr Thr Cys Arg Cys Asp Thr Val Ser Cys Glu Gly Tyr Val Val
        275                 280                 285

Lys Lys Ile Thr Ile Ser Pro Gly Ile Thr Gly Glu Thr Val Gly Tyr
        290                 295                 300

Ala Val Thr His Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                325                 330                 335

Ala Thr Ile Cys Asp Gln Met Thr Gly Ile Met Ala Thr Asp Ile Ser
            340                 345                 350

Pro Asp Asp Ala Gln Lys Leu Leu Val Gly Leu Asn Gln Arg Ile Val
        355                 360                 365

Ile Asn Gly Arg Thr Asn Arg Asn Thr Asn Thr Met Gln Asn Tyr Leu
        370                 375                 380

Leu Pro Ile Ile Ala Gln Gly Phe Ser Lys Trp Ala Lys Glu Arg Lys
385                 390                 395                 400

Asp Asp Leu Asp Asn Glu Lys Met Leu Gly Thr Arg Glu Arg Lys Leu
                405                 410                 415

Thr Tyr Gly Cys Leu Trp Ala Phe Arg Thr Lys Lys Val His Ser Phe
            420                 425                 430

Tyr Arg Pro Pro Gly Thr Gln Thr Cys Val Lys Val Pro Ala Ser Phe
        435                 440                 445

Ser Ala Phe Pro Met Ser Ser Val Trp Thr Thr Ser Leu Pro Met Ser
        450                 455                 460

Leu Arg Gln Lys Leu Lys Leu Ala Leu Gln Pro Lys Lys Glu Glu Lys
465                 470                 475                 480

Leu Leu Gln Val Ser Glu Glu Leu Val Met Glu Ala Lys Ala Ala Phe
                485                 490                 495

Glu Asp Ala Gln Glu Glu Ala Arg Ala Glu Lys Leu Arg Glu Ala Leu
            500                 505                 510

Pro Pro Leu Val Ala Asp Lys Gly Ile Glu Ala Ala Glu Val Val
        515                 520                 525

Cys Glu Val Glu Gly Leu Gln Ala Asp Ile Gly Ala
        530                 535                 540

<210> SEQ ID NO 8
<211> LENGTH: 807
<212> TYPE: PRT
<213> ORGANISM: Artificial Sequence
<220> FEATURE:
<223> OTHER INFORMATION: nsp2 polypeptide

<400> SEQUENCE: 8

Ala Leu Val Glu Thr Pro Arg Gly His Val Arg Ile Ile Pro Gln Ala
1               5                   10                  15

Asn Asp Arg Met Ile Gly Gln Tyr Ile Val Val Ser Pro Asn Ser Val
            20                  25                  30

Leu Lys Asn Ala Lys Leu Ala Pro Ala His Pro Leu Ala Asp Gln Val
        35                  40                  45

Lys Ile Ile Thr His Ser Gly Arg Ser Gly Arg Tyr Ala Val Glu Pro
```

```
                50                  55                  60
Tyr Asp Ala Lys Val Leu Met Pro Ala Gly Ala Val Pro Trp Pro
 65                  70                  75                  80

Glu Phe Leu Ala Leu Ser Glu Ser Ala Thr Leu Val Tyr Asn Glu Arg
                 85                  90                  95

Glu Phe Val Asn Arg Lys Leu Tyr His Ile Ala Met His Gly Pro Ala
                100                 105                 110

Lys Asn Thr Glu Glu Glu Gln Tyr Lys Val Thr Lys Ala Glu Leu Ala
                115                 120                 125

Glu Thr Glu Tyr Val Phe Asp Val Asp Lys Arg Cys Val Lys Lys
    130                 135                 140

Glu Glu Ala Ser Gly Leu Val Leu Ser Gly Glu Leu Thr Asn Pro Pro
145                 150                 155                 160

Tyr His Glu Leu Ala Leu Glu Gly Leu Lys Thr Arg Pro Ala Val Pro
                165                 170                 175

Tyr Lys Val Glu Thr Ile Gly Val Ile Gly Thr Pro Gly Ser Gly Lys
                180                 185                 190

Ser Ala Ile Ile Lys Ser Thr Val Thr Ala Arg Asp Leu Val Thr Ser
                195                 200                 205

Gly Lys Lys Glu Asn Cys Arg Glu Ile Glu Ala Asp Val Leu Arg Leu
    210                 215                 220

Arg Gly Met Gln Ile Thr Ser Lys Thr Val Asp Ser Val Met Leu Asn
225                 230                 235                 240

Gly Cys His Lys Ala Val Glu Val Leu Tyr Val Asp Glu Ala Phe Ala
                245                 250                 255

Cys His Ala Gly Ala Leu Leu Ala Leu Ile Ala Ile Val Arg Pro Arg
                260                 265                 270

Lys Lys Val Val Leu Cys Gly Asp Pro Met Gln Cys Gly Phe Phe Asn
                275                 280                 285

Met Met Gln Leu Lys Val His Phe Asn His Pro Glu Lys Asp Ile Cys
    290                 295                 300

Thr Lys Thr Phe Tyr Lys Tyr Ile Ser Arg Arg Cys Thr Gln Pro Val
305                 310                 315                 320

Thr Ala Ile Val Ser Thr Leu His Tyr Asp Gly Lys Met Lys Thr Thr
                325                 330                 335

Asn Pro Cys Lys Lys Asn Ile Glu Ile Asp Ile Thr Gly Ala Thr Lys
                340                 345                 350

Pro Lys Pro Gly Asp Ile Ile Leu Thr Cys Phe Arg Gly Trp Val Lys
                355                 360                 365

Gln Leu Gln Ile Asp Tyr Pro Gly His Glu Val Met Thr Ala Ala Ala
    370                 375                 380

Ser Gln Gly Leu Thr Arg Lys Gly Val Tyr Ala Val Arg Gln Lys Val
385                 390                 395                 400

Asn Glu Asn Pro Leu Tyr Ala Ile Thr Ser Glu His Val Asn Val Leu
                405                 410                 415

Leu Thr Arg Thr Glu Asp Arg Leu Val Trp Lys Thr Leu Gln Gly Asp
                420                 425                 430

Pro Trp Ile Lys Gln Leu Thr Asn Ile Pro Lys Gly Asn Phe Gln Ala
                435                 440                 445

Thr Ile Glu Asp Trp Glu Ala Glu His Lys Gly Ile Ile Ala Ala Ile
    450                 455                 460

Asn Ser Pro Thr Pro Arg Ala Asn Pro Phe Ser Cys Lys Thr Asn Val
465                 470                 475                 480
```

Cys Trp Ala Lys Ala Leu Glu Pro Ile Leu Ala Thr Ala Gly Ile Val
            485                 490                 495

Leu Thr Gly Cys Gln Trp Ser Glu Leu Phe Pro Gln Phe Ala Asp Asp
        500                 505                 510

Lys Pro His Ser Ala Ile Tyr Ala Leu Asp Val Ile Cys Ile Lys Phe
    515                 520                 525

Phe Gly Met Asp Leu Thr Ser Gly Leu Phe Ser Lys Gln Ser Ile Pro
530                 535                 540

Leu Thr Tyr His Pro Ala Asp Ser Ala Arg Pro Val Ala His Trp Asp
545                 550                 555                 560

Asn Ser Pro Gly Thr Arg Lys Tyr Gly Tyr Asp His Ala Ile Ala Ala
            565                 570                 575

Glu Leu Ser Arg Arg Phe Pro Val Phe Gln Leu Ala Gly Lys Gly Thr
        580                 585                 590

Gln Leu Asp Leu Gln Thr Gly Arg Thr Arg Val Ile Ser Ala Gln His
    595                 600                 605

Asn Leu Val Pro Val Asn Arg Asn Leu Pro His Ala Leu Val Pro Glu
610                 615                 620

Tyr Lys Glu Lys Gln Pro Gly Pro Val Glu Lys Phe Leu Asn Gln Phe
625                 630                 635                 640

Lys His His Ser Val Leu Val Val Ser Glu Glu Lys Ile Glu Ala Pro
            645                 650                 655

Arg Lys Arg Ile Glu Trp Ile Ala Pro Ile Gly Ile Ala Gly Ala Asp
        660                 665                 670

Lys Asn Tyr Asn Leu Ala Phe Gly Phe Pro Pro Gln Ala Arg Tyr Asp
    675                 680                 685

Leu Val Phe Ile Asn Ile Gly Thr Lys Tyr Arg Asn His His Phe Gln
690                 695                 700

Gln Cys Glu Asp His Ala Ala Thr Leu Lys Thr Leu Ser Arg Ser Ala
705                 710                 715                 720

Leu Asn Cys Leu Asn Pro Gly Gly Thr Leu Val Lys Ser Tyr Gly
            725                 730                 735

Tyr Ala Asp Arg Asn Ser Glu Asp Val Val Thr Ala Leu Ala Arg Lys
        740                 745                 750

Phe Val Arg Val Ser Ala Ala Arg Pro Asp Cys Val Ser Ser Asn Thr
    755                 760                 765

Glu Met Tyr Leu Ile Phe Arg Gln Leu Asp Asn Ser Arg Thr Arg Gln
770                 775                 780

Phe Thr Pro His His Leu Asn Cys Val Ile Ser Ser Val Tyr Glu Gly
785                 790                 795                 800

Thr Arg Asp Gly Val Gly Ala
            805

<210> SEQ ID NO 9
<211> LENGTH: 549
<212> TYPE: PRT
<213> ORGANISM: Artificial Sequence
<220> FEATURE:
<223> OTHER INFORMATION: nsp3 polypeptide

<400> SEQUENCE: 9

Ala Pro Ser Tyr Arg Thr Lys Arg Glu Asn Ile Ala Asp Cys Gln Glu
1               5                   10                  15

Glu Ala Val Val Asn Ala Ala Asn Pro Leu Gly Arg Pro Gly Glu Gly
            20                  25                  30

-continued

Val Cys Arg Ala Ile Tyr Lys Arg Trp Pro Thr Ser Phe Thr Asp Ser
            35                  40                  45

Ala Thr Glu Thr Gly Thr Ala Arg Met Thr Val Cys Leu Gly Lys Lys
    50                  55                  60

Val Ile His Ala Val Gly Pro Asp Phe Arg Lys His Pro Glu Ala Glu
65                  70                  75                  80

Ala Leu Lys Leu Leu Gln Asn Ala Tyr His Ala Val Ala Asp Leu Val
                85                  90                  95

Asn Glu His Asn Ile Lys Ser Val Ala Ile Pro Leu Leu Ser Thr Gly
                100                 105                 110

Ile Tyr Ala Ala Gly Lys Asp Arg Leu Glu Val Ser Leu Asn Cys Leu
            115                 120                 125

Thr Thr Ala Leu Asp Arg Thr Asp Ala Asp Val Thr Ile Tyr Cys Leu
            130                 135                 140

Asp Lys Lys Trp Lys Glu Arg Ile Asp Ala Ala Leu Gln Leu Lys Glu
145                 150                 155                 160

Ser Val Thr Glu Leu Lys Asp Glu Asp Met Glu Ile Asp Asp Glu Leu
                165                 170                 175

Val Trp Ile His Pro Asp Ser Cys Leu Lys Gly Arg Lys Gly Phe Ser
            180                 185                 190

Thr Thr Lys Gly Lys Leu Tyr Ser Tyr Phe Glu Gly Thr Lys Phe His
            195                 200                 205

Gln Ala Ala Lys Asp Met Ala Glu Ile Lys Val Leu Phe Pro Asn Asp
            210                 215                 220

Gln Glu Ser Asn Glu Gln Leu Cys Ala Tyr Ile Leu Gly Glu Thr Met
225                 230                 235                 240

Glu Ala Ile Arg Glu Lys Cys Pro Val Asp His Asn Pro Ser Ser Ser
                245                 250                 255

Pro Pro Lys Thr Leu Pro Cys Leu Cys Met Tyr Ala Met Thr Pro Glu
            260                 265                 270

Arg Val His Arg Leu Arg Ser Asn Asn Val Lys Glu Val Thr Val Cys
            275                 280                 285

Ser Ser Thr Pro Leu Pro Lys His Lys Ile Lys Asn Val Gln Lys Val
            290                 295                 300

Gln Cys Thr Lys Val Val Leu Phe Asn Pro His Thr Pro Ala Phe Val
305                 310                 315                 320

Pro Ala Arg Lys Tyr Ile Glu Val Pro Glu Gln Pro Thr Ala Pro Pro
            325                 330                 335

Ala Gln Ala Glu Glu Ala Pro Glu Val Val Ala Thr Pro Ser Pro Ser
            340                 345                 350

Thr Ala Asp Asn Thr Ser Leu Asp Val Thr Asp Ile Ser Leu Asp Met
            355                 360                 365

Asp Asp Ser Ser Glu Gly Ser Leu Phe Ser Ser Phe Ser Gly Ser Asp
            370                 375                 380

Asn Ser Ile Thr Ser Met Asp Ser Trp Ser Ser Gly Pro Ser Ser Leu
385                 390                 395                 400

Glu Ile Val Asp Arg Arg Gln Val Val Ala Asp Val His Ala Val
            405                 410                 415

Gln Glu Pro Ala Pro Ile Pro Pro Arg Leu Lys Lys Met Ala Arg
            420                 425                 430

Leu Ala Ala Ala Arg Lys Glu Pro Thr Pro Pro Ala Ser Asn Ser Ser
            435                 440                 445

-continued

```
Glu Ser Leu His Leu Ser Phe Gly Gly Val Ser Met Ser Leu Gly Ser
            450                 455                 460
Ile Phe Asp Gly Glu Thr Ala Arg Gln Ala Ala Val Gln Pro Leu Ala
465                 470                 475                 480
Thr Gly Pro Thr Asp Val Pro Met Ser Phe Gly Ser Phe Ser Asp Gly
                485                 490                 495
Glu Ile Asp Glu Leu Ser Arg Arg Val Thr Glu Ser Glu Pro Val Leu
            500                 505                 510
Phe Gly Ser Phe Glu Pro Gly Glu Val Asn Ser Ile Ile Ser Ser Arg
                515                 520                 525
Ser Ala Val Ser Phe Pro Leu Arg Lys Gln Arg Arg Arg Arg Arg Ser
            530                 535                 540
Arg Arg Thr Glu Tyr
545

<210> SEQ ID NO 10
<211> LENGTH: 616
<212> TYPE: PRT
<213> ORGANISM: Artificial Sequence
<220> FEATURE:
<223> OTHER INFORMATION: nsp4 polypeptide

<400> SEQUENCE: 10

Leu Thr Gly Val Gly Gly Tyr Ile Phe Ser Thr Asp Thr Gly Pro Gly
1               5                   10                  15
His Leu Gln Lys Lys Ser Val Leu Gln Asn Gln Leu Thr Glu Pro Thr
            20                  25                  30
Leu Glu Arg Asn Val Leu Glu Arg Ile His Ala Pro Val Leu Asp Thr
        35                  40                  45
Ser Lys Glu Glu Gln Leu Lys Leu Arg Tyr Gln Met Met Pro Thr Glu
    50                  55                  60
Ala Asn Lys Ser Arg Tyr Gln Ser Arg Lys Val Glu Asn Gln Lys Ala
65                  70                  75                  80
Ile Thr Thr Glu Arg Leu Leu Ser Gly Leu Arg Leu Tyr Asn Ser Ala
                85                  90                  95
Thr Asp Gln Pro Glu Cys Tyr Lys Ile Thr Tyr Pro Lys Pro Leu Tyr
            100                 105                 110
Ser Ser Ser Val Pro Ala Asn Tyr Ser Asp Pro Gln Phe Ala Val Ala
        115                 120                 125
Val Cys Asn Asn Tyr Leu His Glu Asn Tyr Pro Thr Val Ala Ser Tyr
    130                 135                 140
Gln Ile Thr Asp Glu Tyr Asp Ala Tyr Leu Asp Met Val Asp Gly Thr
145                 150                 155                 160
Val Ala Cys Leu Asp Thr Ala Thr Phe Cys Pro Ala Lys Leu Arg Ser
                165                 170                 175
Tyr Pro Lys Lys His Glu Tyr Arg Ala Pro Asn Ile Arg Ser Ala Val
            180                 185                 190
Pro Ser Ala Met Gln Asn Thr Leu Gln Asn Val Leu Ile Ala Ala Thr
        195                 200                 205
Lys Arg Asn Cys Asn Val Thr Gln Met Arg Glu Leu Pro Thr Leu Asp
    210                 215                 220
Ser Ala Thr Phe Asn Val Glu Cys Phe Arg Lys Tyr Ala Cys Asn Asp
225                 230                 235                 240
Glu Tyr Trp Glu Glu Phe Ala Arg Lys Pro Ile Arg Ile Thr Thr Glu
                245                 250                 255
```

```
Phe Val Thr Ala Tyr Val Ala Arg Leu Lys Gly Pro Lys Ala Ala
            260                 265                 270

Leu Phe Ala Lys Thr Tyr Asn Leu Val Pro Leu Gln Glu Val Pro Met
    275                 280                 285

Asp Arg Phe Val Met Asp Met Lys Arg Asp Val Lys Val Thr Pro Gly
290                 295                 300

Thr Lys His Thr Glu Glu Arg Pro Lys Val Gln Val Ile Gln Ala Ala
305                 310                 315                 320

Glu Pro Leu Ala Thr Ala Tyr Leu Cys Gly Ile His Arg Glu Leu Val
                325                 330                 335

Arg Arg Leu Thr Ala Val Leu Leu Pro Asn Ile His Thr Leu Phe Asp
            340                 345                 350

Met Ser Ala Glu Asp Phe Asp Ala Ile Ile Ala Glu His Phe Lys Gln
355                 360                 365

Gly Asp Pro Val Leu Glu Thr Asp Ile Ala Ser Phe Asp Lys Ser Gln
    370                 375                 380

Asp Asp Ala Met Ala Leu Thr Gly Leu Met Ile Leu Glu Asp Leu Gly
385                 390                 395                 400

Val Asp Gln Pro Leu Leu Asp Leu Ile Glu Cys Ala Phe Gly Glu Ile
                405                 410                 415

Ser Ser Thr His Leu Pro Thr Gly Thr Arg Phe Lys Phe Gly Ala Met
            420                 425                 430

Met Lys Ser Gly Met Phe Leu Thr Leu Phe Val Asn Thr Val Leu Asn
435                 440                 445

Val Val Ile Ala Ser Arg Val Leu Glu Glu Arg Leu Lys Thr Ser Arg
    450                 455                 460

Cys Ala Ala Phe Ile Gly Asp Asp Asn Ile Ile His Gly Val Val Ser
465                 470                 475                 480

Asp Lys Glu Met Ala Glu Arg Cys Ala Thr Trp Leu Asn Met Glu Val
                485                 490                 495

Lys Ile Ile Asp Ala Val Ile Gly Glu Arg Pro Pro Tyr Phe Cys Gly
            500                 505                 510

Gly Phe Ile Leu Gln Asp Ser Val Thr Ser Thr Ala Cys Arg Val Ala
    515                 520                 525

Asp Pro Leu Lys Arg Leu Phe Lys Leu Gly Lys Pro Leu Pro Ala Asp
530                 535                 540

Asp Glu Gln Asp Glu Asp Arg Arg Arg Ala Leu Leu Asp Glu Thr Lys
545                 550                 555                 560

Ala Trp Phe Arg Val Gly Ile Thr Gly Thr Leu Ala Val Ala Val Thr
                565                 570                 575

Thr Arg Tyr Glu Val Asp Asn Ile Thr Pro Val Leu Leu Ala Leu Arg
            580                 585                 590

Thr Phe Ala Gln Ser Lys Arg Ala Phe Gln Ala Ile Arg Gly Glu Ile
    595                 600                 605

Lys His Leu Tyr Gly Gly Pro Lys
610                 615

<210> SEQ ID NO 11
<211> LENGTH: 354
<212> TYPE: DNA
<213> ORGANISM: Artificial Sequence
<220> FEATURE:
<223> OTHER INFORMATION: subgenomic promoter (PSG) sequence, Sindbis
      3'CSE

<400> SEQUENCE: 11
```

```
cttgcagcat gatgctgact agcacacgaa gatgaccgct acgccccaat gatccgacca    60
gcaaaactcg atgtacttcc gaggaactga tgtgcataat gcatcaggct ggtacattag   120
atccccgctt accgcgggca atatagcaac actaaaaact cgatgtactt ccgaggaagc   180
gcagtgcata atgctgcgca gtgttgccac ataaccacta tattaaccat ttatctagcg   240
gacgccaaaa actcaatgta tttctgagga agcgtggtgc ataatgccac gcagcgtctg   300
cataactttt attatttctt ttattaatca acaaaatttt gtttttaaca tttc         354
```

```
<210> SEQ ID NO 12
<211> LENGTH: 425
<212> TYPE: DNA
<213> ORGANISM: Artificial Sequence
<220> FEATURE:
<223> OTHER INFORMATION: reverse-orientation promoter 5'UTR+5'CSE (rPSG)

<400> SEQUENCE: 12
attgacggcg tagtacacac tattgaatca aacagccgac caattgcact accatcacaa    60
tggagaagcc agtagtaaac gtagacgtag accccccagag tccgtttgtc gtgcaactgc  120
aaaaaagctt cccgcaattt gaggtagtag cacagcaggt cactccaaat gaccatgcta  180
atgccagagc attttcgcat ctggccagta aactaatcga gctggaggtt cctaccacag  240
cgacgatctt ggacataggc agcgcaccgg ctcgtagaat gttttccgag caccagtatc  300
attgtgtctg ccccatgcgt agtccagaag acccggaccg catgatgaaa tacgccagta  360
aactggcgga aaaagcgtgc aagattacaa acaagaactt gcatgagaag attaaggatc  420
tccgg                                                               425
```

```
<210> SEQ ID NO 13
<211> LENGTH: 347
<212> TYPE: DNA
<213> ORGANISM: Artificial Sequence
<220> FEATURE:
<223> OTHER INFORMATION: internal subgenomic promoter for RdRp (iPSG)

<400> SEQUENCE: 13
aagattcggt tacttccaca gcgtgccgcg tggcggatcc cctgaaaagg ctgtttaagt    60
tgggtaaacc gctcccagcc gacgacgagc aagacgaaga cagaagacgc gctctgctag   120
atgaaacaaa ggcgtggttt agagtaggta taacaggcac tttagcagtg gccgtgacga  180
cccggtatga ggtagacaat attacacctg tcctactggc attgagaact tttgcccaga  240
gcaaaagagc attccaagcc atcagagggg aaataaagca tctctacggt ggtcctaaat  300
agtcagcata gtacatttca tctgactaat actacaacac caccacc                347
```

```
<210> SEQ ID NO 14
<211> LENGTH: 347
<212> TYPE: DNA
<213> ORGANISM: Artificial Sequence
<220> FEATURE:
<223> OTHER INFORMATION: piggyBac (PB) transposon sequence, PiggyBAC 5'
      Terminal Repeat

<400> SEQUENCE: 14
cattctagat taaccctaga aagatagtct gcgtaaaatt gacgcatgca ttcttgaaat    60
attgctctct ctttctaaat agcgcgaatc cgtcgctgtg catttaggac atctcagtcg   120
ccgcttggag ctcccgtgag gcgtgcttgt caatgcggta agtgtcactg attttgaact   180
ataacgaccg cgtgagtcaa aatgacgcat gattatcttt tacgtgactt ttaagattta  240
```
actcatacga taattatatt gttatttcat gttctactta cgtgataact tattatatat      300
atattttctt gttatagata tcaactagaa tgctagcatg ggcccat      347

<210> SEQ ID NO 15
<211> LENGTH: 243
<212> TYPE: DNA
<213> ORGANISM: Artificial Sequence
<220> FEATURE:
<223> OTHER INFORMATION: PB transposon sequence, PiggyBAC 3' Terminal
      Repeat

<400> SEQUENCE: 15
agttttgtta ctttatagaa gaaattttga gtttttgttt tttttaata aataaataaa      60 cataaataaa ttgtttgttg aatttattat tagtatgtaa gtgtaaatat aataaaactt     120
aatatctatt caaattaata aataaacctc gatatacaga ccgataaaac acatgcgtca     180
attttacgca tgattatctt taacgtacgt cacaatatga ttatctttct agggttaatc     240
tag      243

<210> SEQ ID NO 16
<211> LENGTH: 8951
<212> TYPE: DNA
<213> ORGANISM: Artificial Sequence
<220> FEATURE:
<223> OTHER INFORMATION: transposable Sindbis amplifiable lentiviral
      transfer cassette sequence

<400> SEQUENCE: 16
gcaactgttg ggaagggcga tcggtgcggg cctcttcgct attacgccag ctggcgaaag      60
ggggatgtgc tgcaaggcga ttaagttggg taacgccagg gttttcccag tcacgacgtt     120
gtaaaacgac ggccagtgag cgcgcgtaat acgactcact atagggcgaa ttggggcgcg     180
ccattctaga ttaaccctag aaagatagtc tgcgtaaaat tgacgcatgc attcttgaaa     240
tattgctctc tctttctaaa tagcgcgaat ccgtcgctgt gcatttagga catctcagtc     300
gccgcttgga gctcccgtga ggcgtgcttg tcaatgcggt aagtgtcact gattttgaac     360
tataacgacc gcgtgagtca aaatgacgca tgattatctt ttacgtgact tttaagattt     420
aactcatacg ataattatat tgttatttca tgttctactt acgtgataac ttattatata     480
tatattttct tgttatagat atcaactaga atgctagcgc ggccgcctcg agggatccgg     540
agtcttatgc aatactcttg tagtcttgca acatggtaac gatgagttag caacatgcct     600
tacaaggaga gaaaaagcac cgtgcatgcc gattggtgga gtaaggtgg tacgatcgtg     660 ccttattagg aaggcaacag acgggtctga catggattgg acgaaccact gaattccgca     720
ttgcagagat attgtattta agtgcctagc tcgataccgt cgagattgac ggcgtagtac     780
acactattga atcaaacagc cgaccaattg cactaccatc acaatggaga agccagtagt     840
aaacgtagac gtagaccccc agagtccgtt tgtcgtgcaa ctgcaaaaaa gcttcccgca     900
atttgaggta gtagcacagc aggtcactcc aaatgaccat gctaatgcca gagcattttc     960
gcatctggcc agtaaaactaa tcgagctgga ggttcctacc acagcgacga tcttggacat    1020
aggcagcgca ccggctcgta gaatgttttc cgagcaccag tatcattgtg tctgccccat    1080
gcgtagtcca gaagacccgg accgcatgat gaaatatgcc agtaaactgg cggaaaaagc    1140
gtgcaagatt acaaacaaga acttgcatga agattaag gatctccgga ccgtacttga    1200
tacgccggat gctgaaacac catcgctctg ctttcacaac gatgttacct gcaacatgcg    1260

-continued

```
tgccgaatat tccgtcatgc aggacgtgta tagagccgag ggccgagggt ccctcctgac    1320
atgcggagac gttgaggaaa atcctggacc aatgggaacc tcacttcttt gctggatggc    1380
actttgtctt cttggagccg atcacgcaga tgctgagcag aagctcatca gtgaagagga    1440
cttgtctgga gggggaggga gtccggctcc caggccgcca acacctgcgc caactatcgc    1500
ctcccagcca ttgtccttga ggccagaggc atgtcgcccc gcagcgggag gcgccgtcca    1560
tacccgcggt ttggacttcg catgtgatat ttatatttgg gctccactcg cgggtacatg    1620
cggagtcttg ttgctctctc ttgtgattac gctttactgc aaccaccgga acagaaggcg    1680
agtatgtaaa tgtccccggc ccgtagtata gtcagcatag tacatttcat ctgactaata    1740
ctacaacacc accacctcta gaaccggtaa ggcaagcttt attgaggctt aagcagtggg    1800
ttccctagtt agccagagag ctcccaggct cagatctggt ctaaccagag agacccagta    1860
caagcaaaaa gcagatcttg tcttcgttgg gagtgaatta gcccttccag tccccccttt    1920
tcttttaaaa agtggctaag atctacagct gccttgtaag tcattggtct taaaggtacc    1980
gagctcgaat tccaggcggg gaggcggccc aaagggagat ccgactcgtc tgagggcgaa    2040
ggcgaagacg cggaagaggc cgcagagccg gcagcaggcc gcgggaagga aggtccgctg    2100
gattgagggc cgaagggacg tagcagaagg acgtcccgcg cagaatccag gtggcaacac    2160
aggcgagcag ccaaggaaag gacgatgatt tccccgacaa caccacggaa ttgtcagtgc    2220
ccaacagccg agccctgtc cagcagcggg caaggcaggc ggcgatgagt tccgccgtgg    2280
caatagggag ggggaaagcg aaagtcccgg aaaggagctg acaggtggtg gcaatgcccc    2340
aaccagtggg ggttgcgtca gcaaacacag tgcacaccac gccacgttgc ctgacaacgg    2400
gccacaactc ctcataaaga gacagcaacc aggatttata caaggaggag aaaatgaaag    2460
ccatacggga agcaatagca tgatacaaag gcattaaagc agcgtatcca catagcgtaa    2520
aaggagcaac atagttaaga ataccagtca atctttcaca aattttgtaa tccagaggtt    2580
gattgtcgag cccgggatct ctcgagacgc gttcaccggg gtggcagggc ctgcatgtgc    2640
agggcgtcgt aggtgtcctt ggtggcggtg ctcaggccct ggtacaggcc gtcgtggccc    2700
ttgccccggc gccgctcgcc cttcatgccg atctcgctgt aggcctcggc catcttgtcc    2760
ttctgcagct cgttgtacag gccctcctgg ggattcttcc ggcgaggctt gccgcccatc    2820
tcggggtccc gtcccgccg cttgtccagc acgtcgtact cctcccgccg tcccaggttc    2880
agctcgttgt acagctggtt ctggccctgc tggtaggctg gggcgtcggc gctccggctg    2940
aacttcaccc gcagctcgca gccgccttcc tcttcctcgg gaaccggca gctgcagccg    3000 tcctcctcct gggtggtctg cacgggccgc atgaagggct gcttgaagat gtacagcagc    3060
ttcttccggc cccgtttgca atacagtgta atcaccaggg acagcagcag cacccccgcat    3120 gtcccggcca ggggggccca gatatagatg tcgcaggcga agtccaggcc ccttgtgtgc    3180
acggctcctc cggcggcagg cctgcaggct tcaggccgca ggctcagggg ctggctggcg    3240
atggttgggg caggggtagg tggccgtggg gctggggtgg tggtgggatc cgaccgcttc    3300
agctccagct tggtgccggc gccgaaggtc agaggattga tgttccactg ctggcagtag    3360
taggtggcgc cgtcctcggc ctccatgttg ttgatggtca ggaagtagct ggtgccgctg    3420
ccgctgccgc tgaagcggtc gggcacgccg ctggccagct gctggtgtc gtagatccac    3480 cgcttagggc tggtgccgct cttctgctgg taccagtgca tgtagctcac gctgctgctg    3540
gcgctgcagg tcatggtcac cttctcgcca gggctggcgc tcatgatggc agggctctgg    3600
gtcagcacga tctggctgcc gcctccgcca gagccacctc cgccagagcc gccaccgcca    3660
```

```
gagctcacgg tcagggtggt gccctggccc cagtagtcca ggtagtcgcc gtacagcagg    3720
ctccgggcgc agaagtacac ggcgctgtcc tcgctggtca ggctgctcag ctgcatgtag    3780
gcggtggtgc tgctcttgtc ggcggtcagg gtggccttgt ccttgaactt gccgctgtag    3840
ttggtgtcct cgtcgccggg gtagatccgg ccgatccact ccaggccctt gccaggccgc    3900
tgcttcaccc agttcatcca gctgctgctg aaggcgtagc cgctggcctt gcagctgatc    3960
ttcacgctgg ctccgggctt caccagctcg ggtccgctct gctgcagctg cacctgggcg    4020
tcggcgtggt cggctcccag caggcacagg gccatccagc acagcaggct ggtgcccatg    4080
gtggcgtcga ccctggggag agaggtcggt gattcggtca acgagggagc cgactgccga    4140
cgtgcgctcc ggaggcttgc agaatgcgga acaccgcgcg ggcaggaaca gggcccacac    4200
taccgcccca caccccgcct cccgcaccgc cccttccgg ccgctgctct cggcgcgccc     4260
tgctgagcag ccgctattgg ccacagccca tcgcggtcgg cgcgctgcca ttgctccctg    4320
gcgctgtccg tctgcgaggg tactagtgag acgtgcggct tccgtttgtc acgtccggca    4380
cgccgcgaac cgcaaggaac cttcccgact taggggcgga gcaggaagcg tcgccggggg    4440
gcccacaagg gtagcggcga agatccgggt gacgctgcga acggacgtga agaatgtgcg    4500
agacccaggg tcggcgccgc tgcgtttccc ggaaccacgc ccagagcagc cgcgtccctg    4560
cgcaaaccca gggctgcctt ggaaaaggcg caacccaac cccgtggcct gcaggggaat     4620
tcgataaaat tttgaattt gtaatttgtt tttgtaattc tttagtttgt atgtctgttg     4680
ctattatgtc tactattctt tccctgcac tgtaccccc aatccccct tttcttttaa       4740
aagttaaccg ataccgtcga gatccgttca ctaatcgaat ggatctgtct ctgtctctct    4800
ctccaccttc ttcttctatt ccttcgggcc tgtcgggtcc cctcggggtt gggaggtggg    4860
tctgaaacga taatggtgaa tatccctgcc taactctatt cactatagaa agtacagcaa    4920
aaactattct taaacctacc aagcctccta ctatcattat gaataatttt atataccaca    4980
gccaatttgt tatgttaaac caattccaca aacttgccca tttatctaat tccataatt     5040
cttgttcatt cttttcttgc tggttttgcg attcttcaat taaggagtgt attaagcttg    5100
tgtaattgtt aatttctctg tcccactcca tccaggtcgt gtgattccaa atctgttcca    5160
gagatttatt actccaacta gcattccaag gcacagcagt ggtgcaaatg agttttccag    5220
agcaacccca aatccccagg agctgttgat ccttttaggta tctttccaca gccaggattc    5280
ttgcctggag ctgcttgatg ccccagactg tgagttgcaa cagatgctgt tgcgcctcaa    5340
tagccctcag caaattgttc tgctgctgca ctataccaga caataattgt ctggcctgta    5400
ccgtcagcgt cattgacgct gcgcccatag tgcttcctgc tgctcccaag aacccaagga    5460
acaaagctcc tattcccact gctctttttt ctctctgcac cactcttctc tttgccttgg    5520
tgggtgctac tcctaatggt tcaattttta ctactttata tttatataat tcacttctcc    5580
aattgtccct catatctcct cctccaggtc tgaagatcag cggccgcttg ctgtgcggtg    5640
gtcttacttt tgttttgctc ttcctctatc ttgtctaaag cttccttggt gtcttttatc    5700
tctatccttt gatgcacaca atagagggtt gctactgtat tatataatga tctaagttct    5760
tctgatcctg tctgaaggga tggttgtagc tgtcccagta tttgtctaca gccttctgat    5820
gtttctaaca ggccaggatt aactgcgaat cgttctagct ccctgcttgc ccatactata    5880
tgttttaatt tatattttt ctttccccct ggccttaacc gaattttttc ccatcgcgat     5940
ctaattctcc cccgcttaat actgacgctc tcgcacccat ctctctcctt ctagcctccg    6000
```

-continued

```
ctagtcaaaa ttttttggcgt actcaccagt cgccgcccct cgcctcttgc cgtgcgcgct      6060
tcagcaagcc gagtcctgcg tcgagagagc tcctctggtt tcccttttcgc tttcaagtcc      6120
ctgttcgggc gccactgcta gagattttcc acactgacta aaagggtctg agggatctct      6180
agttaccaga gtcacacaac agacgggcac acactacttg aagcactcaa ggcaagcttt      6240
attgaggctt aagcagtggg ttccctagtt agccagagag ctcccaggct cagatctggt      6300
ctaaccagag agacccaccg gtcgctacgc cccaatgatc cgaccagcaa aactcgatgt      6360
acttccgagg aactgatgtg cataatgcag gaattcgata tcaagctaga tctcacgtga      6420
gcatgcaggc cttgggccca atgatccgac cagcaaaact cgatgtactt ccgaggaact      6480
gatgtgcata atgcatcagg ctggtacatt agatccccgc ttaccgcggg caatatagca      6540
acactaaaaa ctcgatgtac ttccgaggaa gcgcagtgca taatgctgcg cagtgttgcc      6600
acataaccac tatattaacc atttatctag cggacgccaa aaactcaatg tatttctgag      6660
gaagcgtggt gcataatgcc acgcagcgtc tgcataactt ttattatttc ttttattaat      6720
caacaaaatt ttgtttttaa catttcaaaa aaaaaaaaaa aaaaaaaaaa aaaaaaaaaa      6780
aaagggaatt cccaacttgt ttattgcagc ttataatggt tacaaataaa gcaatagcat      6840
cacaaatttc acaaataaag catttttttc actgcattct agttgtggtt tgtccaaact      6900
catcaatgta tcttatcatg tctggatccg tcgagacgcg tcctgcaggc ctgcattaga      6960
tccattcatg aatgaattca tgtcgacata ctagttaaaa gttttgttac tttatagaag      7020
aaattttgag ttttttgtttt tttttaataa ataaataaac ataaataaat tgtttgttga      7080
atttattatt agtatgtaag tgtaaatata ataaaactta atatctattc aaattaataa      7140
ataaacctcg atatacagac cgataaaaca catgcgtcaa ttttacgcat gattatcttt      7200
aacgtacgtc acaatatgat tatctttcta gggttaatct agtatacgcg gcgacgacct      7260
gactgtttga caattaatca tcggcatagt atatcggcat agtataatac gactcactat      7320
aggagggcca ccatgattga acaagatgga ttgcacgcag gttctccggc cgcttgggtg      7380
gagaggctat tcggctatga ctgggcacaa cagacaatcg gctgctctga tgccgccgtg      7440
ttccggctgt cagcgcaggg gcgcccggtt ctttttgtca agaccgacct gtccggtgcc      7500
ctgaatgaac tgcaagacga ggcagcgcgg ctatcgtggc tggccacgac gggcgttcct      7560
tgcgcagctg tgctcgacgt tgtcactgaa gcgggaaggg actggctgct attgggcgaa      7620
gtgccggggc aggatctcct gtcatctcac cttgctcctg ccgagaaagt atccatcatg      7680
gctgatgcaa tgcggcggct gcatacgctt gatccggcta cctgcccatt cgaccaccaa      7740
gcgaaacatc gcatcgagcg agcacgtact cggatggaag ccggtcttgt cgatcaggat      7800
gatctggacg aagagcatca ggggctcgcg ccagccgaac tgttcgccag gctcaaggcg      7860
agcatgcccg acggcgagga tctcgtcgtg acacatggcg atgcctgctt gccgaatatc      7920
atggtggaaa atggccgctt ttctggattc atcgactgtg gccggctggg tgtggcggac      7980
cgctatcagg acatagcgtt ggctacccgt gatattgctg aagagcttgg cggcgaatgg      8040
gctgaccgct tcctcgtgct ttacggtatc gccgctcccg attcgcagcg catcgccttc      8100
tatcgccttc ttgacgagtt cttctgagcg ggactctggg gttcgaaatg accgaccaag      8160
cagtactaaa tgttaattaa ctagccatga ccaaaatccc ttaacgtgag ttttcgttcc      8220
actgagcgtc agacccccgta gaaaagatca aaggatcttc ttgagatcct ttttttctgc      8280
gcgtaatctg ctgcttgcaa acaaaaaaac caccgctacc agcggtggtt tgtttgccgg      8340
atcaagagct accaactctt tttccgaagg taactggctt cagcagagcg cagataccaa      8400
```

```
atactgttct tctagtgtag ccgtagttag gccaccactt caagaactct gtagcaccgc    8460
ctacatacct cgctctgcta atcctgttac cagtggctgc tgccagtggc gataagtcgt    8520
gtcttaccgg gttggactca agacgatagt taccggataa ggcgcagcgg tcgggctgaa    8580 cgggggttc gtgcacacag cccagcttgg agcgaacgac ctacaccgaa ctgagatacc     8640
tacagcgtga gctatgagaa agcgccacgc ttcccgaagg gagaaaggcg gacaggtatc    8700
cggtaagcgg cagggtcgga acaggagagc gcacgaggga gcttccaggg ggaaacgcct    8760
ggtatcttta tagtcctgtc gggtttcgcc acctctgact tgagcgtcga ttttgtgat     8820 gctcgtcagg ggggcggagc ctatggaaaa acgccagcaa cgcggccttt ttacggttcc    8880 tggcctttg ctggccttt gctcacatgt tcttaattaa cagggcgcgt cccattcgcc      8940
attcaggctg c                                                         8951
```